(12) United States Patent
Plaskos et al.

(10) Patent No.: US 12,290,254 B2
(45) Date of Patent: May 6, 2025

(54) METHOD OF PLANNING AN ARTHROPLASTY PROCEDURE

(71) Applicant: OMNIlife science, Inc., Raynham, MA (US)

(72) Inventors: Christopher Plaskos, Plymouth, MA (US); Christian Joly, Pleasanton, CA (US); Frederic Leger, Rennes (FR)

(73) Assignee: OMNIlife science, Inc., Raynham, MA (US)

( * ) Notice: Subject to any disclaimer, the term of this patent is extended or adjusted under 35 U.S.C. 154(b) by 270 days.

(21) Appl. No.: 17/681,040

(22) Filed: Feb. 25, 2022

(65) Prior Publication Data
US 2022/0175361 A1 Jun. 9, 2022

Related U.S. Application Data

(63) Continuation of application No. 16/132,088, filed on Sep. 14, 2018, now Pat. No. 11,596,392, which is a
(Continued)

(51) Int. Cl.
*A61B 17/02* (2006.01)
*A61B 34/10* (2016.01)
(Continued)

(52) U.S. Cl.
CPC ............ *A61B 17/025* (2013.01); *A61B 34/10* (2016.02); *A61B 34/20* (2016.02); *A61B 90/06* (2016.02); *A61F 2/3859* (2013.01); *A61F 2/389* (2013.01); *A61B 2017/00017* (2013.01); *A61B 2017/00221* (2013.01); *A61B 2017/00398* (2013.01);
(Continued)

(58) Field of Classification Search
CPC . A61B 17/025; A61B 34/20; A61B 2090/061; A61B 2090/065; A61B 2090/067; A61B 2017/0268; A61F 2/3859; A61F 2/389; A61F 2002/30616
See application file for complete search history.

(56) References Cited

U.S. PATENT DOCUMENTS

2006/0241640 A1* 10/2006 Briard .................. A61B 17/025
606/90
2007/0219561 A1* 9/2007 Lavallee .............. A61B 17/025
606/90
(Continued)

FOREIGN PATENT DOCUMENTS

WO 2016147153 A1 9/2016

OTHER PUBLICATIONS

Examination Report in counterpart Australian Patent Application No. 2016235175, mailed Sep. 12, 2019.
(Continued)

*Primary Examiner* — Sameh R Boles
(74) *Attorney, Agent, or Firm* — Kim IP Law Group LLC

(57) ABSTRACT

An orthopedic distraction device is provided. The orthopedic distraction device includes a first upper paddle for engaging a first bone of a joint, a lower paddle for engaging a second bone of the joint and a displacement mechanism. The displacement mechanism includes a drive assembly operable to move the upper paddle relative to the lower paddle. The lower paddle is releasably connected to the displacement mechanism.

20 Claims, 44 Drawing Sheets

Related U.S. Application Data continuation of application No. 15/078,954, filed on Mar. 23, 2016, now Pat. No. 10,321,904.

(60) Provisional application No. 62/309,711, filed on Mar. 17, 2016, provisional application No. 62/300,597, filed on Feb. 26, 2016, provisional application No. 62/218,840, filed on Sep. 15, 2015, provisional application No. 62/137,615, filed on Mar. 24, 2015.

(51) Int. Cl.
  *A61B 34/20* (2016.01)
  *A61B 90/00* (2016.01)
  *A61F 2/38* (2006.01)
  *A61B 17/00* (2006.01)
  *A61F 2/30* (2006.01)
  *A61F 2/46* (2006.01)

(52) U.S. Cl.
  CPC .............. *A61B 2017/00725* (2013.01); *A61B 2017/0268* (2013.01); *A61B 2034/104* (2016.02); *A61B 2034/105* (2016.02); *A61B 2034/2055* (2016.02); *A61B 2090/061* (2016.02); *A61B 2090/065* (2016.02); *A61B 2090/067* (2016.02); *A61F 2002/30616* (2013.01); *A61F 2/38* (2013.01); *A61F 2002/4666* (2013.01); *A61F 2002/469* (2013.01); *A61F 2002/4692* (2013.01)

(56) References Cited

U.S. PATENT DOCUMENTS

2010/0249659 A1  9/2010  Sherman et al.
2013/0165940 A1  6/2013  Disilvestro

OTHER PUBLICATIONS

International Search Report in International Application No. PCT/US2016/023838, mailed Jul. 9, 2016.
Office Action in counterpart Canadian Patent Application No. 1,954,125, mailed Aug. 21, 2017.
Office Action in counterpart Canadian Patent Application No. 1,954,125, mailed Mar. 13, 2017.
Office Action in counterpart European Patent Application No. 16716993.7, mailed Dec. 12, 2018.
Written Opinion in International Application No. PCT/US2016/023838, mailed Jul. 9, 2016.
Office Action in related U.S. Appl. No. 17/680,691 dated Feb. 13, 2024.
Office Action in US related U.S. Appl. No. 17/680,691 dated May 20, 2024.

\* cited by examiner

FORCE CONTROL

HEIGHT CONTROL

HEIGHT MODE

METHOD OF PLANNING AN ARTHROPLASTY PROCEDURE

CROSS-REFERENCE TO RELATED APPLICATIONS

This application is a continuation of U.S. patent application Ser. No. 16/132,088 filed Sep. 14, 2018 which is a continuation of U.S. patent application Ser. No. 15/078,954 filed Mar. 23, 2016 (now U.S. Pat. No. 10,321,904) which claims the benefit of U.S. Provisional Application Nos. 62/309,711 filed Mar. 17, 2016; 62/300,597 filed Feb. 26, 2016; 62/218,840 filed Sep. 15, 2015; and 62/137,615 filed Mar. 24, 2015, the entire disclosures of each of which are incorporated by reference herein in their entirety.

BACKGROUND OF THE INVENTION

Joint replacement surgery is performed on patients with degenerative joint diseases, such osteoarthritis and arthrosis, with the goals of relieving pain and restoring function, thus improving the quality of life for the patient. Although joint replacement surgery is exceedingly common, with approximately 700,000 knee replacement procedures performed annually in the U.S., it has been reported that a significant portion of patients (approximately one in five) are not satisfied with the results of their surgery. While this may be due to a number of factors, such as patient expectations, it is suspected that surgical technique related factors may play an important role in the number of cases that have less than optimal outcomes. In fact, several clinical studies have indicated that soft tissue related factors, such as instability and stiffness, are the leading cause for failure of total knee arthroplasty (TKA).

The act of achieving the appropriate soft-tissue tension and balance in joint replacement surgery is still regarded as somewhat of an art form by surgeons. This is partly because the act of assessing the tension in the soft tissues that surround a joint is largely a subjective process where the surgeon manually applies forces and moments to one side of the joint and observes the opening or compliance of the joint under the applied force by feel and by eye. Thus the assessment of soft tissue tension may vary depending on the surgeon performing the assessment, how they were trained, hold the limb by hand, and this may also vary from day to day, or from their left to right hand.

The standard of care in joint replacement surgery today is to use manual instrumentation which includes alignment rods, cutting blocks, provisional trial implants, and tensioning tools such as laminar spreaders or specifically designed manual spreaders. Robot and computer-assisted surgery systems have been introduced in the late 90's and have been increasing in development and use. However, most of systems currently on the market only partially address the soft tissue tensioning and balancing problem. Moreover, these systems still require a large number of instruments and provisional trial components to be available in the operating room.

BRIEF SUMMARY OF THE INVENTION

In accordance with a preferred embodiment, the present invention provides an orthopedic distraction device comprising a first upper paddle for engaging a first bone of a joint, a lower paddle for engaging a second bone of the joint, and a displacement mechanism having a drive assembly operable to move the upper paddle relative to the lower paddle. The lower paddle is releasably connected to the displacement mechanism.

The orthopedic distraction device further includes a second upper paddle for engaging the first bone of the joint. The first upper paddle extends further from the displacement mechanism than the second upper paddle. One of the first and second upper paddles includes an inwardly extending relief for clearance. The lower paddle includes fasteners for fastening to the second bone. The fastener is at least one of a pin, a plug fastener, and a screw. The lower paddle also includes at least one of a keel opening for receiving a keel punch, a fastener opening for receiving a fastener, and guide members for receiving a keel punch. The lower paddle is also sized and shaped to match a size and shape of an implant to be implanted in the second bone.

In accordance with another preferred embodiment, the present invention provides an orthopedic distraction device comprising an upper paddle, a plurality of augments each releasably connectable to the upper paddle for engaging a first bone of a joint, a lower paddle for engaging a second bone of the joint, and a displacement mechanism having a drive assembly operable to move one of the upper and lower paddles relative to the other of the upper and lower paddles. The orthopedic distraction device further includes another upper paddle. Each of the plurality of augments is configured to articulate with the first bone or a femoral trial implant, and includes a concave upper surface. Each of the plurality of augments when connected to the upper paddles includes a longitudinal axis extending at a non-perpendicular and non-parallel angle relative to a coronal plane of the displacement mechanism.

The upper paddle includes contact surfaces for articulating with a femur, and when the augment is connected to the upper paddle the contact surfaces are below the augment.

In accordance with a preferred embodiment, the present invention provides an orthopedic distraction device comprising at least one of a medial upper paddle and a lateral upper paddle for engaging a first bone of a joint, a lower paddle for engaging a second bone of the joint, and a displacement mechanism having a hermetically sealed drive assembly operable to displace the at least one of a medial upper paddle and a lateral upper paddle relative to the lower paddle.

The orthopedic distraction device further includes the other of the at least one of a medial upper paddle and a lateral upper paddle and a controller. The controller is configured to apply a first displacement force to the medial upper paddle and a second displacement force differing from the first displacement force to the lateral upper paddle. The drive assembly includes a drive mechanism operably connected to the at least one of a medial upper paddle and a lateral upper paddle. The drive mechanism includes a plunger driven by a motor for moving the at least one of a medial upper paddle and a lateral upper paddle. The drive mechanism is preferably a spindle drive.

The displacement mechanism comprises a paddle connector connectable to the at least one of a medial upper paddle and a lateral upper paddle, and a drive mechanism, and a sensor positioned below the drive assembly for measuring a force applied to the at least one of a medial upper paddle and a lateral upper paddle. The paddle connector moves relative to the drive mechanism.

The displacement mechanism further comprises a bellow for hermetically enclosing the paddle connector, and a flexure bracket for supporting the drive assembly.

The displacement mechanism also includes a housing body, and a flexure bracket connected to the housing body. The flexure bracket secures the drive assembly within the housing body.

The orthopedic distraction device further includes a controller operatively in communication with the displacement mechanism, and configured to move the displacement mechanism to receive a predetermined load force. The displacement mechanism further includes a sensor operatively in communication with the controller for measuring the load force applied to the at least one of a medial upper paddle and a lateral upper paddle.

The controller is configured to apply a displacement force to displace the at least one of a medial upper paddle and a lateral upper paddle relative to the lower paddle when engaging the first and second bones of the joint. The controller is also configured to vary the displacement force based on flexion angle of the first and second bones of the joint, and configured to determine a gap spacing between the at least one of a medial upper paddle and a lateral upper paddle, and the lower paddle based on the displacement force and a deflection factor.

In accordance with another preferred embodiment, the present invention provides an orthopedic distraction device comprising an upper paddle for engaging a first bone of a joint, a lower paddle for engaging a second bone of the joint, a displacement mechanism operable to displace the upper paddle relative to the lower paddle, and a controller operatively in communication with the displacement mechanism, and configured to apply varying displacement forces to displace the upper paddle from the lower paddle based on a relative position between the first and second bones of the joint. The displacement mechanism can include a drive assembly operable to displace the upper paddle relative to the lower paddle.

The displacement mechanism includes a drive assembly to displace the upper paddle relative to the low paddle.

The controller is configured to apply varying displacement forces throughout a range of motion of the joint, and apply varying displacement forces based on a joint angle of the joint. Further, the controller includes a memory having stored thereon a predetermined force profile for applying said varying displacement forces throughout a range of motion of the joint. Furthermore, the controller includes a predefined force versus flexion angle profile stored in a memory for determining the varying displacement forces to apply.

The force versus flexion angle profile is defined by a user and stored in a memory of the controller for determining the varying displacement forces to apply. The force versus flexion angle profile for determining the varying displacement forces to apply is adjustable by a user intraoperatively during surgery. The varying displacement forces are adjustable. The force versus flexion angle profile for determining the varying displacement forces to apply is adjustable by a user throughout a range of motion of the joint. The force versus flexion angle profile is displayed on a display. Further, the force versus flexion angle profile on the display is adjustable by a user. Furthermore, the force versus flexion angle profile on the display includes node control points adjustable by a user.

The controller is also configured to measure a gap spacing between the first and second bones of the joint upon applying said varying displacement forces and determine an implant position based off the measured gap spacing.

In accordance with a preferred embodiment, the present invention provides an orthopedic distraction device comprising a first upper paddle for engaging a first bone of a joint, a lower paddle for engaging a second bone of the joint, and a displacement mechanism. The displacement mechanism includes a housing, and a drive assembly within the housing operable to displace the first upper paddle relative to the lower paddle. The drive assembly is axially movable between a first position and a second position spaced from the first position.

The orthopedic distraction device further includes a second upper paddle for engaging the first bone, and a flexure bracket mounted to the housing with the drive assembly is mounted to the flexure bracket. The flexure bracket includes a rigid portion and a flexure portion moveable relative to the rigid portion.

The orthopedic distraction device further includes a sensor positioned within the housing and below the drive assembly. The drive assembly engages the sensor in both the first and second positions, and is connected to the first upper paddle.

A bellows assembly is connected to the first upper paddle and drive assembly. The bellows assembly is movable relative to the drive assembly.

In accordance with another preferred embodiment, the present invention provides an orthopedic instrument kit. The kit includes a plurality of femoral trail implants of incrementally different sizes and an orthopedic distraction device. The orthopedic distraction device includes a first upper paddle, a plurality of lower paddles, and a displacement mechanism having a drive assembly operable to move the upper paddle relative to the lower paddle, wherein each lower paddle is independently connectable to the displacement mechanism.

The kit further includes a plurality of tibial implants. Each of the plurality of lower paddles has an overall profile sized and shaped to correspond to a size and shape of an overall profile of the plurality of tibial implants. Further, the kit includes a plurality of augments each releasably connectable to the first upper paddle. Each of the plurality of augments has an articulating surface that corresponds in size to a size of each of the plurality of femoral trial implants.

In accordance with a preferred embodiment, the present invention provides an orthopedic distraction device with a controller and a display. The orthopedic distraction device includes medial and lateral upper paddles for engaging a first bone of a joint, a lower paddle for engaging a second bone of the joint, and a displacement mechanism having a drive assembly operable to supply a displacement force to the upper and lower paddles. The orthopedic distraction device further includes a non-transitory computer-readable medium including instructions that, when executed by a processor, cause the processor to measure a displacement between the upper and lower paddles, and display on a display the displacement forces applied to the upper and lower paddles verses displacement.

In accordance with another preferred embodiment, the present invention provides a computer aided orthopedic surgery system that includes a three dimensional position tracking system and an orthopedic distraction device. The orthopedic distraction device includes upper paddles for engaging a first bone of a joint, and a lower paddle for engaging a second bone of the joint. The lower paddle includes a reference marker trackable by the three dimensional position tracking system. The orthopedic distraction device further includes a displacement mechanism having a drive assembly operable to move the upper paddles relative to the lower paddle. The computer aided orthopedic surgery system further includes a computer having a memory for tracking the reference marker and a display for displaying the tracked reference marker. Furthermore, the computer aided orthopedic surgery system can include a robotic system having a robotic arm attached to the orthopedic distraction device.

In accordance with a preferred embodiment, the present invention provides a computer aided orthopedic surgery system that includes a three dimensional position tracking system and an orthopedic distraction device. The orthopedic distraction device includes upper paddles for engaging a first bone of a joint, a lower paddle for engaging a second bone of the joint, and a displacement mechanism having a drive assembly operable to move the upper paddles relative to the lower paddle. The computer aided orthopedic surgery system further includes reference markers for tracking a position of the first bone and second bone and a computer. The computer includes a display, a processor, and a memory having stored thereon software executable by the processor to track the position of the reference markers and determine a gap spacing between the upper paddles and the lower paddle throughout a range of motion of the joint, a varus/valgus angle between the upper paddles and lower paddle throughout a range of motion of the joint, and output on the display an overlay of the varus/valgus angle and gap spacing throughout a range of motion of the joint.

In accordance with another preferred embodiment, the present invention provides a computer aided orthopedic surgery system that includes, an orthopedic distraction device and a computer. The orthopedic distraction device includes upper paddles for engaging a first bone of a joint, a lower paddle for engaging a second bone of the joint, and a displacement mechanism having a drive assembly operable to supply displacement forces to the upper and lower paddles. The computer includes a display, a processor, and a non-transitory computer-readable medium having stored thereon at least one of a femoral knee implant model and a tibial knee implant model and computer program instructions executable by the processor to cause the computer to determine a force elongation profile of a displacement between the upper and lower paddles and the displacement forces, and output on the display a position of the femoral knee implant model on a computer model of the first bone and the displacement forces on the positioned femoral knee implant model based on the force elongation profile. The computer is also configured to adjust the position of the implant and display predicted force based on the force elongation profile and the adjusted position of the implant and corresponding gap.

The computer further includes computer program instructions to cause the computer to output on the display a position of the tibial knee implant model on a computer model of the second bone and a displacement force on the positioned tibial knee implant model based on the force elongation profile. Further, the computer includes computer program instructions to cause the computer to output on the display a position of the femoral knee implant model on a computer model of the first bone, a position of the tibial knee implant model on a computer model of the second bone, and at least one of a position of contact force and a magnitude of contact force between the femoral knee implant model and the tibial knee implant model based on the force elongation profile. Furthermore, the computer includes computer program instructions to cause the computer to output on the display a predicted force indicative of at least one of ligament tension forces and soft tissue forces of the joint as a function of a planned position of the implant model based on the force elongation profile. The implant model can be a femoral implant model and/or a tibial implant model.

The computer includes computer program instructions to cause the computer to output on the display a predicted force on the at least one of a femoral knee implant model and a tibial knee implant model as a function of gap spacing between the first and second bones based on the force elongation profile. Further, the computer includes computer program instructions to cause the computer to output on the display a predicted force on the at least one of a femoral knee implant model and a tibial knee implant model as a function of flexion angle between the first and second bones based on the force elongation profile.

In accordance with a preferred embodiment, the present invention provides a total knee arthroplasty trialing system that includes a plurality of femoral trial components each having a unique surface geometry profile and an adjustable insert trial system. The adjustable insert trial system includes an upper paddle, a lower paddle, a displacement mechanism having a drive assembly operable to adjust a spacing between the upper paddle and the lower paddle between a first position and a second position, and a plurality of insert trial augments connectable to the upper paddle, each having an upper surface complementary in shape to a respective surface geometry of the plurality of femoral trial components. Each of the plurality of insert trial augments can have the same minimum thickness. The lower paddle includes fasteners for fastening to a bone and guide members for receiving a keel punch. The fastener is at least one of a pin, a plug fastener, and a screw. The lower paddle can also include at least one of a keel opening for receiving a keel punch and a fastener opening for receiving a fastener. The lower paddle is releasably connected to the displacement mechanism. The adjustable insert trial system further comprises a controller configured to automatically adjust the spacing between the upper and lower paddles to achieve substantially equal forces on the upper and lower paddles at about full extension and at about 90 degrees flexion. Further, the adjustable insert trial system comprises a controller configured to automatically adjust the spacing between the upper and lower paddles to achieve substantially equal forces on the upper and lower paddles throughout a full range of motion. Furthermore, the adjustable insert trial system comprises a controller configured to vary a force applied by the upper and lower paddles based on flexion angle. The adjustable insert trial system further comprises a controller configured to determine a trial insert thickness based on a force applied by the upper and lower paddles, and a deflection factor. A controller of the adjustable insert trial system is configured to determine an optimal spacing between the upper and lower paddles throughout a range of motion. The controller is also configured to determine an optimal trial insert thickness based on spacing between the upper and lower paddles throughout a range of motion. The adjustable insert trial system further comprises a reference marker for tracking a position of the lower paddle with a three dimensional position tracking system.

In accordance with another preferred embodiment, the present invention provides a method for planning and assessing bone resections in an arthroplasty procedure of a knee joint comprising, using a computer aided orthopedic surgery system, tracking a position of a femur and tibia of the knee joint with a three dimensional position tracking system, resecting a proximal portion of the tibia and measuring a location of the tibial resection, inserting a joint distraction device having a lower paddle and at least one upper paddle into the knee joint, and positioning the lower paddle on the resected surface of the tibia. Using a computer aided orthopedic surgery system, controlling a force applied between the tibia and femur with the joint distraction device, measuring relative positions between the tibia and the femur during a range of motion of the knee joint while the joint distraction device is controlling the force applied between the tibia and the femur, determining an initial position and size of a 3D computer femoral implant model on a computer model of the femur bone, calculating a predicted gap versus flexion curve between the 3D computer femoral implant model surface and at least one of the location of the tibial resection or a surface of a planned 3D computer tibial implant model, based on the planned position of the 3D computer femoral implant model and the measured relative positions of the tibia and femur during the range of knee flexion angles, displaying on a computer display the planned the position of the femoral component and the calculated gap curves, adjusting the planned femoral position or size and dynamically updating the predicted gap versus flexion curve as a function of the adjusted position and/or size, resecting the femur according to the adjusted plan and inserting a femoral trial implant or actual implant, controlling the height of the joint distraction device to match the height of the planned 3D computer tibial implant model, and using a computer aided orthopedic surgery system, measuring forces acting on the joint distraction device during a second range of motion of the knee joint and displaying forces versus flexion on the display.

The method further comprises, using a computer aided orthopedic surgery system, varying a displacement of the upper and lower paddles of the joint distraction device to correspond to a tibial insert thickness size, measuring forces acting on the joint distraction device during a third range of motion of the knee joint, displaying said forces versus flexion on the display, color coding the force versus flexion curve displayed on the display, wherein the color codes correspond to a magnitude of force, and registering points on the femur bone with a three dimensional position tracking system to obtain a computer model of the femur. The method includes adding augments to the joint distraction device to replicate an upper surface of the tibial implant to be implanted in the knee joint.

In accordance with a preferred embodiment, the present invention a method for selecting a thickness of a tibial insert implant in an arthroplasty procedure of a knee joint comprising resecting femur and tibial bones to receive femoral and tibial implants, inserting a femoral implant on the resected femur bone, and inserting a joint distraction device between the resected femur and tibia bones. The joint distraction device includes an upper articulating surface that matches a tibial insert upper surface, a lower plate, an automatic active spacing device for controlling a space between the upper surface and lower plate, and force sensors for sensing a force between the upper articulating surface and lower plate. The method further includes, using a computer aided orthopedic surgery system, controlling a spacing between of the upper articulating surface and the lower plate of the joint distraction system, measuring forces between the upper articulating surfaces and lower plate during a range of motion of the knee joint, displaying the measured forces on a display, adjusting the spacing between of the upper articulating surface and the lower plate of the joint distraction system and measuring forces between the upper articulating surfaces and lower plate during a range of knee flexion angles, and selecting a thickness of the tibial insert to implant based on the force measurements.

The method further comprises, using a computer aided orthopedic surgery system, controlling the spacing between of the upper articulating surface and the lower plate of the active ligament balancer to match a thickness of the tibial implant, displaying the measured forces as a function of flexion angle, displaying the measured forces on a computer screen display, color coding the measured forces according to a magnitude of force, adjusting the rotation of the active ligament balancer on the tibial resection, tracking and storing a position of the active ligament balancer during a range of motion of the knee joint. The method also includes guiding a location of a tibial keel punch with the lower plate of the active ligament balancer.

In accordance with yet another preferred embodiment, the present invention provides a method for planning and assessing bone resections in an arthroplasty procedure comprising receiving bone morphology data of a joint, joint gap data and relative position data of a first bone and a second bone of the joint, receiving user input data indicative of an applied distraction force, controlling the applied distraction force supplied by a joint distraction device according to the received user input data, adjusting the applied distraction force as a function of relative position of first and second bones, recording relative positions of the first and second bones of the joint while controlling the applied distraction force, positioning and sizing at least one of a first implant on the first bone and a second implant on the second bone, based off of the recorded relative positions of the first and second bones, determining a position and size of an implant on at least one of the first and second bones, determining a position and size of a first implant on the first bone and a second implant on the second bone, displaying the determined position and/or size of the implant on the at least one of the first and second bones. Displaying the determined position and/or size of the first implant on the first bone and the second implant on the second bone, determining a resection depth of the first bone based on the determined position and/or size of the first implant and a resection depth of the second bone based on the determined position and/or size of the second implant, displaying a predictive gap between the first implant on the first bone and the second implant on the second bone, displaying a predictive gap between the first and second bones, displaying a predictive gap between the implant on one of the first and second bones, and the other of the first and second bones, receiving a user input to adjust the position and/or size of the implant on one of the first and second bones, displaying resection depths, and gaps between the first and second bones, based on the received user input to adjust the position and/or size of the first or second implant, positioning a robotic arm or cutting guide to the determined resection depth of the first or second bone, receiving user input on a selected thickness of a tibial implant as the second implant for the second bone, controlling a height of the joint distraction device based on the selected thickness of the tibial implant, sensing a force acting on the joint distraction device at the controlled height position while measuring the relative position of the first bone and second bone, displaying the first implant on the first bone and/or the second implant on the second bone, displaying the force acting on the distraction device on a display and displaying the relative positions of the first and second bones on the display, and/or displaying a graph of force versus flexion angle.

BRIEF DESCRIPTION OF THE SEVERAL VIEWS OF THE DRAWINGS

The foregoing summary, as well as the following detailed description of the preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the Drawings.

DETAILED DESCRIPTION OF THE INVENTION

Reference will now be made in detail to the preferred embodiments of the invention illustrated in the accompanying drawings. Wherever possible, the same or like reference numbers will be used throughout the drawings to refer to the same or like features. It should be noted that the drawings are in simplified form and are not drawn to precise scale. In reference to the disclosure herein, for purposes of convenience and clarity only, directional terms such as top, bottom, above, below and diagonal, are used with respect to the accompanying drawings. The term "proximal" refers to being nearer to the center of a body or a point of attachment. The term "distal" refers to being away from the center of a body or from a point of attachment. Such directional terms used in conjunction with the following description of the drawings should not be construed to limit the scope of the invention in any manner not explicitly set forth. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Ranges throughout this disclosure and various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the embodiments of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

In accordance with preferred embodiments and aspects of the present invention, there is provided the following:

Computer Aided Orthopedic Surgery System

Figure 1:
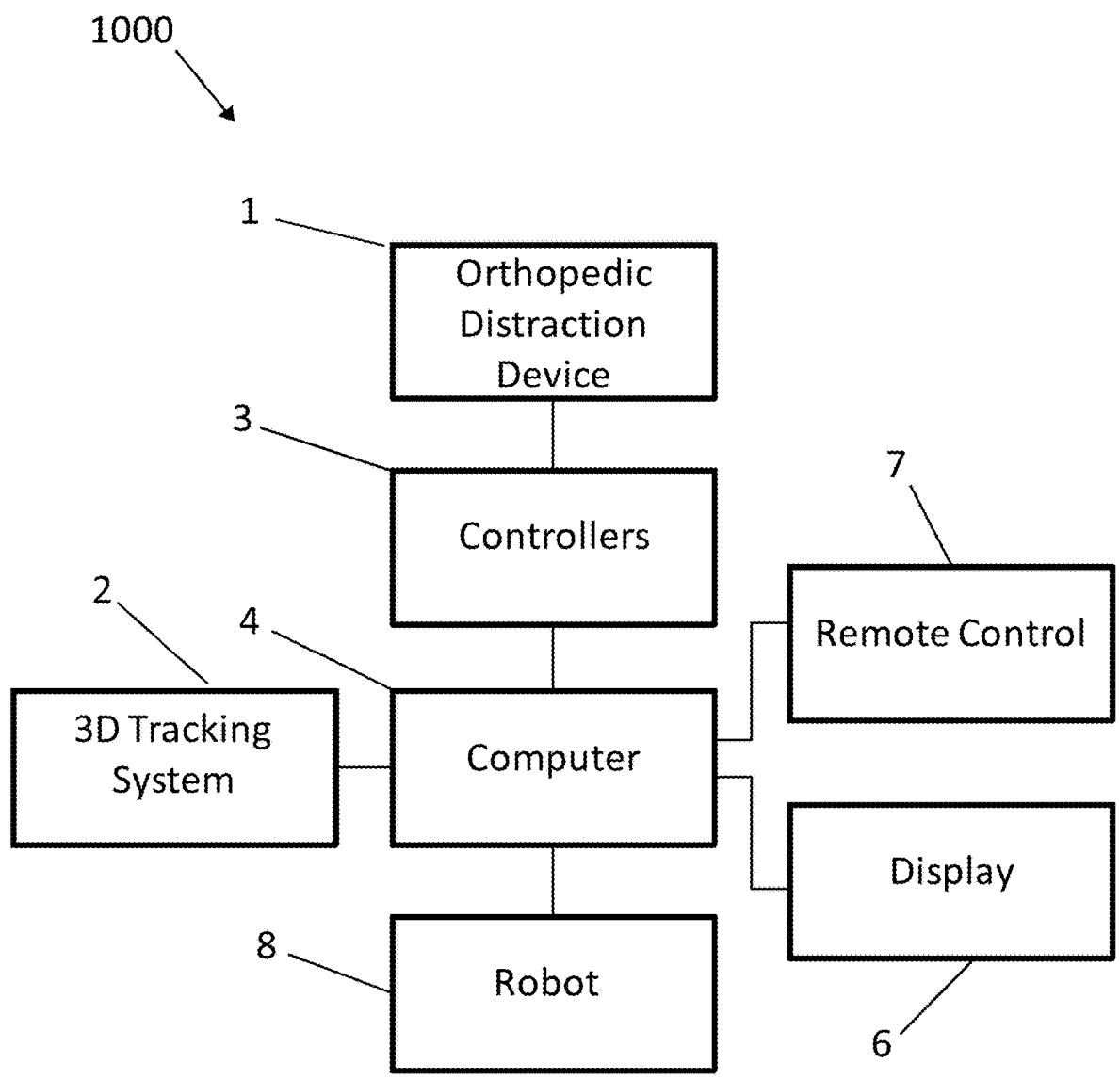
FIG. 1 is a schematic diagram of a computer aided orthopedic surgery system in accordance with a preferred embodiment of the present invention.

In accordance with a preferred embodiment, the present invention provides computer-assisted orthopedic surgery (CAOS) 1000, or navigation system, FIG. 1, for joint replacement or resurfacing procedures, such as knee arthroplasty procedures including unicondylar knee arthroplasty (UKA), total knee arthroplasty (TKA), or revision TKA. Although the system is primarily described in the context of knee arthroplasty, it should be understood that the system could be used for other surgical procedures, such as hip, ankle, shoulder or elbow arthroplasty, or ligament reconstruction procedures such as Anterior or Posterior Cruciate Ligament (ACL or PCL) reconstructions, and Medial or Lateral Collateral Ligament (MCL or LCL) reconstructions.

The CAOS system preferably includes a three dimensional (3D) position tracking system 2, for tracking the positions of the patient's bones and surgical instruments in 3D space. Any technology for position tracking may be used, including optical, electromagnetic, ultrasonic, radiofrequency, or accelerometer based tracking systems. Optical tracking systems usually use passive (retro-reflective) or active (LED) markers which are attached to the bones (for example, tibial reference marker 107 and femoral reference marker 106 shown in FIG. 6A) and tracked using an optical camera that is in communication with a central computer 4 of the CAOS station. Non-invasive tracking systems may also be used, such as transcutaneous ultrasound based tracking technology, or by tracking markers on the skin of the patient and compensating for motion of the skin relative to the underlying bones.

The CAOS system includes capabilities for establishing a coordinate system, such as a Cartesian coordinate system (x,y,z), associated with each bone. The coordinate system can correspond to the directions of the anatomical planes of each bone (x=anteroposterior, y=mediolateral, z=proximodistal). The CAOS system further allows for registering the anatomy of the patient's bones and in particular the anatomy in the vicinity of the patient's joint to be operated on, as well as the mechanical axis of the patient's leg, including the tibial mechanical axis 99, femoral mechanical axis 98, and overall mechanical axis of the leg (see FIG. 6A). The CAOS system also includes capabilities for generating a computer model of the patient's joint, using either information from pre-operative images, or by using generic models that are not specific to the patient but created or deformed to match the patient anatomy acquired or digitized in the OR. CAOS systems and methods for creating computer bone models applicable to the present invention are disclosed e.g., in U.S. Pat. Nos. 8,126,533 and 9,248,001, the entire disclosures of which are incorporated by reference herein for all purposes.

The CAOS system may include a probe for scanning the surface of the bones, such as a point probe that is physically touched to or slid along the bone surface while its position is being tracked relative to the bone by the 3D tracking system, or an echographic probe for collecting points through the skin and underlying soft tissues. The CAOS system can also include instruments for measuring the location of bone cut surfaces made in the bone for receiving an implant. For example a plate or planar probe (as known as a cut controller) can be used to measure the 3D location, angles and depths of bone resections such as the tibial resections and proximal femoral resections.

The CAOS system includes a central computer 4 for computing data and for connecting peripherals, including the tracking system, and a display 6 or multiple displays for displaying information in the OR. Any type of displays may be used, including 2D or 3D computer monitor screens, or heads-up and/or head-mounted displays. The display may also be a touch screen allowing the user to enter data and provide various control inputs to the system. Additionally, a remote control 7 may be used, such as a battery operated handheld wireless remote control device with buttons that can either be held in hand, placed on the OR table, or attached to a surgical instrument or an orthopedic distraction device 1 (also referred to herein as a ligament balancer). The remote control 7 may also be a wireless tablet computer with a touchscreen that can be either held by a non-sterile user (for example a nurse or technical support staff), attached to a CAOS workstation, or draped with sterile drapes and placed directly in the surgical field (for instance, attaching to the surgical table), allowing the surgeon or surgeon assistant to control the system. The remote control may also be a foot switch or foot pedal that is either in wireless or wired communication with the computer 4.

The computer and/or controller includes a processor and a memory having stored thereon software or computer instructions for planning the joint replacement procedure, including algorithms for planning the position of implants on the patients bones based off of bone morphology data and off of ligament data. The software and algorithms of the CAOS in accordance with the present embodiments are further discussed below. The software may include modules for assessment of the final ligament balance of the surgical procedure once the implants are in place. As used herein to describe the configuration of the controller or computer, configured to means that the controller or computer includes software or computer instructions stored in memory executable by the processor to cause the computer to function and operate as specified.

The CAOS system may include a robot 8 for executing the bone resections according to the plan. The robot may be floor mounted, table mounted, bone mounted, or handheld and may be programmed to provide autonomous or haptic guidance of the resections using various tools such as reciprocating, oscillating or rotating cutting tools, including bone saws, blades, burrs, mills, or reamers, or energy based (laser) cutting tools. Exemplary robots applicable to the present invention include those disclosed in U.S. Patent Application Publication No. 2011/0130761 and U.S. Pat. No. 8,840,629, the entire disclosures of which are incorporated by reference herein in their entirety for all purposes.

In accordance with another aspect, the CAOS system 1000 includes a robotic system 1010 having a robotic arm 1012. The robotic system, for example, can be programmed with a three-dimensional virtual region of constraint that is registered to a patient and the robotic arm can be configured to include three or more degrees of freedom. Robotic systems applicable to the present invention includes those disclosed in U.S. Pat. Nos. 9,002,426 and 7,747,311, the entire disclosures of which are hereby incorporated by reference herein in their entirety for all purposes. The robotic system 1010 is operatively in communication with the computer 4, programmable to carry out predetermined task and/or functions.

Figure 18:
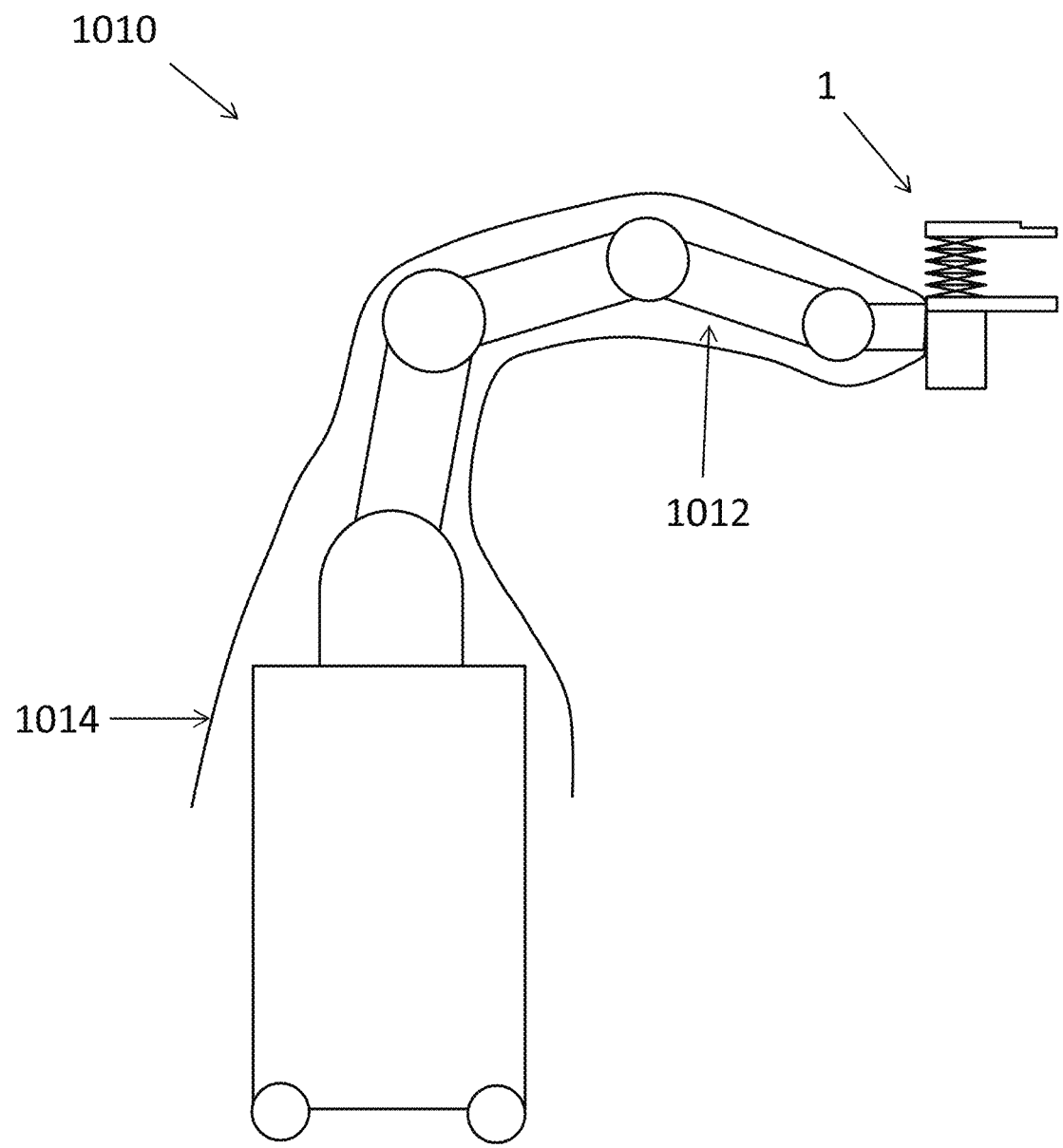
FIG. 18 is a perspective view of a robotic system of the computer aided orthopedic surgical system of the present invention having a robotic arm attached to a distraction device.

As shown in FIG. 18, the robotic system 1010 includes the orthopedic distraction device or ligament balancer 1, as further described below. That is, the distraction device is attached to the end of the robotic arm for control and manipulation of the distraction device. In this manner, cables extending from the distraction device can be run through or integrated into the robotic arm, or attached to the robotic arm, either internally or externally of the arm's outer housing.

In operation, the robotic arm is used to support and position the distraction device in the knee joint, thus providing the ability to compensate for the weight of the distraction device during use. Further, to maintain the sterile field in the OR, the robotic arm can be draped so as to forego the need to sterilize the robotic arm. When draped with sterile draping 1014, the distraction device can be sterilized and attached to the robotic arm on top of the sterile drape using dedicated couplings. Alternatively, the distraction device can be non-sterile and attached to the robotic arm under the sterile draping, with the upper and lower paddles of the distraction device are sterilized and extending out through the sterile draping.

Figure 19:
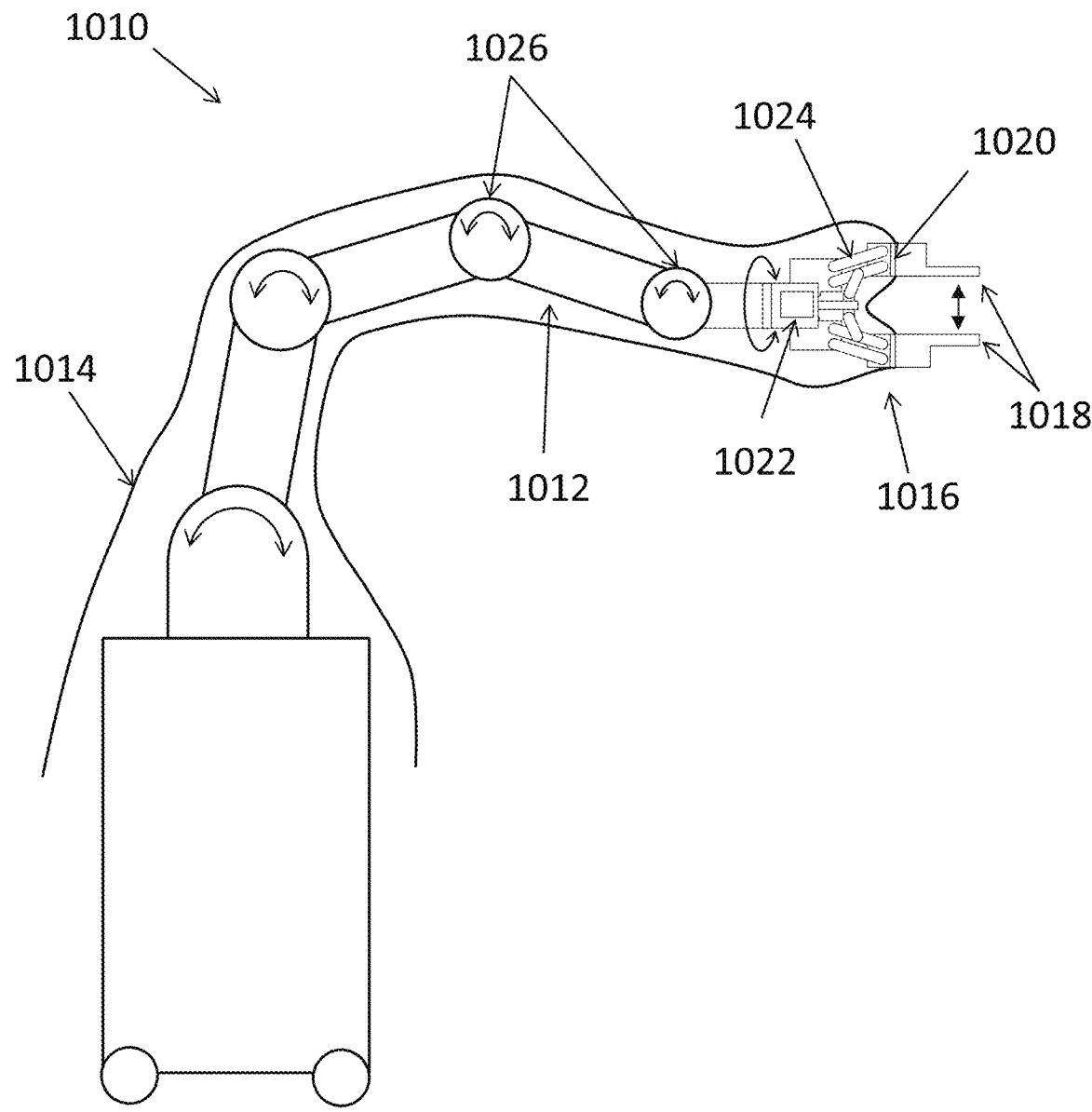
FIG. 19 is a perspective view of a robotic system of the computer aided orthopedic surgical system of the present invention having a robotic arm with an integrated distraction device on its distal end.

In accordance with another aspect, the distractor 1016 and force sensors are integrated into the distal end of the robotic arm, i.e. built into the arm, as shown in FIG. 19. In other words, the distal end of the robotic arm 1016 is equipped with one or more force sensors 1020 and one or more actuators 1022 that are configured to distract the bones of the joint, and function as the distractor in any of the embodiments and modes of control and function below mentioned (force control, height control, force-height control, disabled and enabled, virtual trailing, and so on). The upper and lower paddles 1018 can be modular and attached to the distractor (or end-effector) of the robotic arm, so that different designs of paddles may be attached for different purposes. The robotic arm 1010 with the distractor 1016 can be draped with a drape 1014 to keep the field sterile, and the paddles may be attached to the robotic arm end effector (distractor) through the drape. Force sensors 1020 can be integrated into the distractor mechanism behind the drape 1014 so that they do not need to be sterilized. The distractor can be configured to distract using linear sliding joints as shown in FIG. 18, or rotational joints that generate relative parallel motion of the paddles via a parallel linkage mechanism 1024 (FIG. 19), to keep the upper and lower paddles 1018 parallel to one another during distraction or post-resection trialing. Any lateral movement of the paddles relative to the bones that is created as a result of the actuator 1022 and parallel linkage mechanism 1024 moving the paddles closer or further away from one another can be compensated for by motion of the other joints 1026 of the robotic-arm 1012. The robotic arm can be mobile and have wheels that allow it to be moved on the floor, or it can be mounted directly to the operating room table. For example, the base of the robot can be clamped on the side rails of the table and can be light and portable so it can be easily transported from OR to OR or from hospital to hospital. The end effector can be configured to be a distractor as well as a robotic gripper, which would allow it to grip or hold other tools such as a bone cutting burr or saw for cutting the bones of the joint for inserting the implants according the plan generated by the CAOS system and the data acquired with the distractor.

The orthopedic distraction device or ligament balancer 1 is in communication with the central computer 4, and controllers 3 for controlling the motion and function of the ligament balancer. The ligament balancer includes a drive assembly, e.g., actuators 131 (FIG. 4A), for actuating the balancer, and sensors for sensing the forces acting on the ligament balancer. The actuators are preferably electric motors, however, any known actuator could be used, including piezo-electric, pneumatic, hydraulic, magnetic/induction, spindle drive and the like. The drive assembly is operable to move the upper paddle relative to the lower paddle. That is, the drive assembly displaces the spacing between the upper and lower paddles under the control of the computer i.e., a controller. In other words, the drive assembly is operable to move one of the upper and lower paddles relative to the other of the upper and lower paddles. The drive assembly is preferably a hermetically sealed drive assembly, as further described below. Alternatively, the drive assembly can be other types of drive assemblies suitable for the intended purpose of the present embodiments, e.g., a hydraulic drive assembly or a balloon drive assembly, as applicable to all or particular embodiments disclosed herein.

As referred to herein, the orthopedic distraction device can include a controller separate from a computer, or a computer functioning as a controller. That is, the functions and capabilities of the present invention described herein can be embodied in a computer separate from a controller or a single controller embodied as a controller.

Figure 2A:
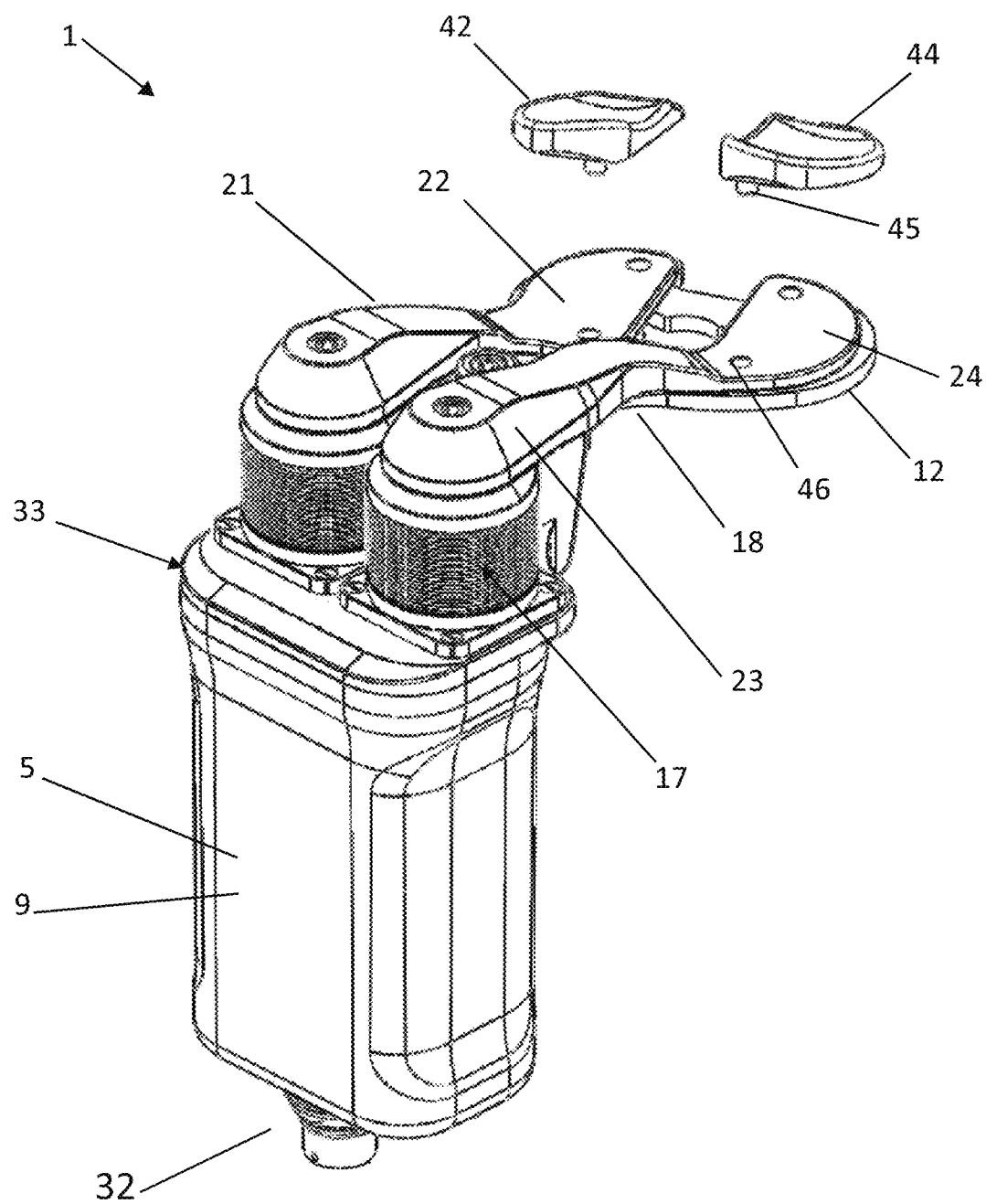
FIGS. 2A-D are various views of an orthopedic distraction device in accordance with a preferred embodiment of the present invention.
Figure 2B:
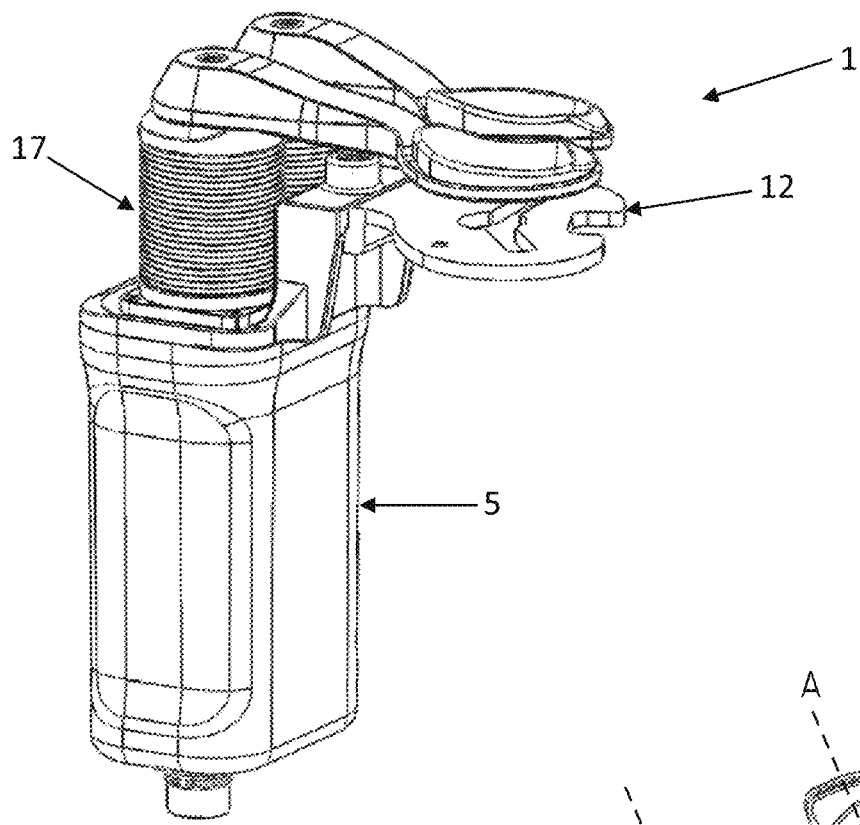

Referring now to FIGS. 2A-E, various views of the ligament balancer 1 are shown. In FIG. 2A, a perspective view of a preferred embodiment of the knee ligament balancer 1 is shown. The ligament balancer 1 includes a displacement mechanism 5, an upper paddle 20 and a lower paddle 12. In accordance with an aspect, the upper paddle 20 can includes a first upper paddle 21 and a second upper paddle 23. The first upper paddle can be a medial upper paddle and the second upper paddle can be a lateral upper paddle. The upper paddle is configured to engage a first bone of a joint and the lower paddle is configured to engage a second bone of the joint.

Figure 2C:
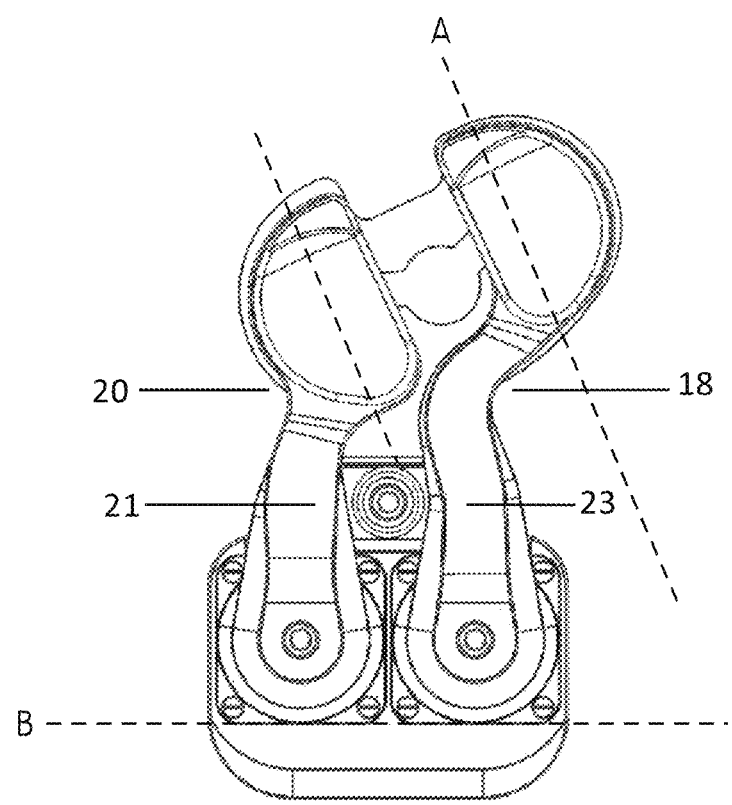
Figure 2D:
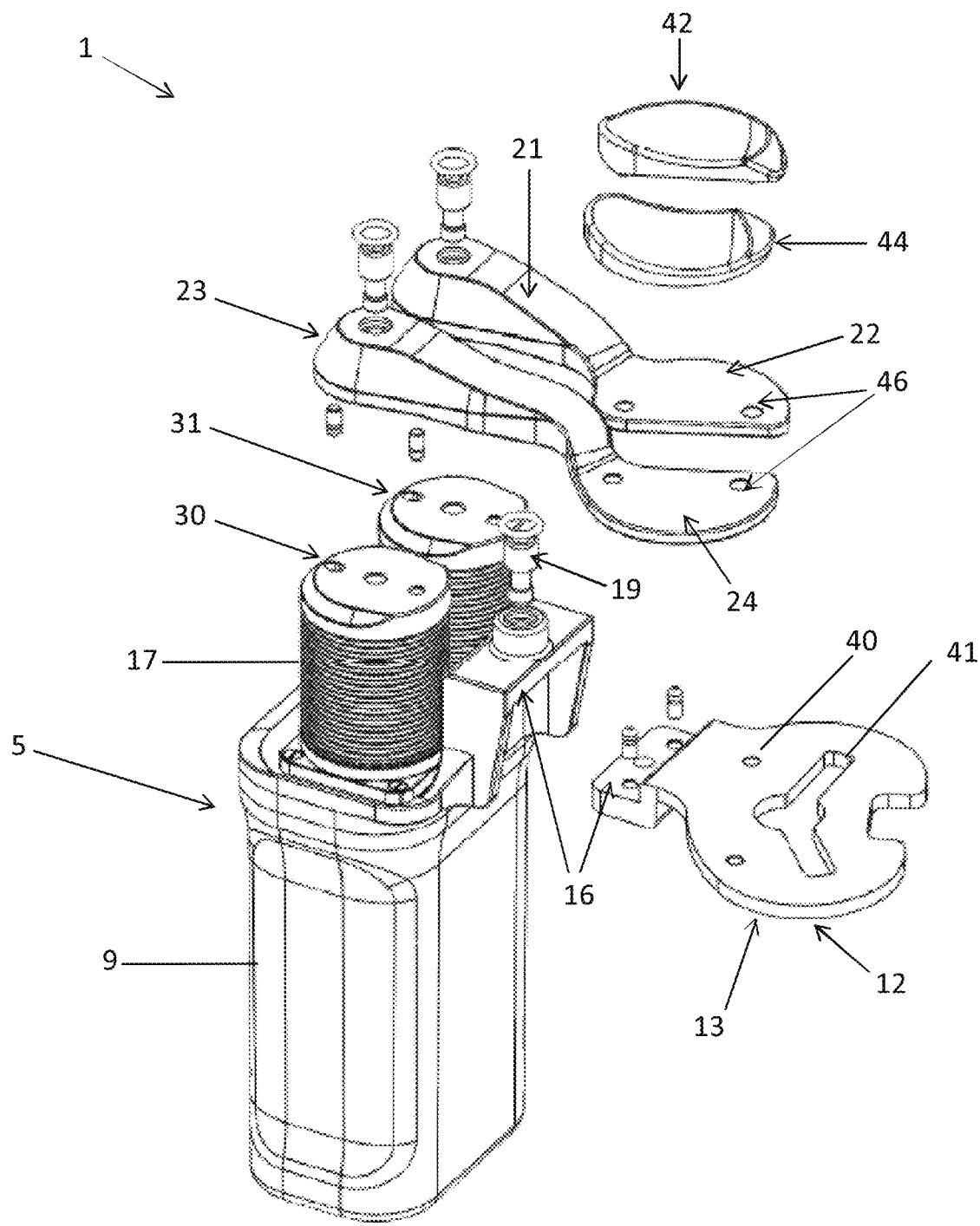
Figure 2E:
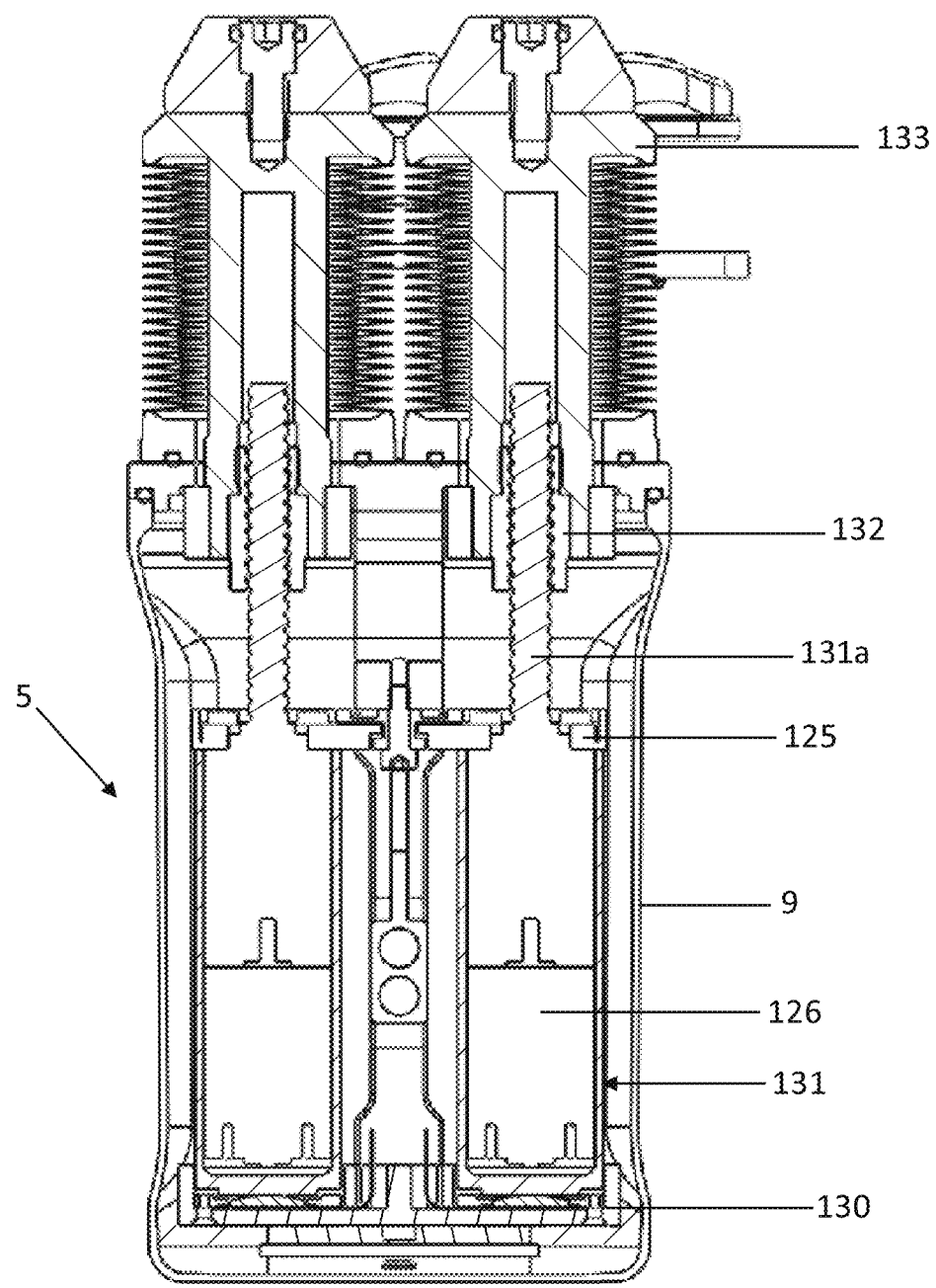
FIG. 2E is a cross-sectional anterior elevation view of the orthopedic distraction device of FIG. 2A.
Figure 2F:
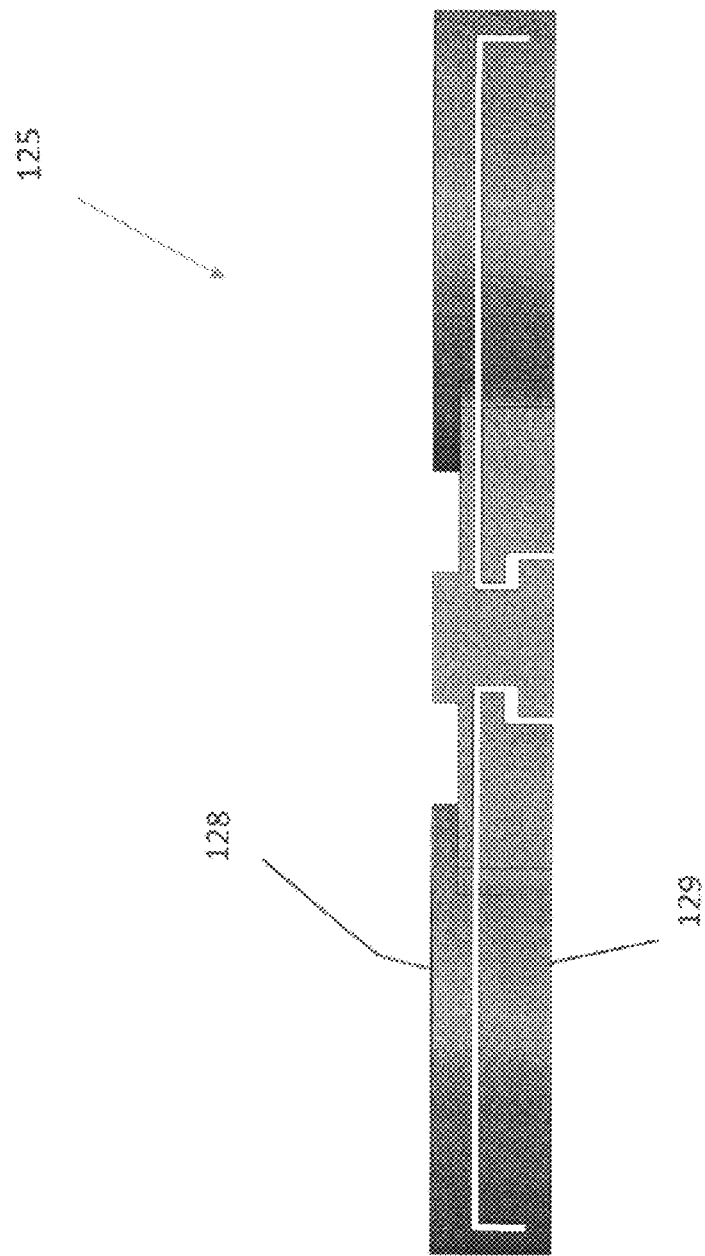
FIGS. 2F and 2G are views of a flexure bracket of the orthopedic distraction device of FIG. 2A.
Figure 2G:
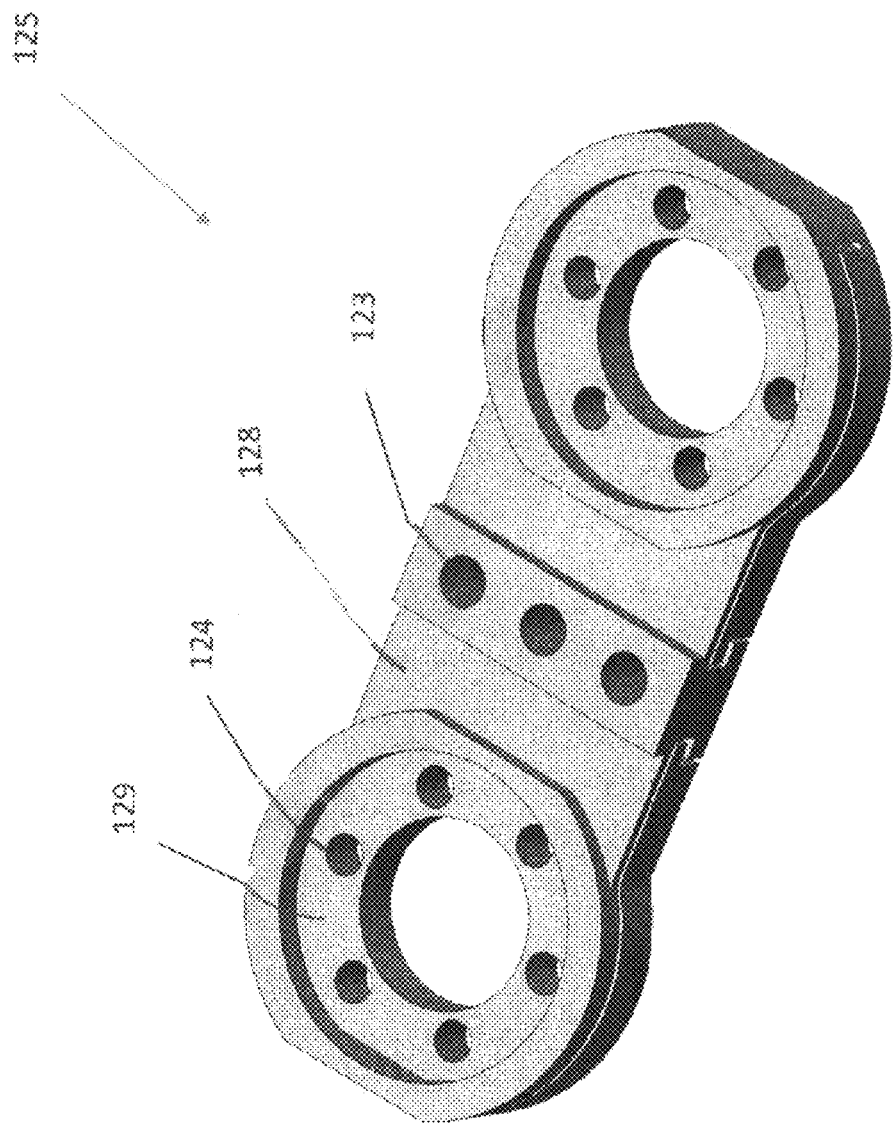
Figure 2H:
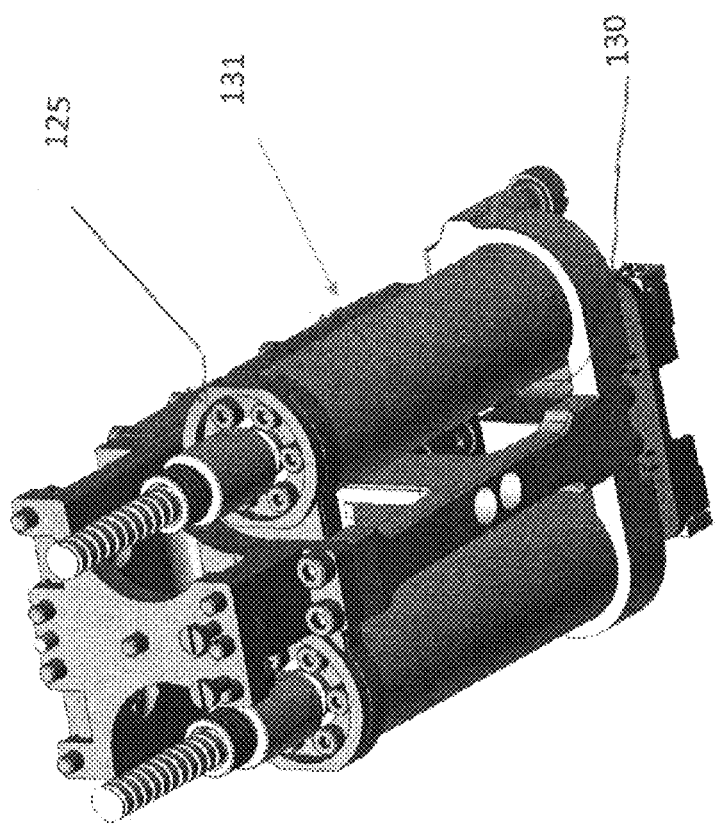
FIG. 2H is perspective view of the orthopedic distraction device of FIG. 2A with parts omitted for purposes of illustration.
Figure 2I:
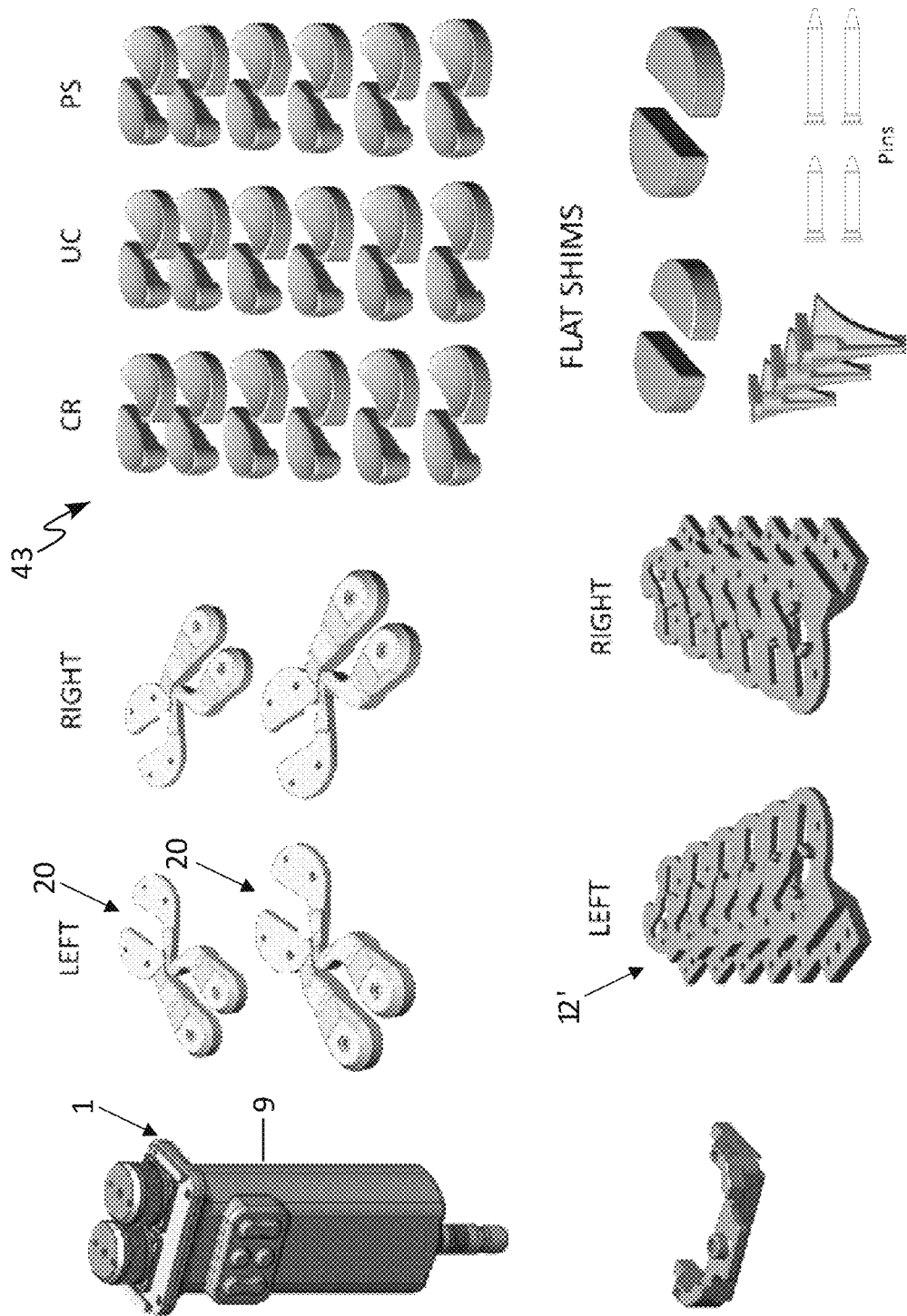
FIG. 2I are views of various components of orthopedic distraction device of FIG. 2A.
Figure 2J:
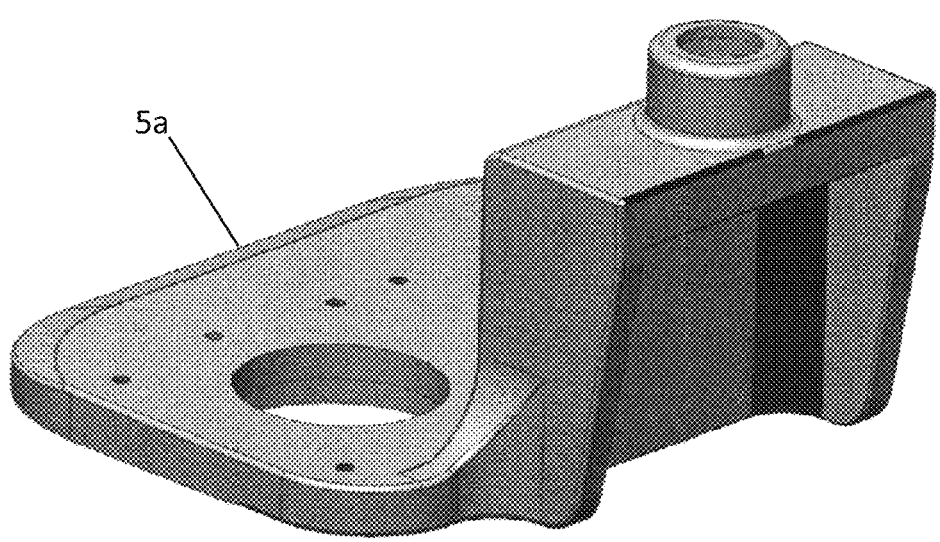
FIGS. 2J-M are various view of internal components of the distraction device of FIG. 2A.
Figure 2K:
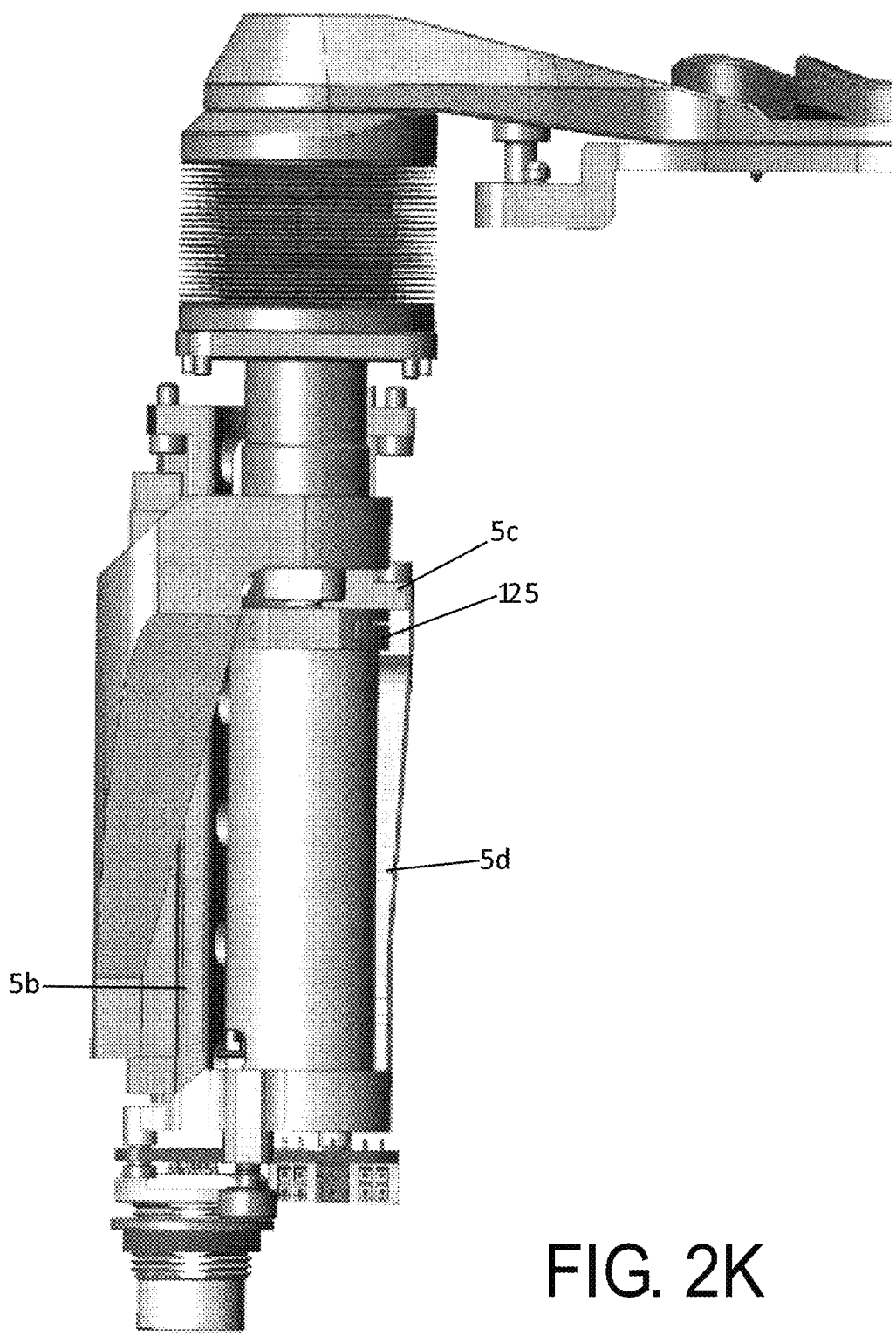
Figure 2L:
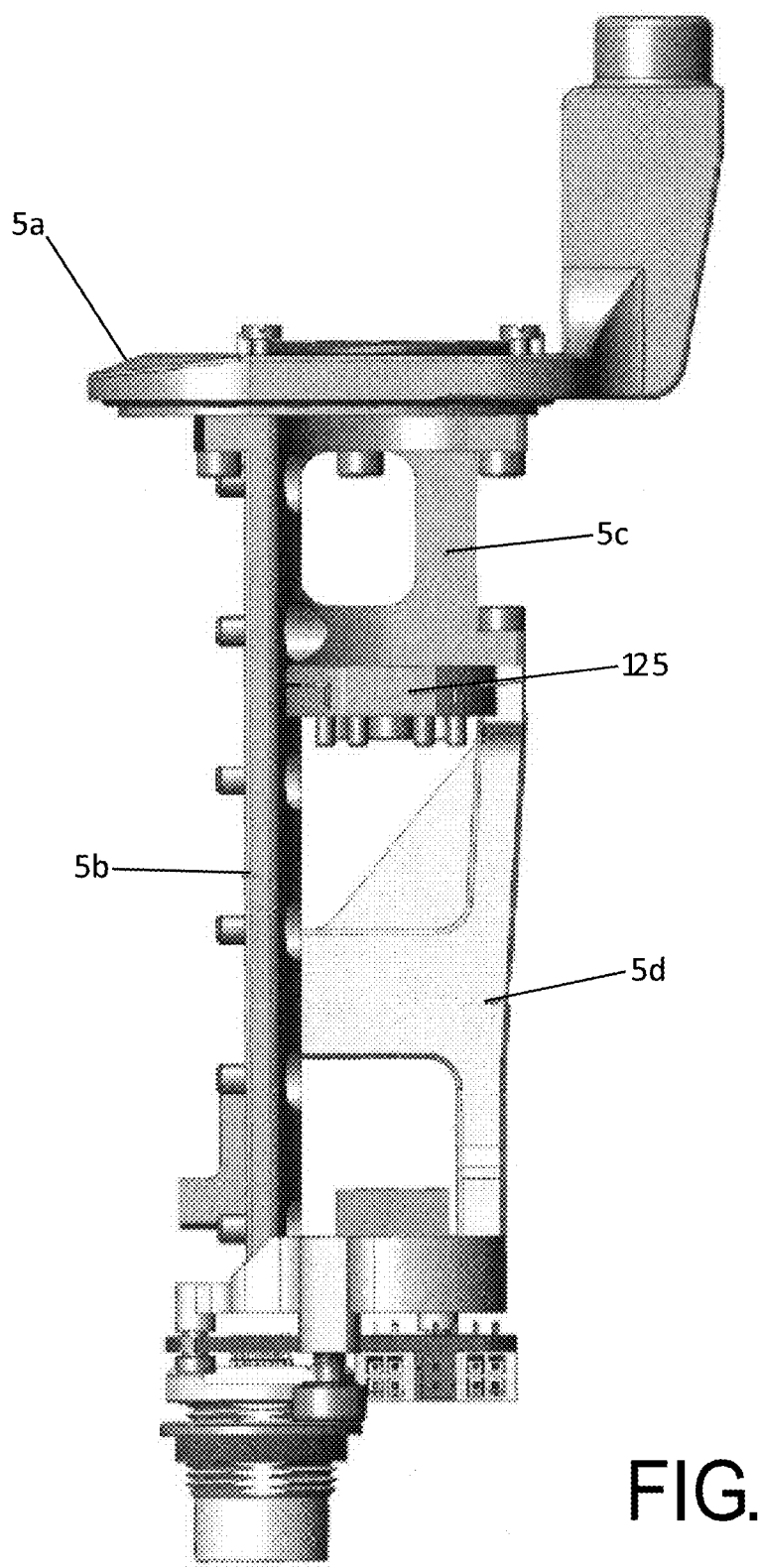
Figure 2M:
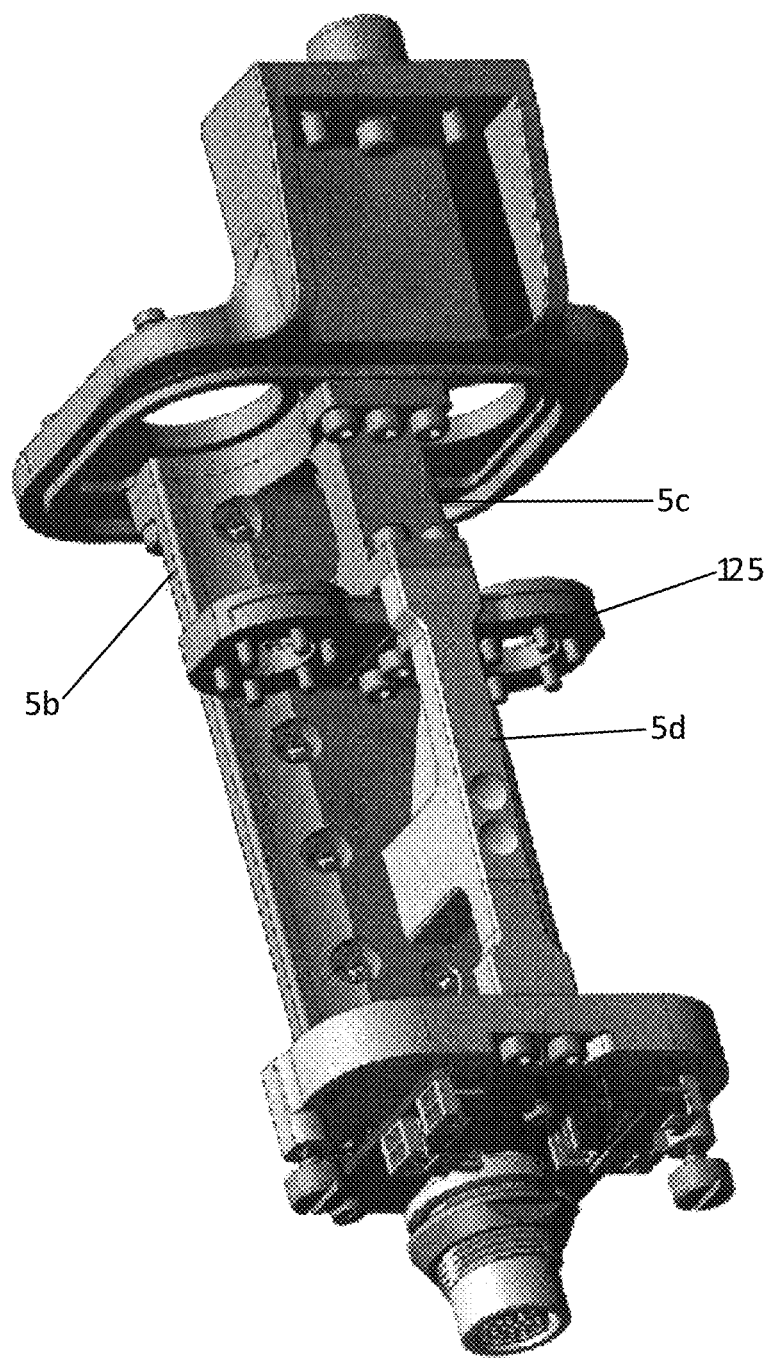
Figure 3A:
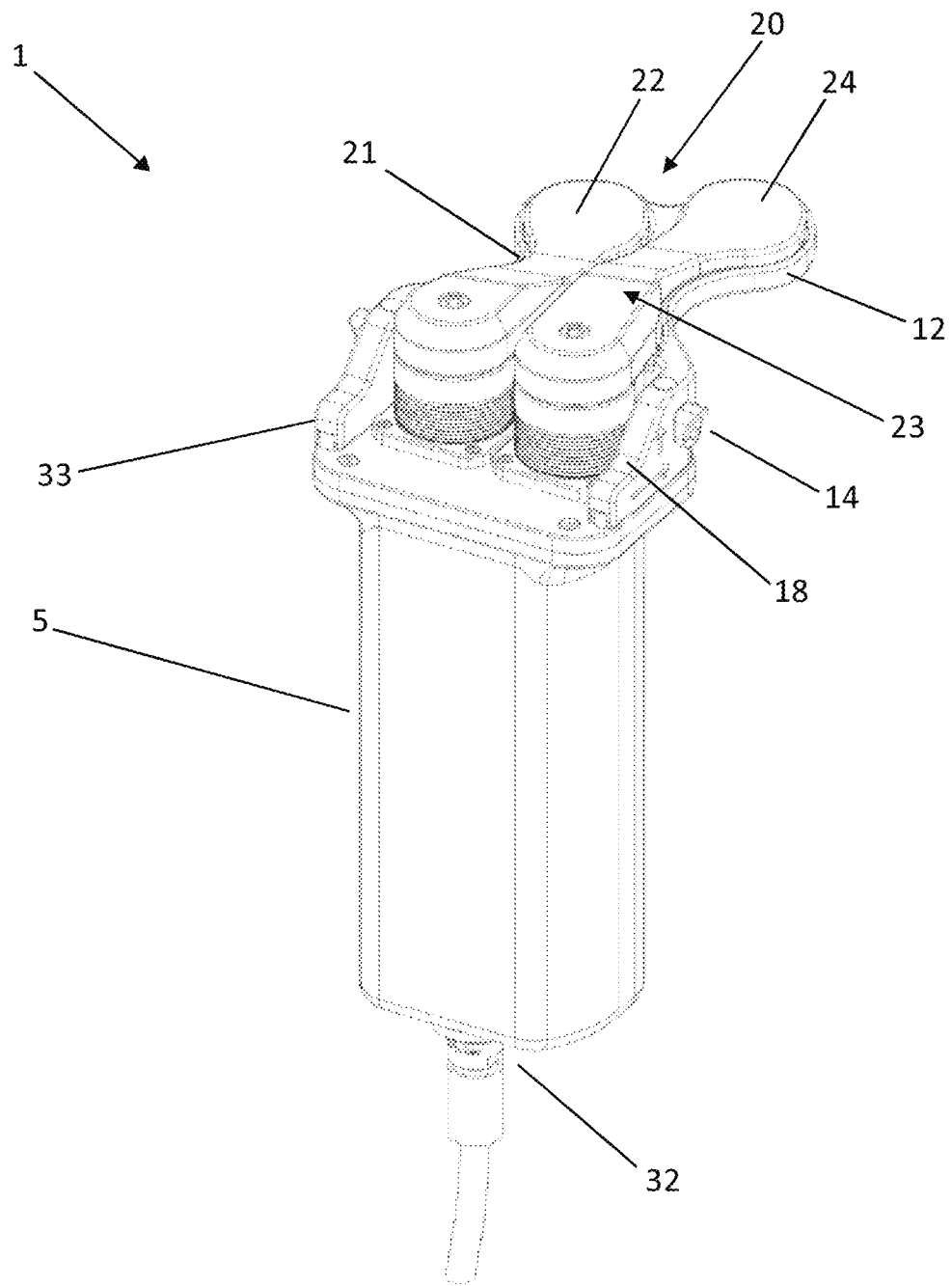
FIGS. 3A-3D are views of an orthopedic distraction device in accordance with another preferred embodiment of the present invention.
Figure 3B:
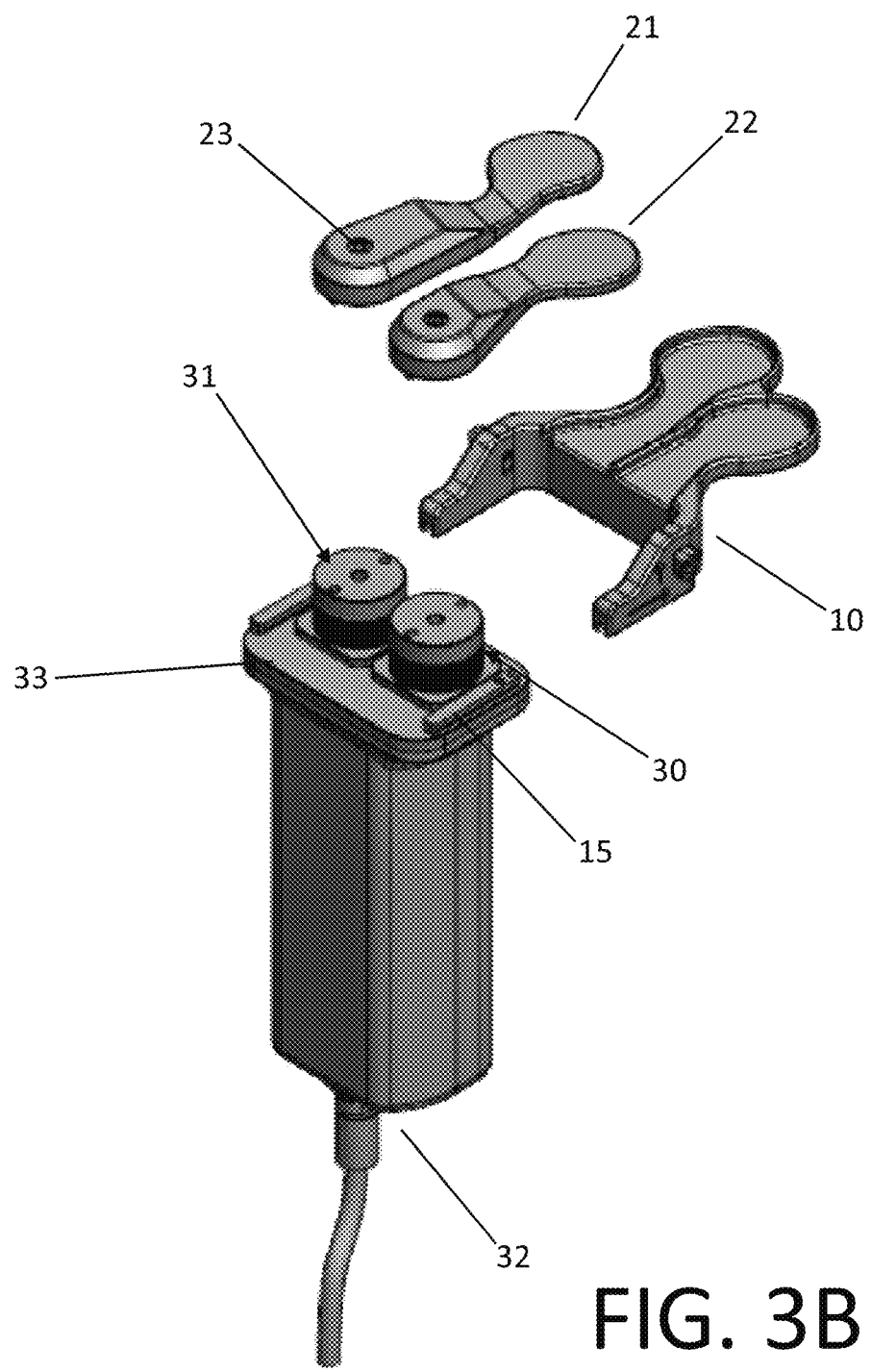
Figure 3C:
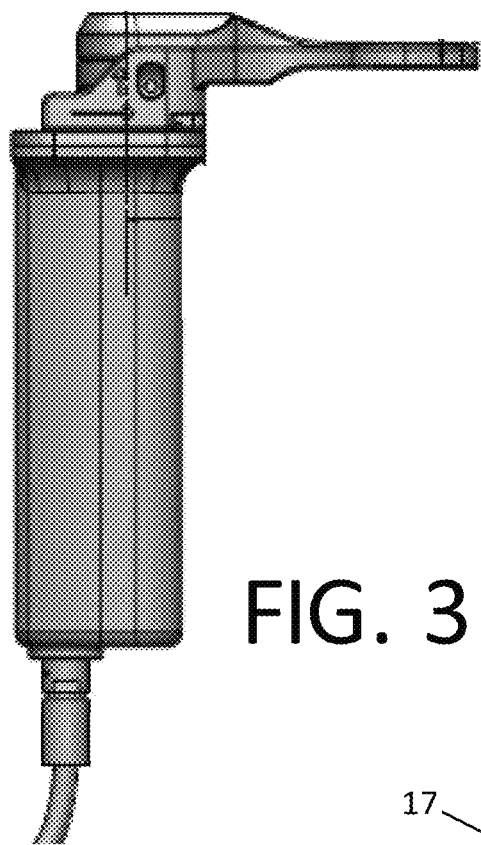
Figure 3D:
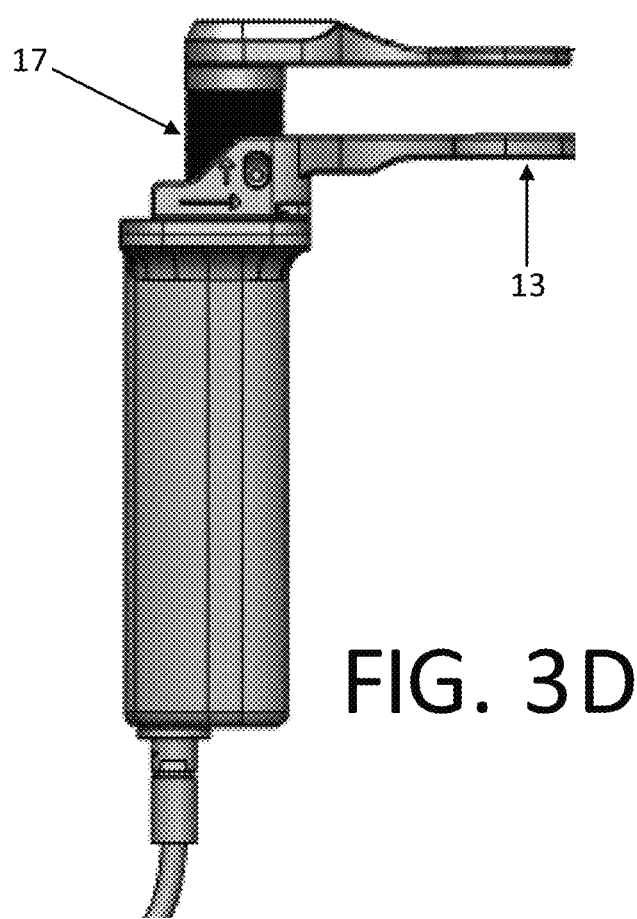

FIGS. 2J-M illustrate various components of the distraction device. FIG. 2J shows a top part 5a of the housing 5. FIGS. 2K-M show the internal structure of the distraction device include the top part 5a, interior chassis 5b connected to the top part, and center supports 5c and 5d, which are all rigidly connected to each other.

Figure 6A:
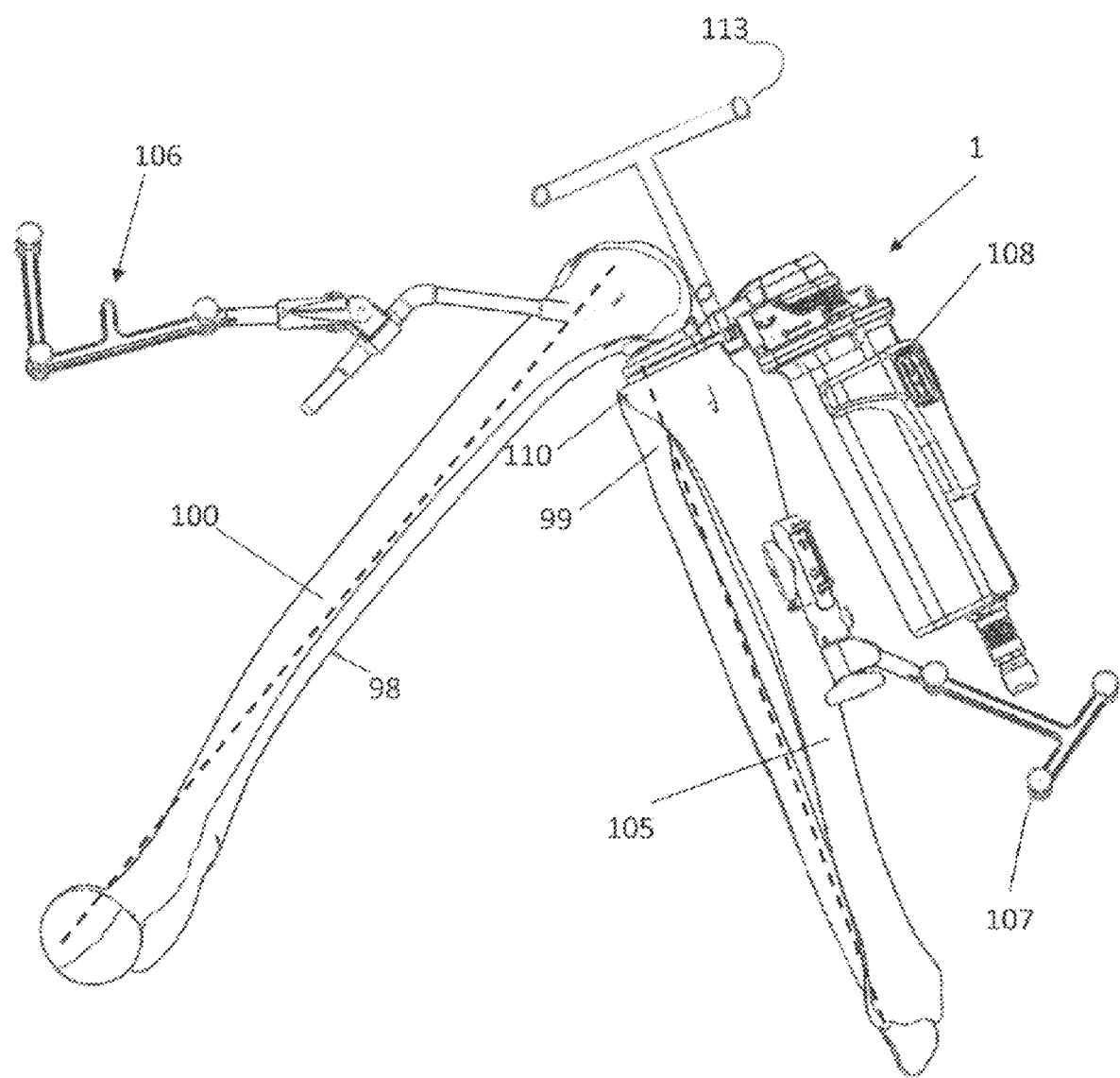
FIGS. 6A and 6B are side and oblique views of the orthopedic distraction device of FIG. 3A inserted in a knee joint in a flexed position.
Figure 6B:
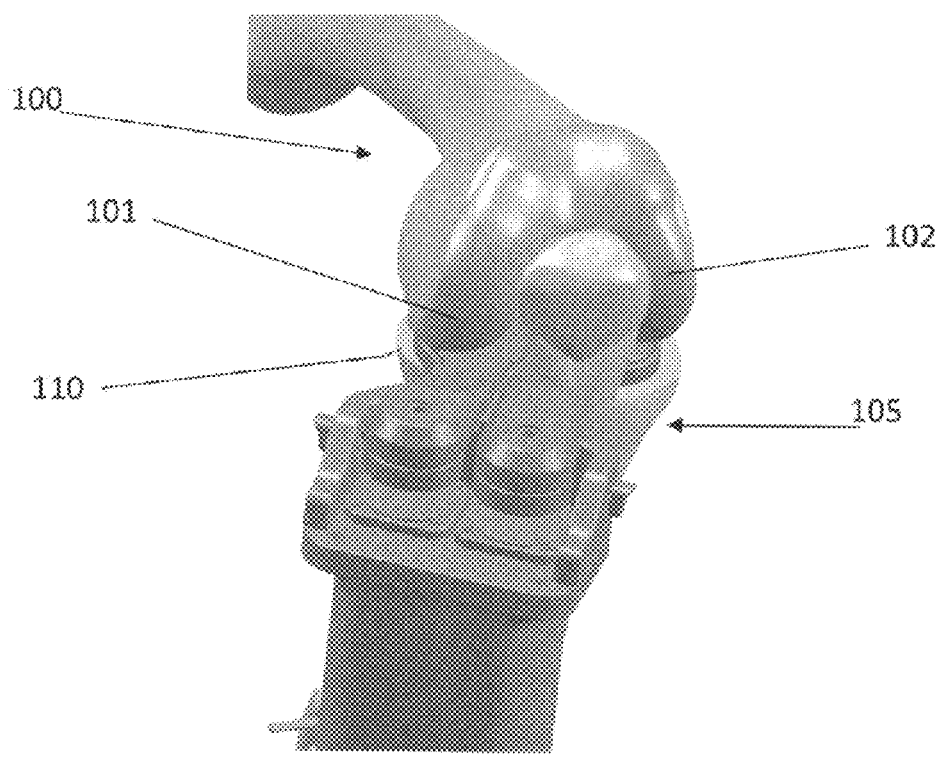

The upper medial and lateral paddles have surfaces 22, 24 that are intended and adapted to contact and articulate with the medial 101 and lateral 102 condyles of a femur 100 (FIGS. 2D and 6A-B). Contact surfaces 22, 24 may be flat or curved/concaved, and may be smooth to allow for sliding of the bone on the paddle contact surface. When augments are attached to the upper paddles, the contact surfaces are below the augments, and preferably directly below the augments.

Figure 16:
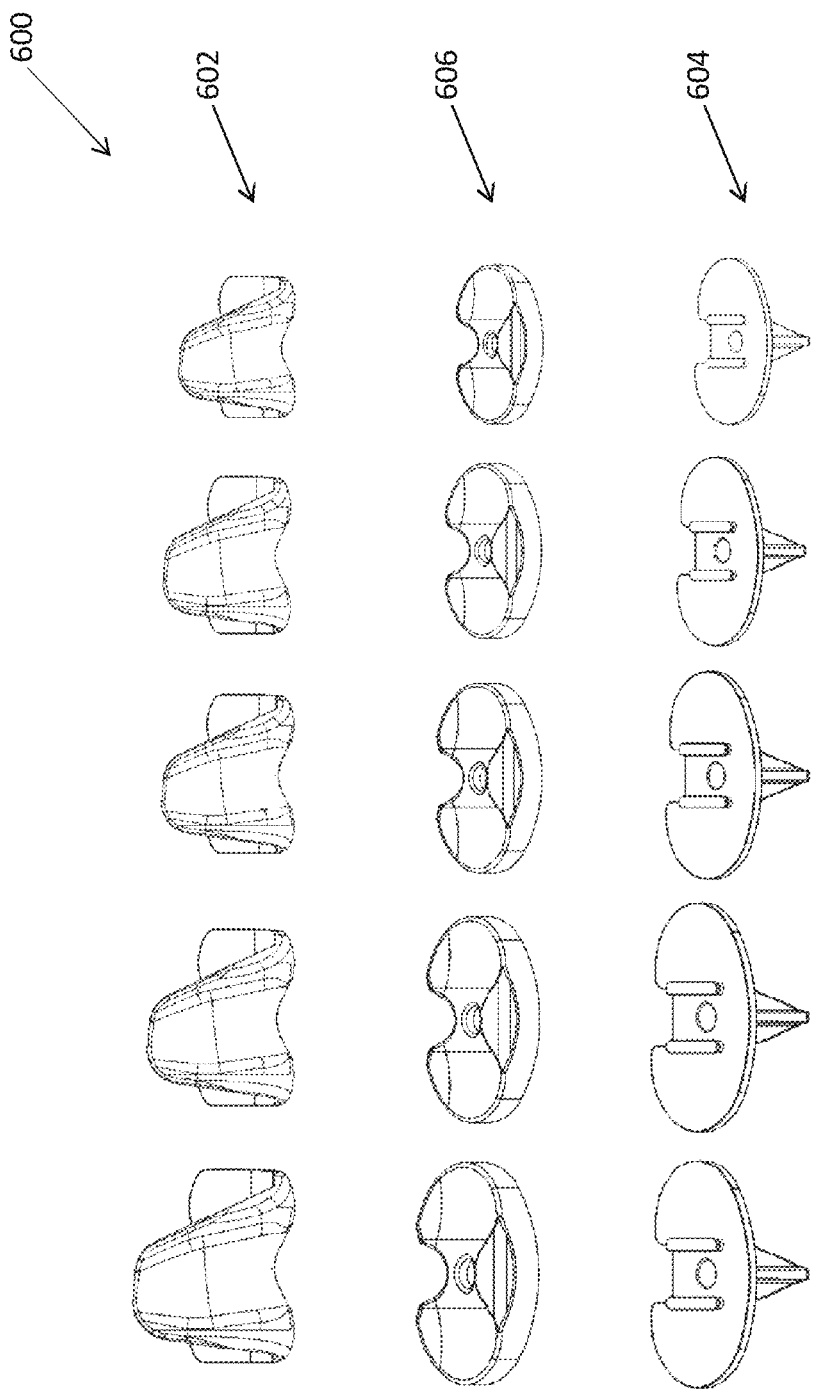
FIG. 16 illustrates a kit in accordance with another preferred embodiment of the present invention.

Referring to FIG. 2I, the ligament balancer can include a plurality of lower paddles of varying sizes and for either the right or left knee. Each of the plurality of lower paddles are sized and shaped to match a respective size and shape of a plurality of implants (e.g., a plurality of tibial implants, as shown in FIG. 16) to be implanted in the tibia e.g., a second bone.

The lower paddle 12 has a surface that is intended to contact the tibia 105. The lower paddle preferably has a lower surface or undersurface 13 (FIG. 2D) that is substantially flat and intended to sit on top of a tibial cut surface 110 (FIG. 6B). The surface 13 can have surface texture or geometric features which help it engage and grip the tibial cut surface, such show generally so that the ligament balancer does not slip on the cut surface during use of the device. In some cases, it is desired that the ligament balancer stay in place in the knee and in particular on the tibial cut during use and during various knee stability tests and motions, which can include varus/valgus stability or stress tests, continuous gap or force acquisitions throughout a range of motion of the joint in a range of flexion angles, heel-push tests, etc., without requiring the surgeon to hold the device in place by hand. To increase the stability of the ligament balances within the knee, the ligament balances could be fixed to the tibia using the lower paddle 12.

As can be seen in FIG. 2D, the ligament balancer is reconfigurable and modular, allowing the attachment and de-attachment of different sets of upper and lower paddles from the displacement mechanism, to permit the use of different sizes and shapes of upper and lower paddles to accommodate the range of patient joint anatomies and sides (right or left). The upper medial and lateral paddles may also have features that allow medial and lateral augments 42, 44 to be attached or easily clipped on them, to augment the height of the paddle, or to provide a differently shaped articulating surface for articulating with the femur or femoral component (implant or trial component). These augments can attach to the paddles using various mating features such as locating pins 45 and holes 46 (FIG. 2A), magnets, quick release clips, and the like. In other words, each of the plurality of augments are releasably connectable to the upper paddle.

The augments are preferably configured with a concave upper surface. These augments can have different levels of curvature or congruency for engaging or mating with a first bone of a joint, e.g., the native femur, or a femoral trial or actual implant once in place. That is, each of the plurality of augments is configured to articulate with the first bone (e.g., femur) or a femoral trial implant. In particular, an array of different sized augments can be provided to match the radii of curvature of the various sizes of tibial and femoral implants provided with the implant system. Preferably a range of different sizes of augments are provided so that each size in the range matches the size and shape of each tibial insert trial implant or each tibial insert implant in the range offered in the implant system that is to be implanted in the patient. The spacing between the medial augment and the lateral augment is such that when they are mounted on their respective medial and lateral upper paddles, they match the spacing of the medial and lateral plateaus or dishes of the tibial insert implant to be implanted.

As shown in FIG. 2D, the ligament balancer includes an attachment interface 16 for attaching the lower paddle 12 to the displacement mechanism. The attachment interface can include any type of coupling means, such as fasteners, one or multiple screws 19, locating pins and holes, magnets, quick release clip mechanisms, and the like. As such, the lower paddle 12 is releasably connected (i.e., connectable) to the displacement mechanism 9.

Figure 11A:
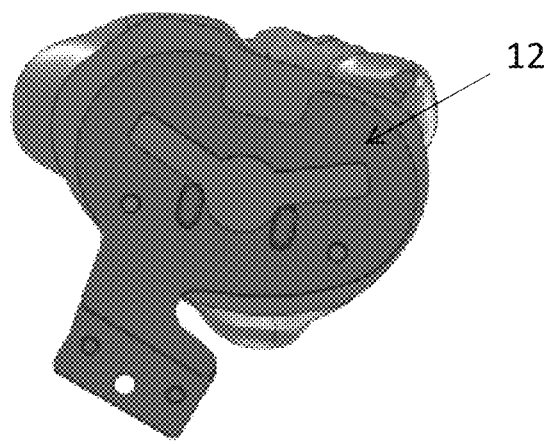
FIGS. 11A-F are in sequence views showing the operation of the lower paddle of the distraction device of FIG. 2A being fixed to a tibia.

Preferably, the ligament balancer comes with a range of different size lower paddles 12, wherein each size in the range of lower paddle sizes matches the corresponding size (profile, shape, medial-lateral size, anterior-posterior size, and/or thickness) of the tibial baseplate of the implant system being implanted. As shown in FIG. 11A, the lower paddle 12 can also be used as a template for the surgeon to place on the tibial bone cut in order to determine the optimal size, position and/or rotation of the tibial implant baseplate to use for that patient. Thus the lower paddle can be placed on the tibial cut surface (attached or detached from the ligament balancer), and because the lower paddle matches the sizes and shape (or profile) of the tibial implant, the surgeon can select the size and rotate and position the lower paddle on the tibial cut surface so that the outer contour of the lower paddle 12 best matches the contour of the bone resection 110.

Figure 11B:
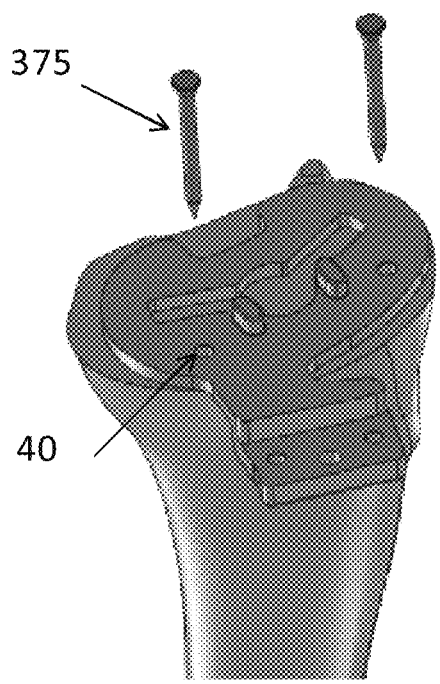

The lower paddle 12 may also include features and fasteners for fastening the paddle to the tibial resection of e.g., a second bone, such as holes 40 for receiving bone pins 375 (FIG. 11B) or screws. The lower paddle 12 may also include features such as openings or apertures, such as a fastener opening 40 and a keel opening 41, and guide members e.g., guide-holes or pegs 364 for receiving/guiding a keel punch 365 or other cutting or drilling tool, for creating a cavity 366 for the keel or stem of the tibial implant. The fastener and keel openings are configured to receive a corresponding keel punch and fastener. The feature or pegs 364 for guiding the tool for creating the tibial keel or stem cavity 366 is preferably positioned on the lower paddle 12 such that when the tibial keel or stem cavity 366 is created, the positon of the final tibial implant will match the position of the lower paddle 12 when the cavity was created. As shown in FIGS. 11C-F, once the cavity 366 for the implant keel is created, a temporary plug 367 may be inserted (FIGS. 11D and 11E) into the cavity 366 to fix the lower paddle 12 to the tibia. This can be used to supplement the pin 375 fixation, or instead of the pin fixation. Using the plug instead of the pins has the advantage of minimizing the amount of holes placed in the bone, reducing invasiveness, since the cavity for the keel needs to be created regardless. The ligament balancer may be attached to the lower paddle either before or after (FIG. 11F) the lower paddle is fixed to the tibia. The ligament balancer may also be attached to the tibia, or to a leg positioner, using straps.

In another embodiment, the under surface 13 of the lower paddle is smooth to allow for rotation of the ligament balancer on the tibial cut surface during a range of knee motion from flexion to extension, or from extension to flexion.

The ligament balancer with lower paddle attached, or the lower paddle by itself, can be tracked relative to the bone, by attaching a reference marker 113 to it tracking it relative to the bone. The lower paddle 12 can be navigated into position using the bone model and software that allows the surgeon to plan the position of the implant and the resection on the bone. The knee joint may also be taken through a range of motion with the tracked ligament balancer in the knee, and the position of the ligament balancer relative to the femur and tibia may be tracked during this range of motion.

Because the computer 4 is able to control the height or spacing of each upper paddle relative to the lower paddle of the ligament balancer (i.e., the space between the upper paddles and the baseplate), by clipping on a specific augment size and baseplate size, and by controlling the height according to the desired thickness of the insert, any implant size and thickness offered in the implant system can be constructed, simulated, and trialed in the joint, without having to make available each of the individual tibial implant sizes and thicknesses in the operating room. Since conventional instruments usually include one trial instrument for each implant in the range of available implant sizes and thicknesses, an advantage of the present invention is thus a reduction in the total number of instruments required to be provided in the OR.

As shown in FIG. 2C, the upper medial 21 and lateral 23 paddles can be different shapes with respect to one another. For example, to facilitate a medial approach to the knee joint, the medial paddle 21 may be shorter in length and the lateral paddle 23 may be longer to reach the far lateral side. That is, the first upper paddle (shown as paddle 23 in FIG. 2C) extends further from the displacement mechanism than the second upper paddle (shown as paddle 21 in FIG. 2C).

The upper paddle arms may also have curved profiles to avoid impingement with the soft tissue around the knee. Particularly, the profile of the lateral arm may by curved or have a concave relief i.e., an inwardly extending relief for clearance 18 to avoid impingement with the patellar tendon and lateral displacement of the patella (FIG. 6B) when the ligament balancer is inserted in the knee and when the knee is brought into different flexion angles. That is, one of the first and second upper paddles includes an inwardly extending relief for clearance of such ligaments, tendons or other tissue. Similarly the medial arm may have a curved, concaved surface/relief 20 to prevent impingement with the medial collateral ligament and other medial tissues surrounding the knee. Different paddles can be provided for a left or a right knee. For example, FIG. 2C illustrates upper paddles configured for use with a left knee, while a mirror image configuration of the upper paddles can be used for a right knee.

Referring to FIG. 2C, owing to the angle at which the augments are aligned and attached to the upper paddles, a longitudinal axis of the augments (A) extends at a non-perpendicular and non-parallel angle relative to a coronal plane (B) of the displacement mechanism.

Alternatively, the paddles can be designed such that they can be swapped or interchanged from the left 31 and right 30 paddle connectors (FIG. 2D) so that the same paddles can be used for a left or right knee (i.e., the shorter paddle can be used as the medial paddle, for both a left knee and a right knee, and the longer paddle can be used as the lateral paddle, for both a left knee and right knee). This can be accomplished by making the paddles symmetric, or changing the side each paddle mounts on the displacement mechanisms and the angle at which it mounts on with respect to the long axis of the device (i.e., flipping each paddle upside down). Shorter and longer paddles can be provided for smaller and larger (i.e., obese) patients. Similarly, paddles that have a wider and narrower overall mediolateral dimension when assembled on the ligament balancer can be provided to fit wider or narrower femurs and tibias and to simulate smaller and larger tibial implant sizes. The paddle connectors are attached to the bellows shaft and thus move relative to the drive mechanism or drive assembly.

The paddle connectors 30, 31 may include features for coupling the upper paddles in multiple positions with respect to the displacement mechanism, such as multiple holes or slots for accommodating the same locating pin so that the upper and lower paddles can be mounted on the connectors such that they are further apart from one another in the medial-lateral direction, or so that they extend shorter or longer into the joint. By allowing multiple positions of attachment for each paddle, it is not necessary to provide different paddles for fitting different sizes of knees or for simulating smaller and larger sizes of tibial trials and implants. The user simply has to assemble the device so that the appropriate locating pin is in the appropriately positioned hole or slot for simulating the desired size of knee or tibial insert trial or implant. The paddle connectors are also hermetically enclosed by bellows.

In accordance with another embodiment, the orthopedic distraction device can be configured with the lower paddle 12 is connected to the displacement mechanism using a quick disconnect system 10, as shown in FIGS. 3A-3D. Buttons 14 (FIG. 3A) on either side of the lower paddle release the lower plate from the body, by using a dove tail or T-slot sliding rails 15 (FIG. 3B) with an axial catch that is released when the button is pressed. Buttons 14 can be provided on one or both sides of the device to allow for the quick and ergonomic release of the lower paddle.

Sealing

Figure 4A:
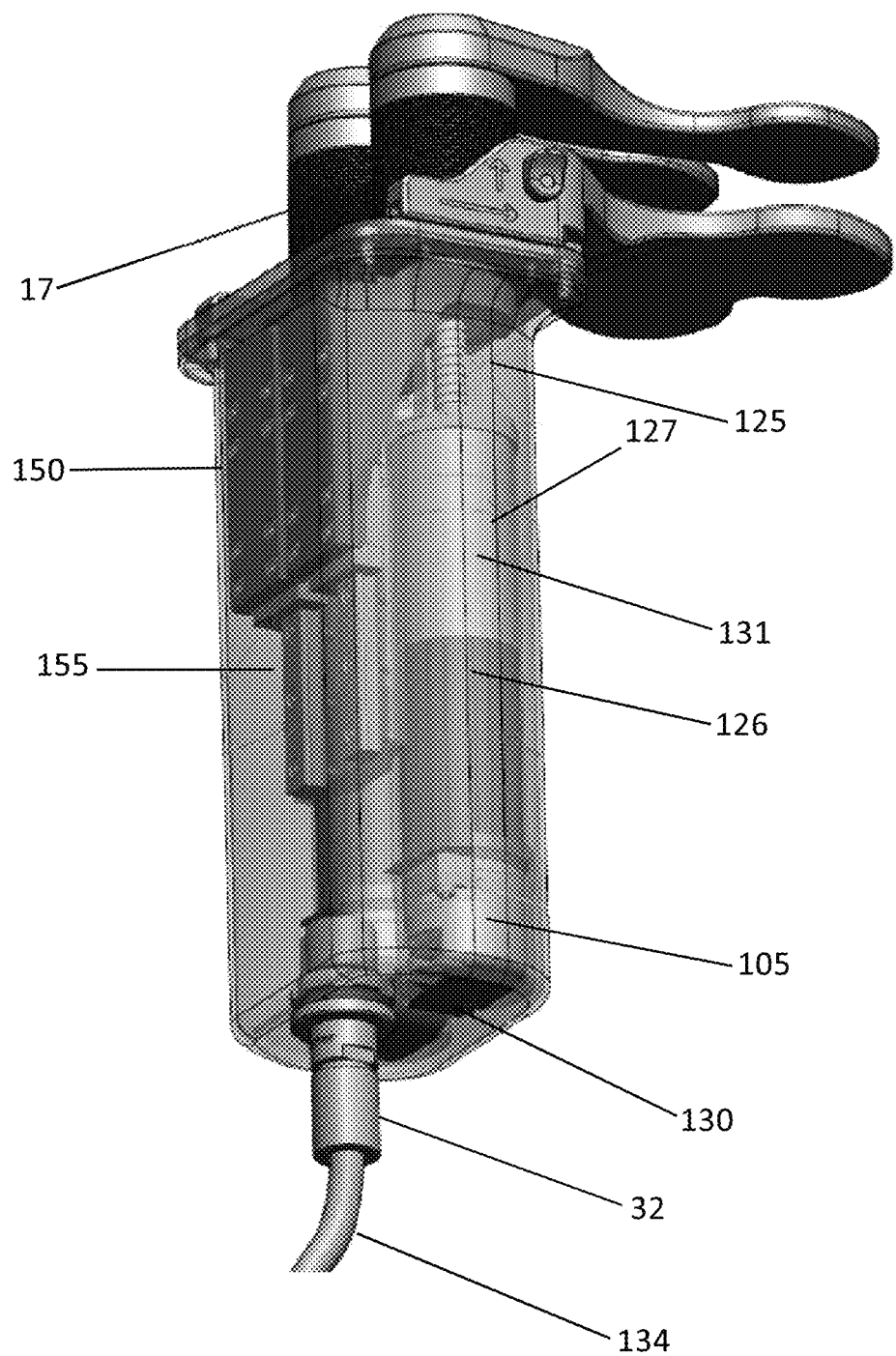
FIGS. 4A and 4B are perspective views showing the internal components of the orthopedic distraction device of FIGS. 2A and 3A, respectively.
Figure 4B:
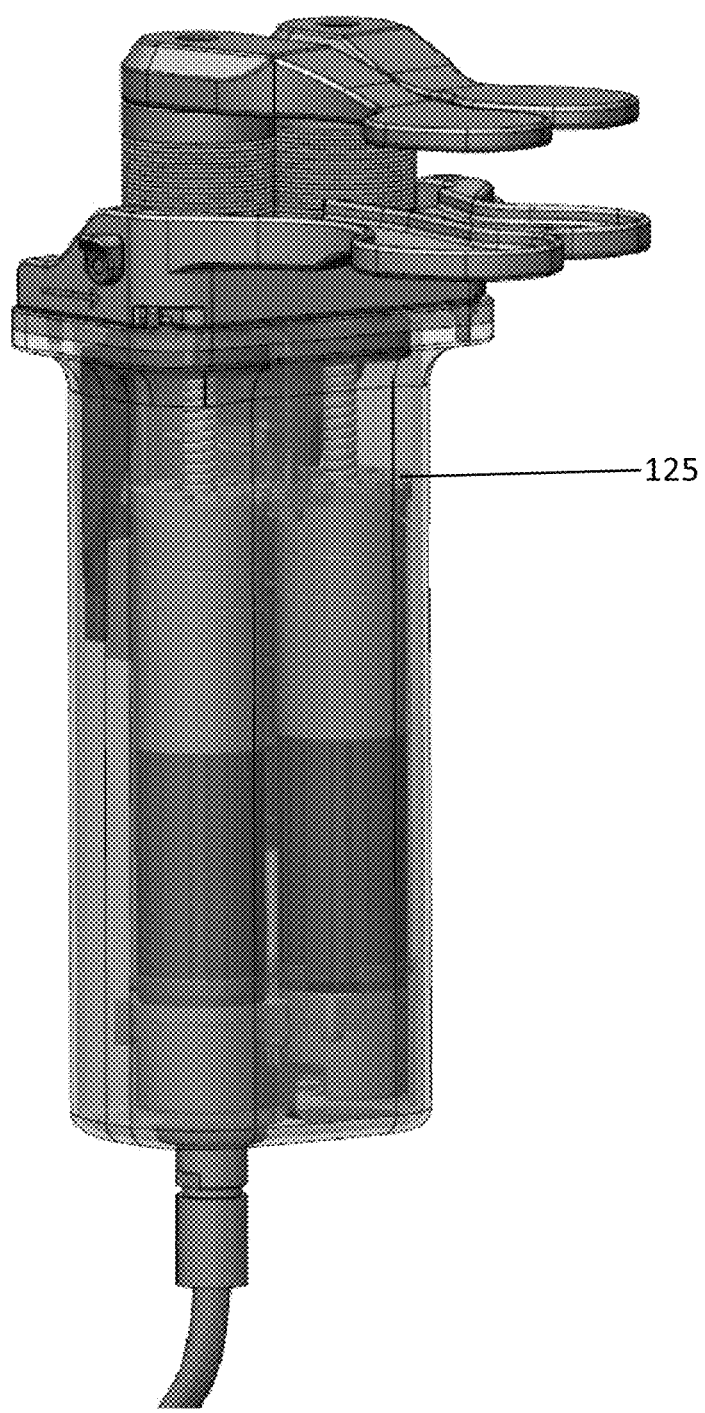

Referring back to FIGS. 2A-E, the displacement mechanism 5 includes a housing or body 9 that forms an enclosure that is preferably sealed, and more preferably hermitically sealed. O-ring and other seals can be provided as static seals at the cable connector 32 and at the upper part 33 of the body which provides access into the main body. The linear axes of the paddle connecters are preferably sealed by the use of bellows 17 of a bellows assembly, which allow the linear motion (expansion and contraction) of the paddles with respect to the displacement mechanism and the lower paddle, while maintaining a complete seal of the displacement device. Thus, the bellows assembly provides for hermetically sealing the drive assembly to the displacement mechanism. For example, the bellows assembly is connected to the upper paddle and drive assembly thus forming a sealed enclosure, as shown in FIG. 4A.

The bellows assembly includes bellows 17 and a bellows shaft 133. One end of the bellows is connected to a top end of the bellows shaft and an opposite end is connected to the housing 5, e.g., a top end of the housing. The bottom end of the bellows shaft 133 is connected to a ball-screw bearing 132, and preferably rigidly connected to an outer surface of the ball-screw bearing. The bellows assembly is moveable relative to the drive assembly 131

By expansion and contraction of the bellows assembly along the axis of the bellows, the paddles can move up and down (or further or closer to the lower paddle) along the same axes while the ligament balancer maintains a sealed state. This allows the body 9 to be washed and cleaned and sterilized in an autoclave, and will prevent steam vapor or cleaning agents from entering inside the device and affecting the function and performance of the internal mechanisms. It also prevents any contaminates from coming out of the displacement mechanism and infecting the patient or compromising the sterile field.

The bellows 17 can be metal and manufactured with precision welding or laser welding operations. Metal bellows provide greater durability. Alternatively, the bellows can be made out of plastic and could be injection molded to reduce costs.

The bellows assembly includes paddle connectors 30, 31 which may include flanges or other features to make it easier for a user to grip the connectors and pull them up and expand the bellows 17 when the upper paddles are attached. This would facilitate access to the outer surfaces of the bellows for cleaning of the ligament balancer after use in surgery.

Motion

The CAOS system 1000 includes components that allow for active motion and control of the displacement device 1. Referring now to FIG. 4A, a view of the ligament balancer is shown with a transparent body 9. The components that allow for active motion include a drive assembly 131 having motors 126, gear heads such as planetary gear heads 127, and ball screws. The ball screw and linear guide, which includes rails 155 and carriages 150, translate the rotatory motion of the motors 126 and gears 127 into linear motion of the carriages 150, which are connected to the paddle connectors 31, 30, which are in turn connected to the upper paddles 21, 23. The motors can have hall sensors (otherwise known as hall-effect sensors) that control the communication of the electrical signals and power to the motor windings. The system may also include an encoder 105 to monitor the rotational position of the motor.

The drive assembly 131 also includes a plunger 131*a* operatively driven by the motor 126. The plunger can be a spindle or threaded plunger. Operation of the motor 126 rotates the plunger, which in turn engages a ball-screw bearing 132. The ball-screw bearing is connected to rails 155 and carriage 150 that supports the bellows assemblies and paddle connectors. Thus, the bellows assembly translates in an axial direction due to the rotation of the plunger 131*a*.

The drive assembly is controlled by the controller 4, which is configured to apply a first displacement force to a first upper paddle (e.g., a medial upper paddle) and a second displacement force to a second upper paddle (e.g., a lateral upper paddle). The second displacement force can differ from the first displacement force. In other words, the displacement mechanism is configured to independently displace or apply a displacement force to each of the first and second upper paddles.

Alternatively, the hall sensors can be used to monitor the rotational position of the motors. Either encoders or hall sensors can be used for monitoring the position of the motors and thus can be used for controlling the position of the motors and, through the transmission system (i.e., the gears, ball screws, and sliders), the paddles.

Alternatively, the analogue power channels (lines) from the controller to the motor that are used to power each individual motor winding can be used to provide information on the rotational position of the motors. In particular, the relative phase and the sinusoidal shape of each channel (line) that powers the motor windings can be used to estimate the rotational position of the motors. This has the advantage of a sensorless motor control approach which requires fewer wires and thus simpler cables and hardware components. The motors can be powered with a power supply that is connected to the main network power, where the power supply is connected to the ligament balancer via the controllers 3, a cable 134 and cable connector 32, or the motors may be battery powered so that a cable is not required, allowing for wireless capabilities. The motor controllers can be integrated into the displacement mechanism of the ligament balancer to allow for wireless control, where command signals are sent from an emitter connected to the computer, wirelessly through the air via the electromagnetic spectrum, to a receiver and the integrated controllers into the ligament balancer.

Any type of wireless communication protocol and communication hardware may be used. To facilitate accurate and controlled motion of the ligament balancer 1, the ligament balancer may be homed either before or after it is assembled, or at any time during the procedure. Homing shall mean correlating the rotational position of the motors to the linear position of the upper and lower paddles, such that the positional relationship between these two is known. Homing the ligament balancer may be accomplished by automatically moving the upper paddles down until they come into contact with the lower paddle while measuring the position of the motors, thus determining a reference or zero position. During the homing sequence, current to the motors may be monitored or limited, or the force sensors (described below) may be used, to reduce or limit the force the device may apply during the homing motion, thus preventing any pinch hazards for an operator's fingers or the patient's soft-tissues.

Force Sensors

The ligament balancer 1 also includes force or load sensors 130 to measure the loads acting on each of the paddles. These sensors can be force sensing resistors, or any other sensor technology known in the art, such as piezo-electric, piezoresistive, strain-gage based, thin or think film sensors, capacitive wave-guide technology, and the like.

The force sensors are preferably mounted in the sealed body 9 of the displacement mechanism 5 to shield them from the environment during cleaning, sterilization and use during in surgery. They can be mounted under the motors or drive assembly at the base of the body such that when a load is applied at the paddles, the force is transferred through the bodies of the bellows assembly and drive assembly e.g., linear guides, ball screws, gears, motors and encoders. In other words, the sensors are positioned within the housing and below the drive assembly.

The displacement mechanism further includes a flexure motors bracket or flexure bracket 125 (FIGS. 2E, 2F, 2G and 2H) used to rotationally fix or constrain the two motors relative to each other, and/or relative to the housing body 9 and other internal components of the displacement mechanism, while still allowing axial force to be transmitted through the flexure bracket to the force sensors 130 underneath the motors at the base of the body. The flexure bracket 125 is designed to allow for some flexion of the bracket, to allow for some small axial motion of the motors relative to the body, while rotationally constraining the motor and gear housings to allow the motors to transmit torque to ball-screw bearings 132 and output shafts or bellows shaft 133. Thus the force sensors are axially positioned under the motors and are subjected to the forces acting on the paddles by virtue of the flexing of the flexure bracket 125.

The flexure 125 is configured as best shown in FIGS. 2F and 2G, and includes a rigid portion 128 and a flexure portion 129. The flexure shown in the present embodiment is configured to support two separate drive assemblies, but can alternatively be configured to support a single drive assembly, or more than two drive assemblies, or formed as two separate flexure brackets, each one configured to support an individual drive assembly. The rigid portion 128 is fixedly mounted to the housing 9 of the displacement mechanism 5. For example, the rigid portion can be fixed to the housing by fasteners extending through apertures 123, which can be aligned to corresponding apertures on the housing.

The drive assembly is mounted to the flexure portion 129 via fasteners, as best shown in FIG. 2H. The flexure portion includes apertures 124 for receiving said fasteners. Preferably, a top most portion of the drive assembly is mounted to the underside of the flexure portion. Thus, owing to the flexure design of the flexure bracket, as best shown in FIG. 2F the flexure bracket allows for movement (e.g., minor movement due to deflection of the flexure portion) of the attached drive assembly relative to the rigid portion in at least one direction e.g., an axial direction. In other words, the drive assembly is axially movable between a first position and a second position spaced from the first position.

In sum, the displacement mechanism includes a housing body and flexure bracket connected to the housing body. The flexure secures the drive assembly within the housing body, thus allowing the drive assembly to move between a first position and a second position spaced from the first position, e.g., axially spaced. Further, owing to the positioning of the sensor within the housing, the drive assembly engages the sensor in both the first and second positions. That is, when the drive assembly axially moves between the first and second positions, it maintains its engagement with the sensor at all time.

The force sensors 130 are configured to generate an electrical signal that is transmitted to the computer 4 and controllers 3 that is indicative of the force acting on the sensor and paddles. The electrical signal may be amplified by an amplifier and converted from an analogue signal to a digital signal via an analogue to digital (A2D) converter. The force signals can be transmitted wirelessly or by wire. In order to improve the force sensing resolution of the system, two force sensors can be used on either side of the balancer, where one sensor is optimized to read forces in one range (for example 0-150 N) and the second sensor is designed to read forces in a second range (e.g., 100-500 N). This way, the appropriate sensor may be read depending on what range the force is, providing a more accurate measurement and also providing some redundancy in the system to better detect faults and malfunctions. The sensors may be stacked, with intermediate members in between them, such as a smooth shim, to provide optimal sensing surface on both sides of each sensor.

The controller 4, which is operatively in communication with the displacement mechanism, is configured to move the displacement mechanism to receive a predetermined load force. The predetermined load force can be entered and stored in the controller and set to a particular user preference. The controller can also be configured to measure the load force applied to at least one of the medial upper paddle and lateral upper paddle. Additionally, the controller can be configured to apply a displacement force to displace at least one of the medial upper paddle and lateral upper paddle relative to the lower paddle when engaging the first and second bones of the joint, or vary the displacement force based on flexion angle of the first and second bones of the joint or throughout a range of motion of the joint. Further, the controller can be configured to determine a gap spacing between at least one of the medial upper paddle and lateral upper paddle, and the lower paddle based on the displacement force and a deflection factor, as further described below. In any of the foregoing, the controller is configured to operate by the processor executing software or computer instructions stored in memory to achieve the specified operation. Thus, the memory can have stored thereon e.g., a predetermined force profile for applying varying displacement forces throughout a range of motion of the joint.

Force Sensor Calibration

The force sensors 130 are preferably pre-calibrated (factory calibrated) so that the device is ready to use in the OR. The sensors may be zeroed using an adjustment process, for example a mechanical adjustment, to ensure consistency and repeatability in the readings across devices. Alternatively, different calibration constants can be applied and associated with each ligament balancer. The ligament balancer may have computer memory stored within the body 9 for storing a unique calibration file with calibration constants that are associated with the distraction device.

Alternatively, the ligament balancer may be marked with a unique identifier, such as an identifying (ID) number, or a radiofrequency (RF) ID tag that is inputted into the computer. In this latter case, the computer is equipped with an RFID receiver for receiving the RF signal from the RFID tag in the ligament balancer. The number may refer to a look up table stored in software on the computer that associates a calibration file with that number.

Alternatively, the calibration file can be provided on transportable memory media, such as a USB drive, flash drive, CD-ROM, or the like, and provided with the ligament balancer. Thus when a ligament balancer is deployed to a new site that already has a CAOS system, it can be shipped with the accompanying calibration file that can be preloaded into the computer memory during installation of the device before it is first used. Thus the calibration file need only be uploaded to the computer once, upon which it can be used repeatedly. This makes servicing and recalibrating the device easier.

Alternatively, the CAOS station may be equipped with an internet connection (either wireless and/or wired) and the software with the corresponding calibration file may be updated automatically via the internet by wire or through the air. Alternatively, the calibration constants can be stored or coded in the ID number directly so that the look up table does not need to be updated to include new calibration files. Checks may also be included in the software to ensure the device ID that corresponds to the device being used has been entered and a corresponding and valid ID file is present. The software may also be implemented to monitor usage of the device (number of surgeries, time used during each procedure, cycles endured, mean and peak forces exerted by and on the device). Checks can also be incorporated in the software to ensure the device is brought back for servicing when servicing is due, or after reaching pre-established usage criteria (for example, number of surgeries).

Additionally, a separate calibration device or calibrator can be provided to check and/or recalibrate the device in the OR. The calibrator may include a mechanical spring of known force-distance relationship, such that when the ligament balancer is coupled with the calibration device and the actuators of the ligament balancer are activated, the spring will apply a known force based on the distance it is compressed or extended, and the distance can be measured using the ligament balancer. Thus the force measurements made by the distractor during actuation of the actuators can be compared with the known forces applied by the spring according to the distance travelled, and the software can determine if the device is in or out of calibration, and if recalibration is required, and in the latter, can apply a new calibration based of the measured and known forces during the intra-operative calibration process.

Additionally, the force sensors of the ligament balancer can be calibrated, or their calibration can be checked, by controlling and actuating the motors until they reach their limits of motion, essentially reaching a hard stop within the inside of the housing, and then correlating the input power signal to the motors with the output signal of the force sensor. As an example of the process, the force sensors in the distractor may be calibrated by the manufacturer after assembly of the device by applying external known loads to the upper paddles and then adjusting the force signal output by applying constants (in a linear or non-linear model) such that the force sensor output is calibrated to the known applied loads. The distractor can then be commanded to go to its maximum height until it reaches the internal stop, where the linear motion of the sliders stops and the amount of energy going into the motor begins to increase, generating an increasing amount of load on the force sensors. The energy (electrical current) delivered to the motor can be increased until it reaches a specific value, and the relationship of the output signal of the force sensor relative to the input energy signal to the motors can be quantified. Because the force sensor is initially calibrated using external loads or weights, the force corresponding to the energy or current inputted to the motors can be determined. It is assumed that the relationship between current inputted to the motors and force applied to the force sensors when the sliders have reached the hard stop remains constant over multiple uses and over the service life of the distractor, and therefor this relationship can be used to recalibrate the force sensors during use of the distractor, or to check the accuracy and reliability of the calibration of the force sensor either in the operating room or during routine diagnostic tests before or after use. This may be necessary if the force sensors need to be recalibrated from time to time due to repeated use, abuse (e.g., overloading causing damage or changes in the sensor characteristics), or repeated sterilization.

Modes of Control—Force, Height, Force-Height, Disabled, and Enabled

The CAOS system 1000 includes a user interface (see for example FIG. 9C) that allows a user to control the function and behavior of the ligament balancer 1. The user interface includes buttons for controlling the ligament balancer in one of several modes, including a force control mode, a height control mode, and force-height control mode.

Figure 9A:
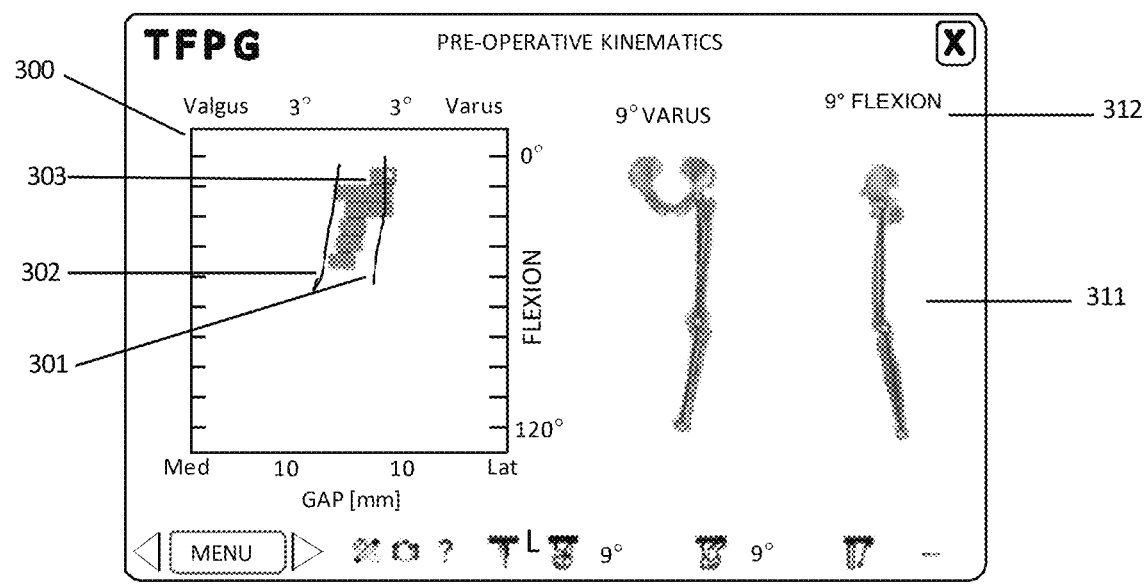
FIG. 9A is a screen shot view of a pre-operative kinematics acquisition user interface in accordance with an aspect of the computer aided orthopedic surgery system.
Figure 9B:
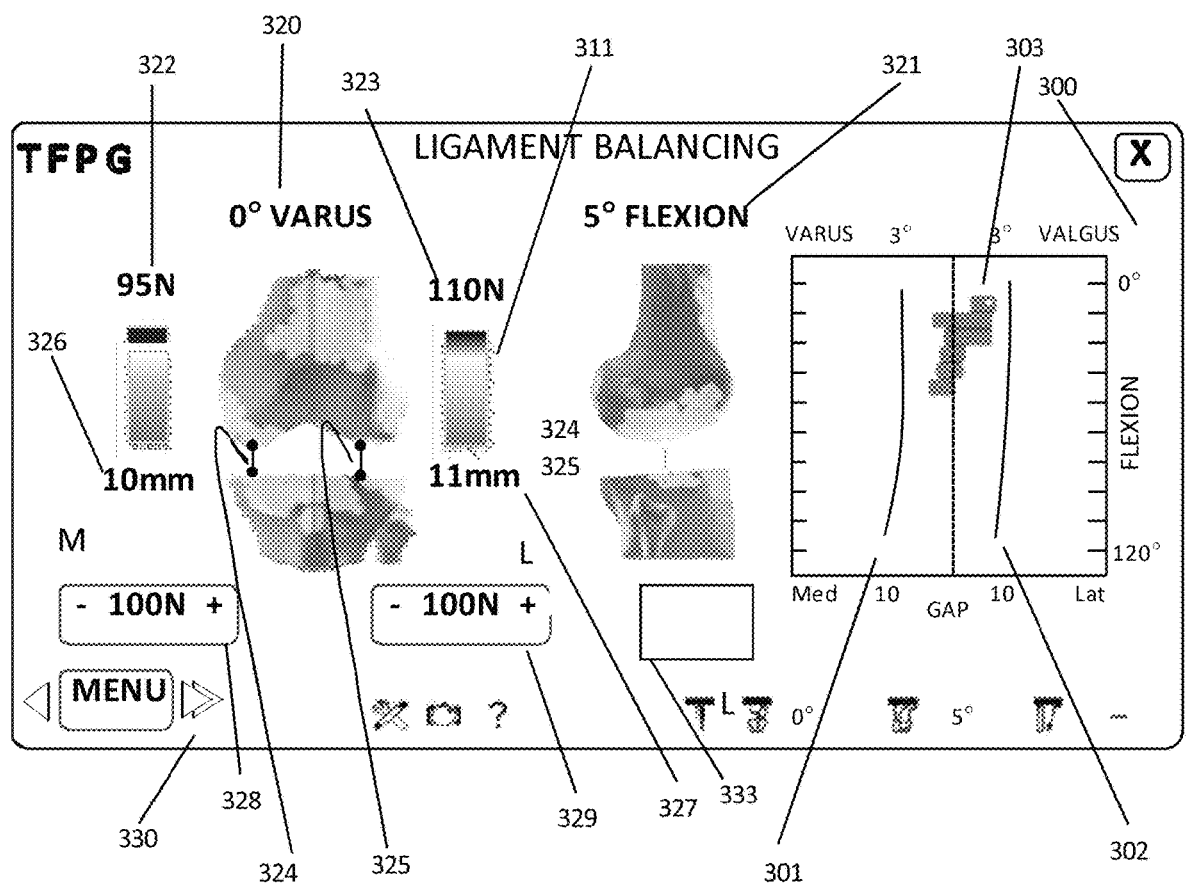
FIGS. 9B and 9C are screen shot views of a ligament balancing user interface in accordance with an aspect of the computer aided orthopedic surgery system.

Referring to FIG. 9B, in Force Control Mode, the user enters a target force for the medial and lateral sides of the displacement mechanism. The target force value may be the same or different for either sides. The actuators or drive assembly then actuate the upper medial and lateral paddles according to the error between the target force set by the user and the actual force measured by the each force sensor (error based control loop). Thus the actuators will raise each upper paddle if the measured force is lower than the target force, until sufficient tension is applied to the ligaments such that the force applied by the ligaments on the paddle approaches the target force. As the target force is approached, the difference (or error) between the actual force and target force decreases and the rate of actuation decreases correspondingly, until the actual force equals the target force. If the target force is less than the actual force measured by the sensors, the actuator will move the upper paddle down reducing the tension in the ligaments and soft-tissues surrounding the knee, until the actual force approaches and eventually reaches and stabilizes at the target force.

Figure 9C:
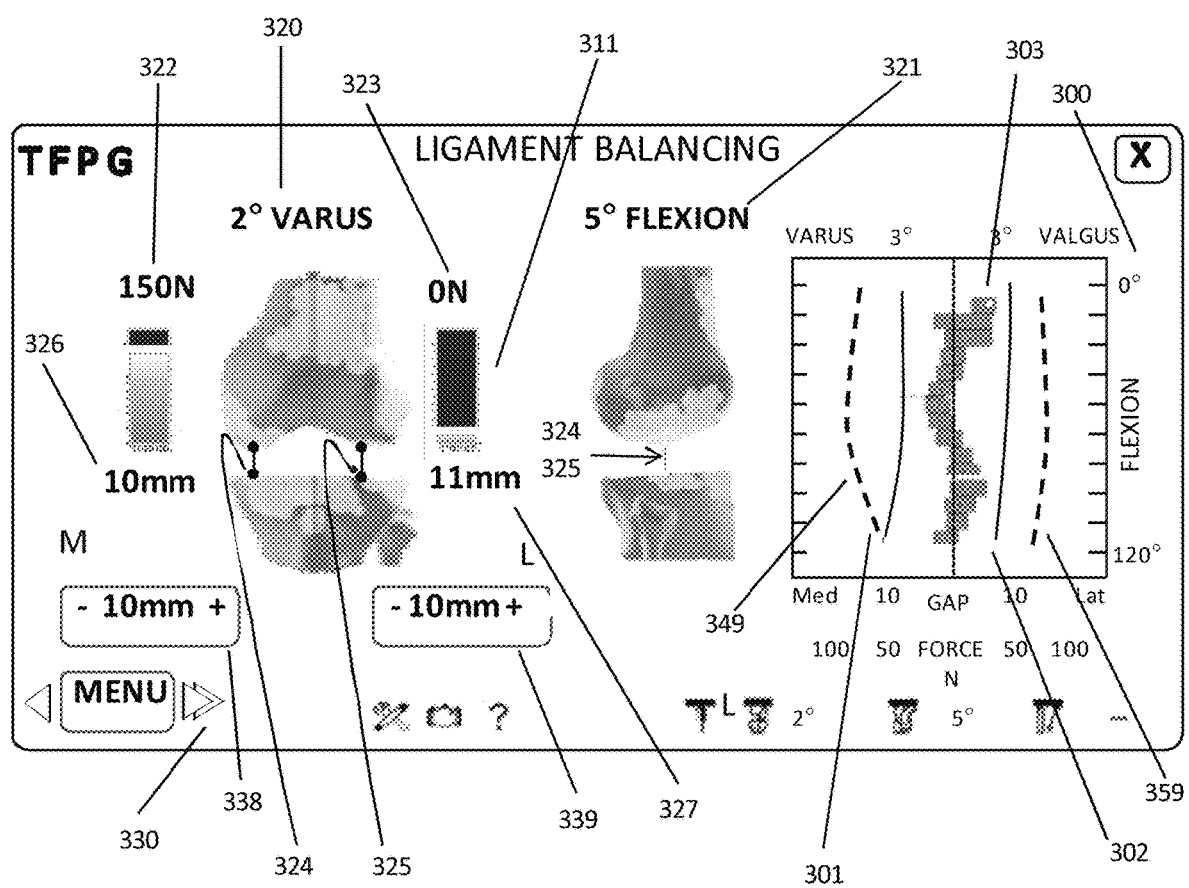

Referring to FIG. 9C, in the Height (or position) Control Mode, the user enters a target height, such as 10 mm, and actuator will move the upper paddle up or down based on the current height until the target height is reached. The height dimension is referring to the distance between the lower surface of the lower paddle and the upper surface of the upper paddle (or a minimum distance in the case of a concave-shaped upper paddle surface). When an augment is used, the height dimension is referring to the distance between the lower surface of the lower paddle and the upper surface of the augment (minimum distance in the case of a concave-shaped augment surface). The additional height added by the augment can be taken into account by the computer's software either automatically depending on what step the surgeon is at in the surgical protocol (e.g., ligament balancing step with no augments, or virtual trailing step with augments), or it can be taken into account manually by pressing a button on the user interface.

In the Height Control Mode, the distraction system is controlled based on its height (or position), and displays the forces measured by the force sensors that are acting on the upper and lower paddles. The user interface for controlling the ligament balancer can be a graphical user interface programmed into the software and displayed on the display, with buttons for control. The user interface can also include buttons 108 (FIG. 6A) that are incorporated directly on the body of ligament balancer to allow a user to change the control mode, to set or adjust a targeted force or height value, or to start and stop or pause the motion of the ligament balancer. The buttons can be integral to (i.e., built in) the body of the ligament balancer (for example, on the housing), or they can be disposable and attached to the ligament balancer at the beginning of the case. They can be clipped on to the body and made of plastic to reduce costs, and can include a battery and wireless communication with the computer and/or controllers.

The distraction device may also be switched to a disabled mode, where the actuators are not being driven or powered, and the user is able to back-drive the system by pushing down or pulling up on the upper paddles or paddle connectors to manually change the height of the device. When the device is disabled, the system is still able to read the position (height) of the upper paddles using the encoders or hall sensors. When the device is enabled, it operates in one of the functional control modes.

Figure 5A:
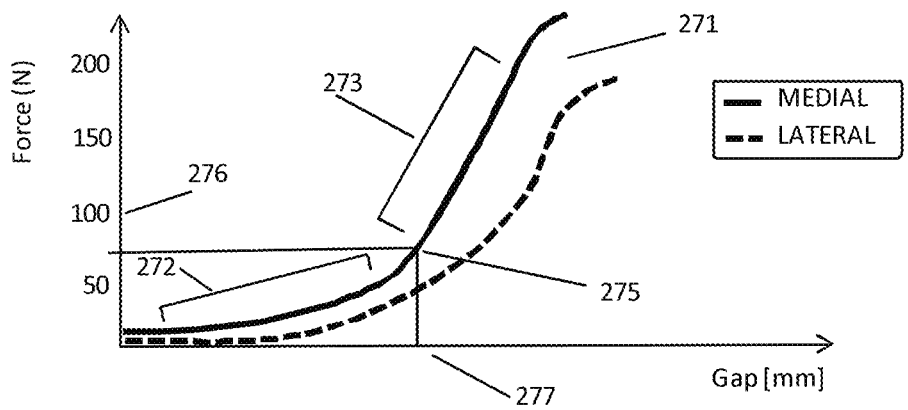
FIG. 5A is a representation of a force vs. elongation relationship measurement acquired by the orthopedic distraction device of FIG. 2A.

In the Force-Height Control Mode, the distraction device 1 measures the force-height (or force-elongation) relationship of the knee soft-tissues, thus measuring the mechanical properties of the soft-tissues surrounding the knee joint. The objective is to accurately and reliably characterize the mechanical properties of the knee soft-tissue envelope, and produce plot or graph of the force (y) vs. displacement (x) curve for the medial and lateral compartments (FIG. 5A). In this mode, the ligament balancer is inserted in the knee and starting from a lower position, the upper medial and lateral paddles lift up and apply a progressively increasing amount of tension to the soft-tissues. Thus the system is measuring the force and the displacement as the ligament balancer increasingly spaces apart the knee joint. This measurement can be realized by any control modes, including a 1) Constant Velocity Control (FIG. 5B) and 2) Force Velocity Control (FIG. 5C).

Figure 5B:
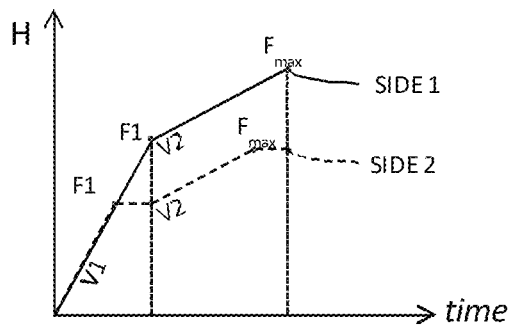
FIG. 5B is a representation of the height vs. time constant velocity control mode of orthopedic distraction device of FIG. 2A.
Figure 5C:
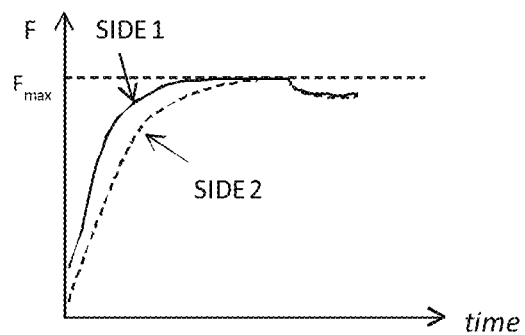
FIG. 5C is a representation of the force vs. time relationship for the constant force-velocity control mode of orthopedic distraction device of FIG. 2A.

For Constant Velocity Control, the rate of displacement (velocity) of each actuator is controlled according to the current value of the measured force (F), FIG. 5B. Velocity 1 (V1) is applied first, from the lowest position until Force 1 (F1) is reached. Then Velocity 2 (V2) which may be a lower rate, is applied until a maximum force (Fmax) is reached. Then, the actuator switches to disabled mode (see section below on synchronization). All parameters may be adjustable by the user to suit their preference for velocity and force characteristics. In a simpler mode, V1 and V2 can be set to the same velocity.

Synchronization—It is desirable to have both sides trace the upper portion of the force vs. displacement curve simultaneously, to minimize any potential artefacts caused by tensioning only one side at a time (for instance, some soft-tissues such as the PCL could contribute to the stiffness curve on both the medial and the lateral side). Ideally each side would be applying the same force on either side at the same point in time. This can be approximated in the Constant Velocity Control mode as follows: 1) both sides start at V1 from a lowest position; 2) one side will reach F1 first and will deaccelerate to zero velocity until the second side reaches F1; 3) then both sides will start at V2 until Fmax is reached; 4) the first side to reach Fmax will stop and wait (maintaining the force, or height) until the other side reaches Fmax; then both sides will become disabled. Alternatively, both sides may trace the force-elongations curve at a constant velocity until a maximum force is reached. One side will reach the maximum force before the other side, and will deaccelerate and maintain the force (in force control mode) or maintain the height, until the second side reaches the maximum force, at which point both sides can either maintain the force or height, switch to disabled mode, or lower their height.

Force-Velocity Control (FIG. 5C)—The force vs. gap curve can also be acquired using a simple error controller (such as a proportional-integral-derivative controller, or PID controller) where the motor velocity is proportional to the difference (error) between the actual force and the target maximum force. A Maximum Velocity (Vmax) and Maximum Force (Fmax) are set. The PID parameters may be determined imperially (through tuning) to optimize the responsiveness, stability, and overshoot characteristics of the control loop, targeting a complete sweep measurement in about 3-5 seconds. Once one motor reaches the target force Fmax, it holds its position until the second motor reaches Fmax, then both motors are disabled (FIG. 5C).

The system may include analytical software to automatically analyze the force displacement curve, for example, by finding linear or non-linear best fit relationships for different portions of the force vs. displacement curve. A patient specific tension or force 276 or gap 277 value may be determined based on the shape of the curve, either automatically using linear or non-linear curve fitting techniques, or manually by plotting the curve and allowing the surgeon to visualize the shape of the curve. For example, a typical force elongation curve may be divided into several regions, including a first so called 'linear' part where the fibers of the ligaments are going from a non-aligned or crimpled state 272 to an aligned state, and a so called second part 273, where the fibers are being tensioned within their elastic deformation region, where the rate of increase of tension is directly proportional to the rate of increase in elongation, by a constant stiffness factor. A third portion of the curve may represent where fibers begin to fail and start to become detached from the bone (plastic deformation).

The ideal patient specific tension 275 as determined from the force vs. displacement curve, may depend on the patient's profile and characteristics, such as the activity level of the patient, age, BMI, gender, and so on. For example, a surgeon operating on a young active patient can chose to leave the knee joint in a higher amount of tension (i.e., further to the right of 275, along the curve 271 shown in FIG. 5A) than in an elderly non-active and underweight patient (which may be further to the left). Thus the present invention allows the surgeon to quantify the load displacement characteristics of a particular patient's knee joint and then determine based on the patient profile where is the optimal tension for that patient along the curve relative to distinct features of the curve.

In accordance with another aspect, the present invention provides methods and software executable for compensating for deflection of the upper and or lower paddles and/or displacement mechanism (and the motion of the motors relative to the displacement mechanism) under applied loads. Forces applied to the upper arms of the ligament balancer when it is operated in height control mode, for example forces applied by the surgeon during a knee stability test (e.g., varus valgus stress test) or by the knee ligament tensions, may cause deformation of the upper paddles 22, 24 and/or lower paddle 12 and lower paddle attachment interface 16, and the actual height of the ligament balancer may not correspond to the targeted height of the ligament balancer. Similarly, forces applied by the ligament balancer in force control mode may cause deflection of the attachments and the height reported by the motors and controls may not correspond to the actual height. In order to correct for these deflections, the relationship between the applied forces and deflections may be measured and quantified under known loads a priori. This may be quantified as a deflection factor accounting for various heights throughout the range or motion of each side, various anticipated loads, and for each side and set of attachments (12, 22, 24). These measurements may be tabulated in a look-up table or an analytical relationship (for example linear or non-linear curve fitting) may be used to describe the load, height, deflection relationship.

During use, the applied forces measured by the force sensors may be used to estimate the deflection of the ligament balancer at any given height based on the pre-established load-deflection relationship. In order to compensate for deflection, when the ligament balancer is operated in height control mode, the actual targeted height may be adjusted automatically and in real time by the software running on the computer and or firmware running on the controllers (the position control loop) to compensate for the amount of deflection occurring, wherein the amount of deflection is known from the a priori determined load-deflection relationship.

For example, if 100 N of applied force results in 1 mm of deflection on the lateral side, when the ligament balancer is being operated in height control mode and is targeting an 11 mm thick insert, and as loads are being applied to the ligament balancer and the force sensors are measuring the loads, the targeted height is being adjusted according to the measured loads, and when 100 N is applied the height target is adjusted or increased by 1 mm. The height is increased proportionally more or less when the measured force is more or less, respectively, according to the known load-deflection relationship. Similarly, the heights measured by the ligament balancer (via the motors, hall sensors, encoders, and/or controllers) in force control mode, or in the force-elongation control mode, may be adjusted to account for the deflection occurring under the applied loads, according to the known load-deflection relationship.

Pre-Operative and Post-Operative Joint Kinematics

In accordance with another aspect, the present invention includes capabilities and methods for measuring the pre-operative (i.e., bone pre-resection) and post-operative (post-bone resection) kinematics of the joint. This is accomplished by tracking the relative 3D positions of the bones of the joint (tibia and femur) using the 3D tracking system 2 and the reference markers 107, 106, associated with or attached to each of the bones, and using software executable to compute multiple motion parameters that describe the relative motions of the bones. Pre-operative (pre-op) kinematic measurements are typically done after the initial registration of the knee joint anatomy, femoral 98 and tibial 99 mechanical axes, and bone coordinate systems. In order to measure knee kinematics, the surgeon takes the knee through a range of motion (flexion) and the 3D tracking system will measure the overall alignment of the mechanical axis (varus and valgus, as determined by the angle between the tibial and femoral mechanical axes) as a function of the knee flexion angle. The overall alignment of the mechanical axis may be computed throughout flexion as the angle between the tibial mechanical axis and the sagittal plane of the femur, which is coincident with the femoral mechanical axis.

As shown in FIG. 9A, the user interface may include representations of the bones of the joint, showing the real-time relative positions of the bones 311. The pre-op kinematic measurements may also include the following measurements: the knee flexion angle 312 including maximum extension and maximum flexion, which can be represented graphically on a graph 300, along with maximum varus angle and maximum valgus angle throughout the range of flexion 303, medial 302 and lateral 301 gap values between the tibia and the femur throughout the range of flexion (average, minimum, and/or maximum), internal and external rotation of the tibia relative to the femur (average, range, or as a function of flexion). The medial 302 and lateral 301 gaps can be determined by computing a closest distance between the medial and lateral surfaces (respectively) of the femoral condyles and various points or planes on the tibia or tibial insert, depending on the stage of the procedure. For instance, the medial gap can be computed by searching for the point on the medial femoral condyle that is the closest distance to a specific point on the medial aspect tibia (such as a medial cut height reference point), or a plane on the tibia (for example, the planned or measured tibial resection plane), where the closest distance could be searched for and computed along a particular direction, such as along the tibial mechanical axis direction, or along the direction normal to the planned or measured resected surface.

As shown in FIG. 9B, in the case where a tibial resection has already been performed, the medial 324 and lateral 325 gaps can be determined by computing a closest distance between the medial and lateral surfaces (respectively) of the femoral condyles and the measured surface of the tibial cut. Pre-operative gaps can be computed as the distance between a planned tibial cut surface, or between the tibial cut height reference points (tibial cut depths) digitized on the medial and lateral plateaus of the tibia, and the medial and lateral surfaces of the native femoral bone.

Figure 10A:
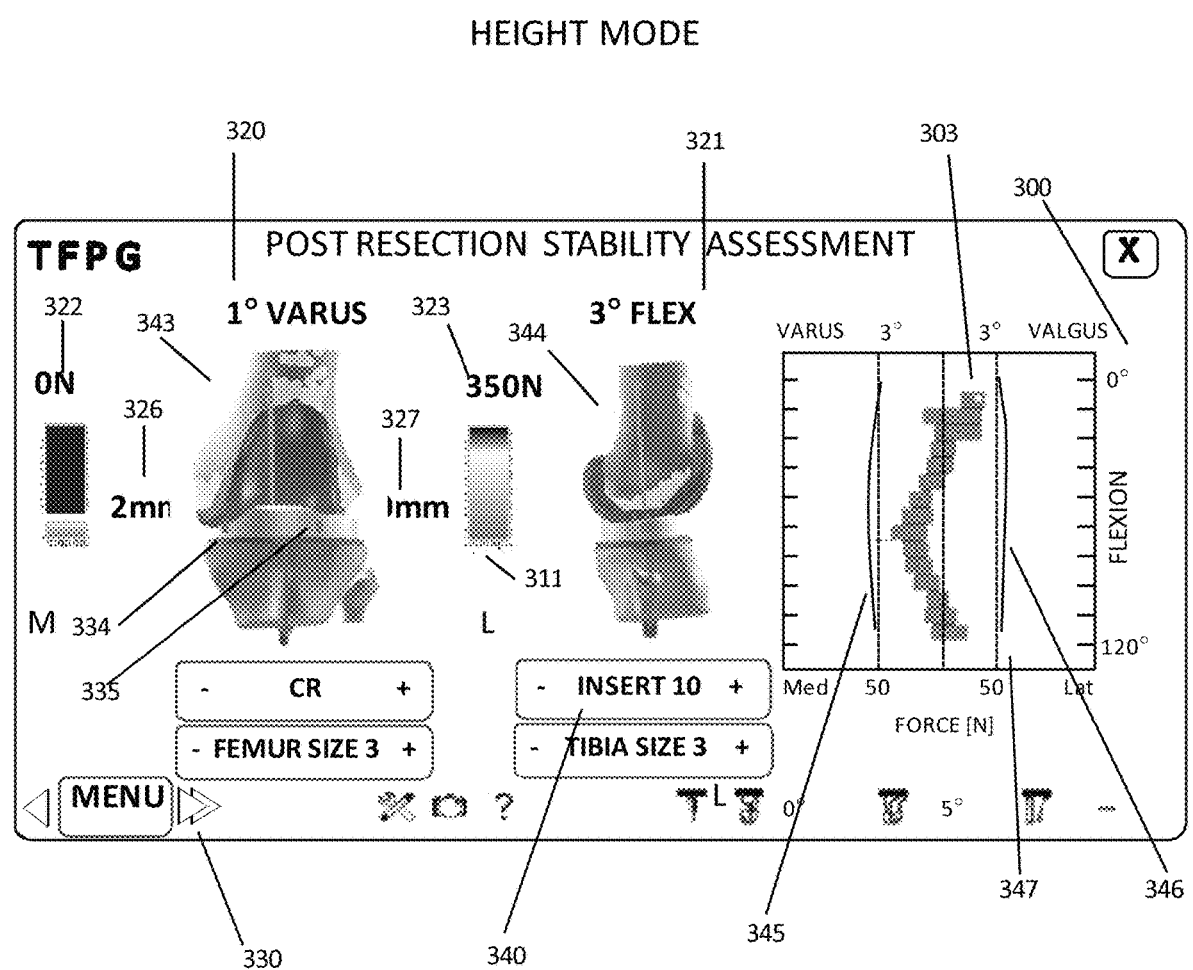
FIG. 10A is screen shot view of a post-resection stability assessment user interface for height mode in accordance with an aspect of the computer aided orthopedic surgery system.
Figure 10B:
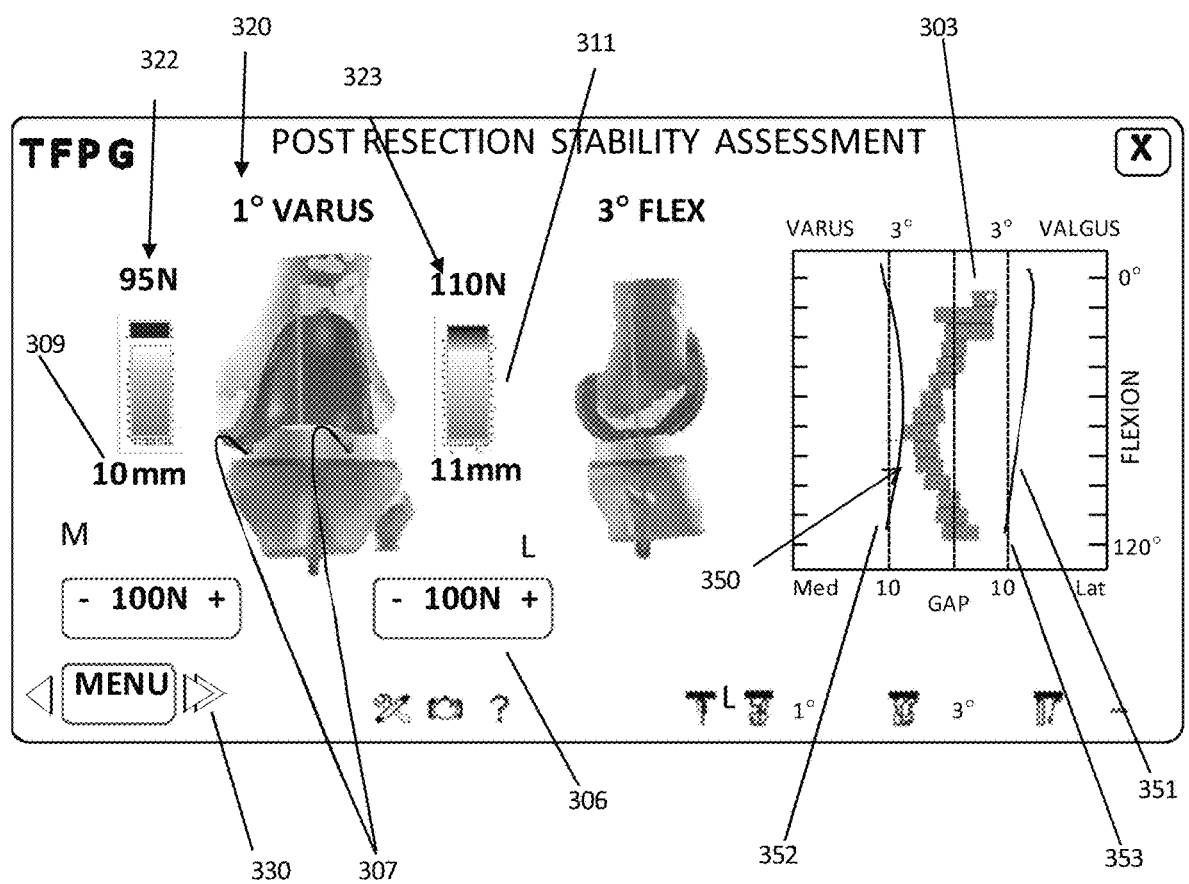
FIG. 10B is screen shot view of a post-resection stability assessment user interface for force mode in accordance with an aspect of the computer aided orthopedic surgery system.

As shown in FIGS. 10A and 10B, post-operative gaps 307 can be computed as the distance between the virtual tibial insert (for example, lowest point on the medial and lateral plateaus on the insert) and the virtual femoral component (i.e., articulating surface of the implant). Post-operative gaps can also be computed as the distance between the virtual tibial cut and the virtual femoral component (i.e., articulating surface of the implant). During the measurement of pre-op and post-op kinematics, stresses can be applied to the joint by the surgeon, such as varus and valgus stresses at discrete flexion angles, or throughout flexion, in order to measure the opening on the lateral and medial sides of the knee, respectively. Graphical plots 300 or charts can be generated on the display in real time to show the varus/valgus angulation, medial and lateral gaps, tibial rotation, and medial 345 and lateral 347 forces (FIG. 10A) plotted against the flexion angle. Pre-op and Post-op graphs can be shown side by side to allow for comparison of the pre-op and post-op kinematics.

Ligament Balancing

The CAOS system 1000 also includes capabilities for acquiring gap data with the displacement mechanism 1 after a tibial resection has been performed but before any resections have been performed on the femur. FIG. 9B shows an example of a user interface that may be used to acquire gaps at different flexion angles or throughout flexion. The user interface includes the display of the following values in real time: Overall varus/valgus alignment 320, flexion 321, the amount of applied force on the medial 322 and lateral 323 sides, the medial and lateral gap between the tibial resection and the native femoral condyle, displayed graphically on the bone models 324, 325, and as numerical values 326, 327, and on a graph 300 plotted against the flexion angle 301, 302. The overall alignment 303 may also be displayed on the graph 300, as real time (white dot) and maximum varus and maximum valgus angles, represented as the width of the bars 303 at each flexion angle.

The user interface may also include buttons 328, 329 for adjusting the (targeted) force applied by the ligament balancer on the medial and lateral side either up or down. Alternatively, the medial and lateral force can set to the same value using only one button that adjusts both the medial and lateral side at the same time. Color coded lines or bars 311 may be used to indicate or highlight the amount of force being applied on the medial and lateral side, and may indicate the proximity of the actual force to the target force.

The ligament balancing step, where the positional relationship between the tibia and femur is measured and stored throughout flexion, may be performed in force control mode as shown in FIG. 9B, or it may be with the ligament balancer operating in the height control mode, where the medial and lateral gap heights are controlled by the ligament balancer and buttons on the user interface, and the forces acting on the medial and lateral sides of the ligament balancer are displayed in real time both numerically and graphically on a chart as a function of flexion. In height control mode, the surgeon may adjust the height independently on each side until the medial and lateral gaps between the femur and tibia are filled up, using the force values to monitor the force being applied. The surgeon can then perform a stability test, such as a varus valgus stability test to assess the stability of the joint with that thickness of material being inserted in the knee. The on screen force and gap values can be used to quantify and monitor the assessment and standardize the force being applied.

In one embodiment of the present invention, the CAOS system 1000 may be used to assess how tight or loose the knee feels based on an applied force. The ligament balancer may be inserted in the knee after making a tibial cut and operated in force control mode, tensioning the ligaments and soft tissues until the targeted force is achieved. The surgeon may decide to release ligaments until an appropriate (overall) alignment is achieved. Once the targeted force is achieved in force control mode and the gap is stable, the ligament balancer may be locked at the current height. For example, by pressing a button on the screen that switches the operational mode of the ligament balancer, i.e., switching it from a constant force mode to a constant height mode, FIG. 9C, so it is locked at the height that created the targeted tensions and it displays the forces 322, 323 acting on the upper medial and lateral paddles in real time. The surgeon can then stress the knee into varus and/or valgus, by pushing medially or laterally on the tibia or ankle, and while monitoring the opening of the gap 326, 327 on the lateral and medial sides. They can use the force readings (values 322, 323, or curves 349, 359) on the display to control the force that they are applying on the tibia or ankle while monitoring the opening of the knee 326, 327 on the user interface (navigation screen).

Thus a repeatable way of performing the stress tests from patient to patient as a result of the force readings is achieved. The goal of evaluating the knee opening (gaps) is to allow the surgeon to feel how tight or loose the knee would be if the implants were planned to have a zero gap value at the targeted applied force for that flexion angle, and to potentially determine if the knee is going to be too loose or too tight given the planned position before they make any femoral cuts, so they can adjust the plan accordingly. This can be performed in extension, flexion, or any flexion angle. Gaps 301, 302, forces 349, 359, and alignment 303 may be plotted against flexion (FIG. 9C), or they may be plotted against time to show the correlation between the gaps, alignment, and applied forces as the knee is being stressed in varus and valgus at a given flexion angle. Broken, weighted, and/or colored lines may be used to distinguish the variables from one another and associate them with the corresponding axis labels.

Applied Force as a Function of Flexion Angle

In accordance with another aspect, the CAOS system includes capabilities for adjusting or controlling the function of the ligament balancer 1, including the amount of force being applied, or the height being applied, by the ligament balancer, as a function of the relative position of the bones of the joint. This has unique advantages, for instance the amount of force being applied to the joint can be automatically adjusted based on the current flexion angle of the tibia with respect to the femur. This can be controlled in either a static or dynamic gap acquisition protocol.

For example, the system could be used to acquire gaps in the knee joint at specific flexion angles, such as at two or more of the following flexion angles 0, 20, 30, 60, 90, 120 degrees of flexion. The specific desired applied force at each of these flexion angles can be controlled by the computer's software, and can be inputted by a user before or during each case, or can be stored in a user profile that includes the user's preferences and preferred options. Thus, when the user inserts the ligament balancer into the knee and brings the knee into extension, the ligament balancer can start from a lowest position in force control mode and increase its height and applied force until the desired force at around 0 degrees flexion (i.e., extension) is reached. Then, the CAOS system stores the relative position of the tibia and femur, and the associated knee joint gaps. The user can then bring the knee into various degrees of flexion, while the software automatically monitors the knee flexion angle and actively controls the force being applied at each flexion angle accordingly. The acquisition can be static, where the user momentarily holds the knee at each flexion angle to acquire the gap value at that specific flexion angle, and the software automatically registers the gap value once the user reaches the flexion value and the force has stabilized at the target force at that flexion angle. This has the advantage of ensuring the target force has been achieved at each targeted flexion angle before the user moves to the next flexion angle, as well checking and ensuring other parameters, such as a neutral internal or external rotation of the tibia with respect to the femur during the acquisition.

Various criteria can be assigned for the automatic acquisition, such as a time criteria, wherein the flexion angle and applied force as measured by the sensors has stabilized and are within a predefined value or threshold, for example, stabilized for one or more seconds. Criteria for the other parameters can also be assigned, such as force within a certain number of units (e.g., +/−5 N), rotation with a certain amount of degrees, etc. An indicator can then be displayed on the screen informing the user the gap at that flexion angle has been stored by the computer, signaling them to proceed to move the leg to the next flexion angle. As the knee is brought towards the next flexion angle the computer can begin adjusting the force to approach the next desired force at the subsequent flexion angle.

The acquisition can also be continuous (dynamic), wherein the system acquires the gaps though out a range of knee motion (flexion), without pausing at each discrete gap value. In this case the 3D tracking system controller is continuously monitoring the joint or flexion angle and inputting this into the controller, which is dynamically adjusting the applied force as a function of the flexion angle in real time, while the computer is storing the relative position of the femur and tibia. Thus the surgeon can dynamically move the leg throughout a range of flexion while the distractor controls the applied force and distracts the joint in real time, and the relative position of the two bones throughout the range of flexion and distraction is recorded and displayed to the user, and used to plan the position of the femur implant relative to the bone.

This has the advantage of being more efficient and acquiring continuous information that can be presented as curve over the continuum of flexion. In either the static or continuous acquisition scenario, kinematic (motion), dynamic (forces), and other parameters may be monitored during the acquisition and displayed to the user in real time, such as internal-external tibial rotation relative to the femur, varus-valgus angle, medial and lateral gaps, anterior-posterior positon of the tibia with respect to the femur, femoral rollback on the tibia, and the load bearing axis (line joining the hip center to ankle center) and the position, such as mediolateral position, where it crosses the knee.

Virtual representation of the bone models may be displayed on the screen in multiple views or anatomical planes during the acquisition to provide kinematic information and to help the user guide the motion of the bone during the acquisition. The computer and controller may control the applied force at intermediate flexion angles by interpolating between the target values entered by the user for the specific flexion angles. The interpolation may be done beforehand once the user profile is loaded into the software so the target force values may be pre-stored for every flexion angle in a look-up table format. Alternatively, the target force values may be calculated (or interpolated) in real time based on the nearest adjacent targeted force and flexion paired values. The user may also enter the desired applied force as a function of the flexion angle graphically by drawing a line or curve on a graph of force vs flexion, or by editing points on the curve either with up/down buttons or directly on the curve itself by modifying node control points on the curve directly. This can be done prior to or during the surgery. Thus a user is able to enter a desired profile for the applied force as a function of flexion allowing the computer to automatically control the force applied between the joint as the knee flexion angle is varied during the procedure, this allowing the surgery and the implant position to be planned with different tensions in the ligaments corresponding to different flexion angles.

Figure 7:
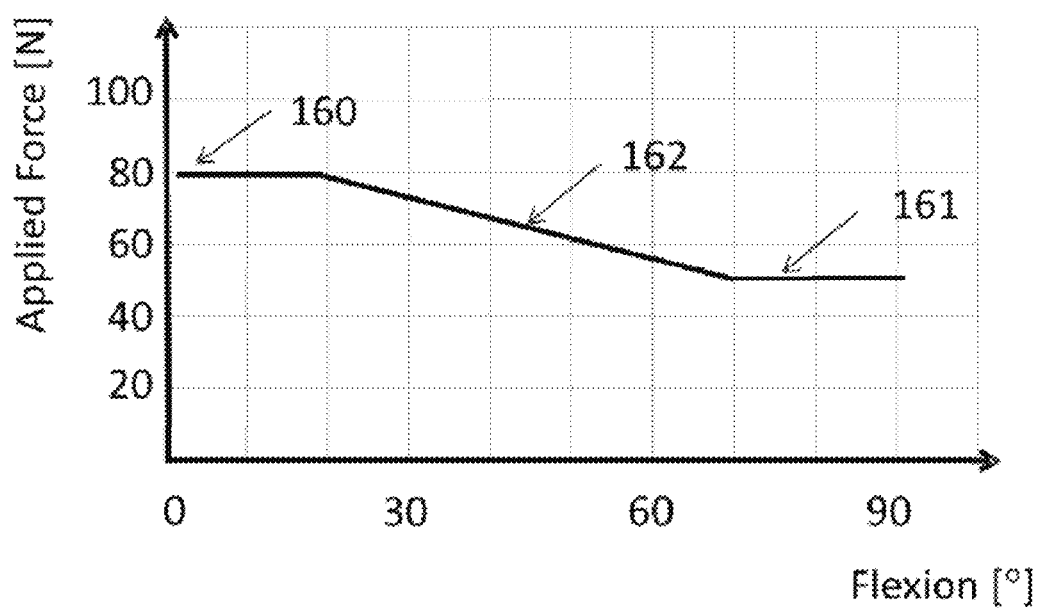
FIG. 7 is an illustration of force vs. flexion profile applied by the orthopedic distraction device of FIG. 2A.

For example, as illustrated in FIG. 7, a user may enter into their user profile a greater applied force as a target in extension 160 (for instance, 80 N per medial and lateral side at 0 degrees extension), and lower force in flexion 161 (for instance, 50 N per medial and lateral side at 90 degrees flexion). Additional target force values at other flexion values can be entered as previously mentioned, and these target values can then be interpolated, either linearly 162, or non-linearly, to achieve a target force for all possible flexion values. Limits for the amount of flexion or the amount of applied force can be set by the user, or automatically incorporated into the software. The adjustable applied force vs. flexion graph can be displayed directly on the ligament balancing user interface shown in FIG. 9B, thus allowing the surgeon adjust the curve on the fly, or it can be established and stored in the user profile options prior to or at any time during a surgery.

Figure 9D:
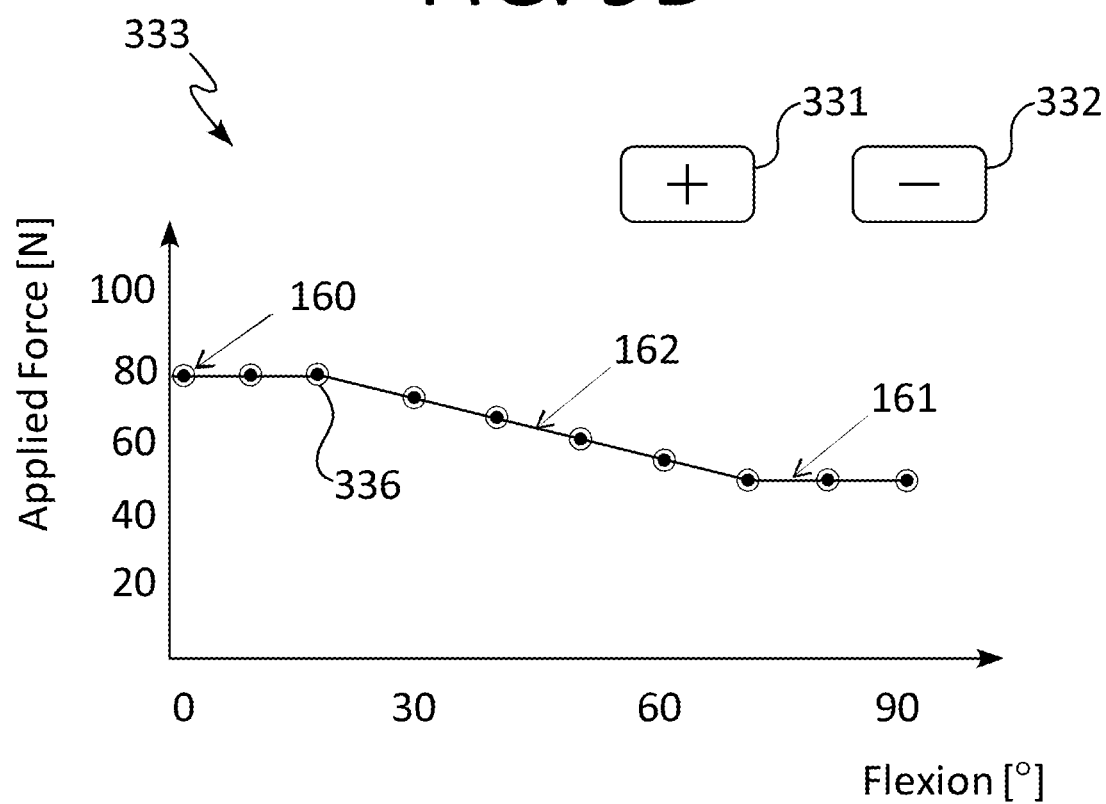
FIG. 9D is an illustration of an applied force vs. flexion profile screen of the ligament balancing user interface of FIG. 9B.

In other words, the user interface shown in FIG. 9B can be configured to include a graphical display 333 (FIG. 9D) of the applied force vs. flexion profile. This graphical display serves to control and set the amount of force to be imparted on the joint. The graphical display is preferably equipped with buttons 331, 332 to adjust the amount of force selected e.g., at a selected flexion angle. The selected flexion angle can be segmented into various intervals e.g., at every 10 degrees of flexion and configured with corresponding node control points 336 to allow for adjustment of the force setting.

Additionally, with the acquired force elongation profile or the applied force vs flexion profile, the user can plan resection depths based on a preferred or predetermined force to be imparted on the joint e.g., between two joint bones of the knee joint. That is, the user selects the preferred or predetermined force to impart on the joint and the computer determines the required resection depths for the tibial and femoral resections necessary to achieve the desired gap spacing corresponding to the selected force based on the acquired force elongation profile.

Implant Planning with Predictive Gaps

Figure 8:
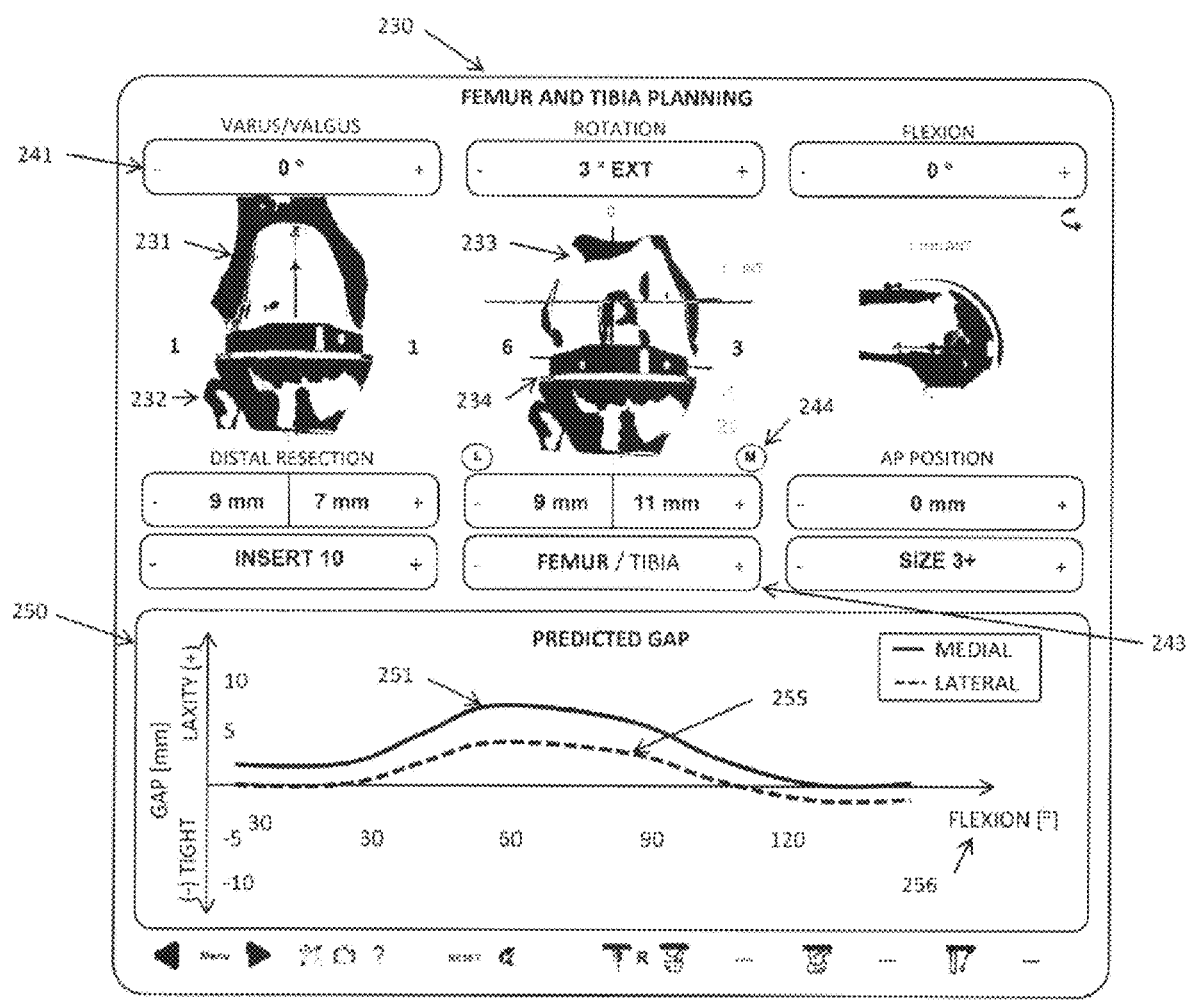
FIG. 8 is a representation of a femoral and tibial planning user interface in accordance with an aspect of the computer aided orthopedic surgery system.

The CAOS system 1000 has the ability to plan the position of the implants based off the gap data acquired with the ligament balancer 1 in the joint, using gap data that is acquired at various flexion angles. FIG. 8 shows an example of a graphical user interface 230 that may be used to plan the position of the femoral component based off predicted gap data. The interface includes representations of the femur 231 and tibia 232, which are derived from 3D bone models, and representations of a femoral 233 and a tibial 234 implant positioned on the bones. The bone models are preferably generated by image free means, such as by deforming a statistical shape model or atlas that is initially generic and not specific to the patient's bones as previously mentioned. Systems and methods for creating computer bone models applicable to the present invention are disclosed e.g., in U.S. Pat. Nos. 8,126,533; 9,248,001; 9,220,571; and 8,990,052, the entire disclosures of which are incorporated by reference herein for all purposes.

The interface allows for planning of either the tibia or femoral implant positions, or both. The interface includes buttons 241 that allow adjustment of the position of the implant in any direction, such as Varus/valgus, Rotation, Flexion, Distal/proximal (Distal Resection), Anterior-Posterior (AP) Position, and Medial-Lateral (ML) position. Buttons may also be included for changing the type of implant (for example, CR or Cruciate Retaining, PS or Posterior Stabilizing, UC or Ultra-Congruent).

The CAOS system is equipped with executable software that calculates a predicted gap at various degrees of flexion 250. The predicted gap is the amount of gap or space between the femoral and tibial implants when the implants are planned at their current locations, given the relative positions of the femur and tibial bones as measured during the static or dynamic gap acquisition (ligament balancing) measurement. Thus the system has the ability to display a predicted medial 251 and lateral 255 gap value or curve as a function of the flexion angle 256 of the knee joint and as a function of the user's planned femoral and tibial implant positions.

An advantage of this is that the user can observe the consequence of any change in the implant position and the bone cuts on the predicted gap on both the medal 251 and the lateral 255 sides throughout flexion, including in midflexion (for example, from 15 or 20 degrees to 60 or 70 degrees flexion). Alternatively, the gap can be acquired and/or represented at several discrete flexion angles, such as 0, 30, 60, 90, 120 degrees of flexion. The gaps may also be represented as the distance from the tibial resection to the femoral implant surface, and reference lines may be positioned on the graph to indicate the targeted tibial implant (insert+baseplate) thickness (for example, a 10 mm thick implant would be represented by a line at 10 mm gap throughout flexion) allowing the surgeon to easily discern the difference between the predicted gap and the implant thickness throughout flexion, and whether there are specific areas of flexion where the predicted gap is too tight (i.e., less than 10 mm), or too lax (i.e., greater than 10 mm), and whether these discrepancies may be corrected by adjusting the positon of the implant. The predicted gap curves may also be color coded to highlight the discrepancy between the targeted implant thickness (or targeted gap) and the predicted gap.

For instance, when the predicted gap is <1 mm than the planned implant thickness the curve may be color coded red to highlight potential tightness in the corresponding area of flexion, when it is within −1 mm to 0 mm it may be color coded yellow, when it is within 0 mm to 1 mm or 2 mm it may be green, and when it is >1 mm or >2 mm it may be blue, and so on. For instance, the predicted gaps may indicate that the knee is overly lax in mid-flexion, and the surgeon may adjust the flexion of the femoral component to change the shape of the predicted gap such that the gap is not overly lax in midflexion. Adjusting the flexion of the implant may change the shape of the predicted curve depending on the design of the implant and the sagittal plane curvature (i.e., the radii of curvature in the sagittal plane). For instance, femoral implant designs with so-called 'J curves' have different radii of curvature along different ranges of flexion, and so changing the flexion angle of the implant relative to the femur will change where the radii and outer surfaces are positioned on the bone and thus the predicted gap curves.

Thus a surgeon may be able to optimize ligament balance and gaps in extension, midflexion, flexion, or deep flexion by adjusting and fine tuning the position of the implant to achieve the desired gaps or gap profiles. Additionally, the predicted gap curve 250 may be presented vertically with medial on one side and lateral on the other side as shown in FIGS. 9A and 9B, 300. Overall varus/valgus alignment data 303 with maximum varus and valgus values (bars) may be superposed. Moreover, the overall alignment data may be predictive alignment data that is dependent on the angle of the implants or resections relative to the femur and tibial bones.

To calculate the predicted alignment, it is assumed that the femoral implant is articulating on the tibial implant on both the medial and lateral sides throughout flexion, so the overall predicted alignment is based off where the femoral and tibial implants are positioned relative to the mechanical axis of their respective bones (i.e., varus valgus angle and internal external rotation angle). The overall predicted alignment can thus be the angle between the tibial mechanical axis and the femoral sagittal plane, assuming the medial-lateral axes of both implants are parallel and the femur is in continuous contact with the tibia. For instance, if a tibial cut is made at neutral relative to the tibial mechanical axis and a femoral implant is planned at 3 degrees varus in the frontal plane, the overall predictive varus/valgus alignment shown on the screen during the femoral planning graph may be 3 degrees varus. Thus the predictive overall alignment may be the sum of the individual femoral and tibial component alignments, which can be calculated throughout flexion and displayed or overlaid on the graph 250. The pre-op alignment and gap curves may also be overlaid to allow for comparison between pre-op and predicted post-op alignment and gap curves.

The CAOS system also has the capability to simulate the looseness or tightness of the joint based on the planned positions of the implants. With the ligament balancer in the knee and the femur and tibial implants planned, the ligament balancer can be used in a height control mode where it automatically adjusts its height according to the planned position of the implants and the degree of flexion that the knee is positioned at. The height of the ligament balancer is set so that it replicates the amount of implant that will be in the joint post resection of the bones, taking into account the difference in the native bone geometry to be resected, and the planned implant surfaces and thickness. Any method for simulating the laxity of the joint may be used, including those described in U.S. Pat. No. 8,337,508, which is hereby incorporated by reference in its entirety for all purposes. Thus the surgeon may use the predictive gaps shown on the display to evaluate potential tightness or looseness, and/or they may use the actual knee with the ligament balancer inserted and height controlled according to the plan. The surgeon can perform a varus or valgus stress test at any flexion angle, using the force readings on the display to control the force (moment) that they are applying at the tibia or ankle and monitoring the opening of the knee on the navigation screen. Thus they have a repeatable way of performing the stress tests from patient to patient and throughout flexion as a result of the force readings.

The goal of evaluating the knee opening (gaps) throughout flexion is to allow the surgeon to potentially determine if the knee is going to be too loose or too tight given the planned position before they make any femoral cuts, so they can adjust the plan accordingly. This could prevent femoral mal-rotation in flexion or flexion contractures/hyper extension. Advantages may include performing fewer recuts in the OR, or having to use a larger insert thickness and potentially elevating the joint line.

Figure 10C:
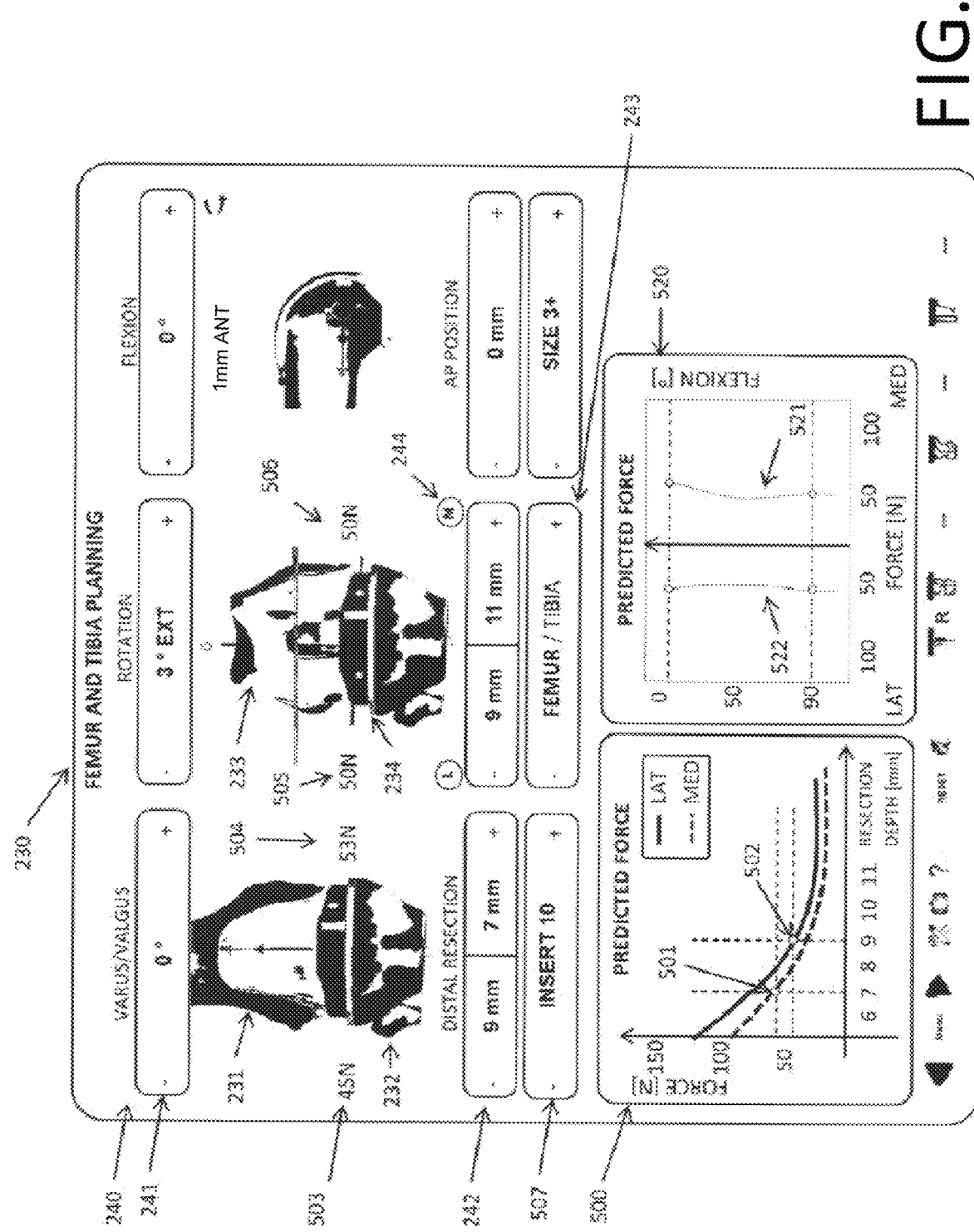
FIG. 10C is screen shot view of a femoral and tibial planning user interface in accordance with an aspect of the computer aided orthopedic surgery system.

The CAOS system also has the capability of providing predictive force data that is indicative of the amount of force acting in the joint and on the implant as a result of a specific implant plan. FIG. 10C illustrates an exemplary implant planning user interface. The interface includes predictive force information and data indicative of the forces acting on the knee implant 503, 504, 505, 506, 500, 520. Based off the force-elongation curve 271 measured in the knee with the ligament balancer, a relationship between measured force and elongation of the soft tissues surrounding the knee (or relationship between force and the relative positions of the tibia and femur) is known on both the medial and lateral side at any particular flexion angle. The elongation measurement can be computed using either the motion controller of the ligament balancer or the 3D tracking system. This relationship can then be then used to calculate and predicted forces as a function of the planned implant sizes and locations in the bone, as well as the bone resection depths 500. The bone resection depths and angles determine where the implants will be positioned on the bone, and the thickness of the implant in each area determines how much material will be added or removed in the joint in relation to the original native joint surface. It can be assumed that the tibial and femoral implants will articulate (be in contact) with one another once implanted, and thus the implant positions in each bone will then define the relative positions of the bones after implantation. This relative bone positions post-implantation is used to determine the ligaments' new lengths at that position, or how much elongation the ligaments and soft-tissues undergo in comparison to the pre-implantation state when the force versus elongation measurement was taken. Thus the initially measured force versus elongation relationship is used to determine the predict force which is dependent on the planned location and size of the implants and bone cuts.

The following is an example of how the force may be estimated. A force elongation curve 271 (FIG. 5A) is acquired in extension on the medial and lateral side with the ligament balancer. The gaps measured for the force elongation curve on the medial and lateral sides could be based on a distance between a fixed point on the femur and a fixed point on the tibia, for example the insertion point of the medial or lateral collateral ligaments. Thus a reference position (or gap) between a tibia and femur is defined both in 3D space and on the force vs. elongation curve (for example 18 mm on the curve). There is a reference force associated with reference position, according the measured force elongation curve.

Now, the tibial and femoral implants may be planned such that their locations relative to their respective bone is known, for instance, by planning the depths of the resections, such as the depth of the distal femoral resection on the medial (7 mm) and lateral (8 mm) side 242. It is assumed that the tibia and femoral implant will be engaged or articulating with one another such that there is contact between the femur and tibia on the medial and lateral sides and the overall combined thickness is known. For example, if the tibial implant is 10 mm thick 507 at its lowest point on the plateau and the femoral implant is 9 mm thick at the thickest part of its distal aspect, i.e., perpendicular to the distal resection, then the total combined thickness is 19 mm in extension. Now, based off of the planned location of the implants in the femur and the tibia, and the total combined thickness of the femoral and tibial implants, a virtual gap value may be calculated (based off how much the implant thickness at its current cut location will spread apart the joint) and compared with the known acquired reference position or gap. The difference between the known reference position and the virtual gap will determine the amount of elongation from the reference position and hence the amount of force from the reference force (which is determined from the force elongation curve). Thus as the surgeon adjusts the plan by increasing the insert thickness, or decreasing the depth of bone resection on the tibia or the on femur, this will increase the virtual gap values 503 and 504 and predict higher residual forces using the force-elongation curve 500. If too much bone is removed or the insert thickness is too small, the predicted force may drop to zero or close to zero as soon as the ligaments are no longer in tension.

The CAOS system also has the capability of predicting the force between the tibia and femur implants throughout a range of joint motion, and particularly through a range of flexion 520. A force-elongation curve can be acquired in a single degree of flexion (for example in extension), and that force-elongation relationship can be applied at every degree of flexion to calculate the predicted force on the medial side 521 and lateral side 522 throughout flexion. Alternatively, to improve the accuracy of the prediction, multiple force elongation curves can be acquired at different flexion angles, for example in extension (around 0 degrees flexion) and in flexion (around 90 degrees flexion) and the force-elongation data can be interpolated across the flexion angle on the medial and lateral side to calculate the predicted force at intermediate flexion angles between 0 and 90. Additional acquisitions can be acquired in mid-flexion and to further improve accuracy and to have additional points to interpolate between. Forces can also be extrapolated to hyper extension or deep flexion, and can include factors to better predict the non-linear behavior at the extreme positions due to biomechanical factors such as tensioning of the posterior capsule as the knee is brought into hyper extension.

Once the surgeon has selected a suitable implant placement they can validate their plan and proceed to resect the bones to install the implant components according to the validated plan. Validating the plan includes defining a set of targeted bone resections. In order to perform the resections, cutting guides may be navigated into the targeted cut positions using the 3D tracking system. Alternatively, a robot 8, such as a robotic cutting guide, or a robotic-assisted arm that guides cutting tools (burrs, saws, and the like), may be used to perform the cuts according to the plan. After the resections are performed, the position of the final resection can be measured and stored using the tracked cut controller.

Input to Patient Specific Dynamic Model

The CAOS system can also include a dynamic biomechanical model of the patient that can be used to predict the post-operative joint kinematics and dynamics according certain surgical input parameters, such as the planned position, alignment and size of the implant components, as well as force-displacement data collected by the ligament balancer. Predicting the post-op joint kinematics means that the positional relationship between the tibia and femur (and optionally the patella), and their respective implants, is determined over a range of joint motion, such as flexion. Predicted kinematic parameters over a range of flexion can include joint angles (e.g., varus/valgus, internal/external rotation), femoral rollback on the tibia, and femoral condylar lift-off from the tibia. Predicting the post-operative joint dynamics means that the forces acting between the implant components, and optionally between the implants and bones and in the surrounding soft-tissues, are predicted. Inputs into the model can include the flexion angle, muscle loads, and anatomic structure geometries and properties. The dynamic biomechanical model includes 3D geometry data of the bones, and information about the soft-tissues surrounding the joint, including ligaments (MCL, LCL, PCL), joint capsule, muscles (quadriceps, hamstrings) and tendons (patellar tendons). Soft-tissue information can include the attachment sites and lengths of ligaments, tendons, and muscles, including geometry, volume, and cross-sectional areas. The model can be a dynamic model of a knee joint or entire leg or lower skeleton that is capable of modelling or predicting the kinematics and dynamics of the knee joint during certain functional activities, such as a deep knee bend, stair climbing, and so on. The model can include assumptions about soft-tissues characteristics (muscle activation forces, effective soft-tissue stiffness, Young's modules, visco-elastic properties) that cannot be measured easily intra-operatively. Certain properties can be determined from pre-operative data, such as image data taken from a pre-operative scan, such as a CT or MRI scan. Pre-operative data can include static data such as measurement of the relative positions of bones at a specific moment in time during various activities, such as standing, getting out of a chair, stair climbing, using imaging techniques such as 2D or 3D x-rays, ultrasound, etc. The model can simulate an activity such as a deep knee bend by simulating muscle loads such as the quadriceps and hamstrings which apply forces to each bone at their attachments sites along the direction of the muscle. Contact loads can be calculated between the tibia and femur and femur and patella. Reaction forces such as ground reaction forces can be predicted based on the patient overall mass, weight, height. Masses of individual body segments may be estimated using tables of known values based off of measurements taken from a sample population of humans. Pre-operative dynamic data such as joint and body motion kinematics and gait analysis with ground reaction forces can be also be as inputs. In the present invention, the ligament balancer is inserted in the knee and run through a displacement cycle from a lower to higher position and measures the displacement—force relationship of the soft tissues surround the joint. This can be done individually for the medial and lateral side, or together on both sides. The force—displacement relationship are then used as inputs to the knee model to more accurately predict the kinematic and dynamics of the knee based of a selected component placement, and thereby optimize the placement of the component by selecting the placement that produces the most desirable kinematics and dynamics.

Asymmetric Functionality

The active ligament balancing system can also have asymmetric control characteristics. For example, during certain modes of use, such as during a varus valgus stress test, one of the femoral condyles may be lifting off the articulating surface of the corresponding upper paddle when on the other side the condyle is in contact and applying a force on the paddle. In this case it may be desirable to measure the gap on the opposing side of the joint (i.e., the side that is lifting off the paddle), while maintaining a constant height on the opposite side. This can be measured by the 3D tracking (CAOS) system, however, in some cases it is desirable to get the values directly from the distractor rather than from the CAOS system (for example, if the line of sight between the 3D positioning measurement system (optical camera) and the bone trackers is obstructed or if the distractor is being operated in a stand-alone mode). In this case the distractor may have different control strategies applied to the left and right side, wherein the side that is measuring the height is allowed to move upward with a given force that is high enough to maintain contact with the condyle but not large enough to apply significant tension to the ligaments. Thus the compressive force being applied between the tibia and femur during a varus/valgus stress test can be captured on one side of the distractor that is being controlled to a constant height, while height of the opposite compartment can be measured by controlling the distraction force of the distractor.

Post-Resection Stability Assessment

The CAOS system also has the capability of assisting in the assessment of the joint after the resections are performed. Here, the surgeon can use the system to evaluate the residual tension in the joint for different available thicknesses of the tibial insert. The ligament balancer can be assembled with the appropriate lower paddle 12, upper paddles, 21, 23, and augments 42, 44 that match the size of the tibial baseplate and tibial insert that is to be implanted. Once assembled, the ligament balancer is inserted in the knee and used in height control mode, where the height of the ligament balancer is controlled to match each of the available insert heights in the implant system to be installed.

FIG. 10A shows an example of a user interface that is displayed during the post-resection assessment. The interface includes frontal 343 and sagittal 344 views of the femur and tibia 3D bone models complete with resections and implants installed on them, and the position of the femur relative to the tibia is displayed in real time according to the tracked position of the femur and tibia. The locations of the implants on the bones can be determined either by their planned locations, or by the locations of the measured resections, or by digitizing the implant directly. The interface also includes the real-time display of the degree of overall alignment 320, degree of knee flexion 321, and medial 326 and lateral 327 gap values, which may also be represented graphically on the models in the frontal view 334, 335 and sagittal view. The amount of force acting on the medial 322 and lateral 323 sides may also be shown. A color coded bar 311, colored text, meter, or other graphical objects may be included to highlight the magnitude of the force being applied to the ligament balancer.

The interface may also include a graph 300 that plots out the overall alignment 303 (real time, mean, max varus and max valgus), and the medial 345 and lateral 346 forces being measured by the ligament balancer as a function of flexion. Medial and lateral gap values may also be included on the graph. Thus the surgeon can take the knee through a range of flexion and plot out and assess the forces acting on the ligament balancer (which is now acting as a virtual implant or virtual trial implant) as well as the joint kinematics throughout a range of flexion. The force curves 345, 346 may also be color coded to draw attention to the whether the measured force is relatively high or low. Reference lines 347 may be included on the chart to depict the initially targeted force during the ligament balancing steps to allow for easy comparison. The color coding of the force curves could be relative to the initial force applied during the ligament balancing stage.

For example if a specific force profile was applied as a function of flexion, the difference between the measured force during the post-resection assessment and the applied force during the ligament balancing step (before resecting the femur) could drive the color coding scheme, where values of higher force (for example 10 N, 20 N, 30 N, 40 N, 50 N higher) than the initially applied force are colored in progressive shades of yellow, orange, and red in the color spectrum, to signify a knee that is increasing tighter than planned. Progressively lower force values that signify less tension or a looser knee, may be similarly color coded, for example from green to blue.

Alternatively, color may be used to signify the amount of force imbalance from medial to lateral at different degrees of flexion. For instance, if the medial force is greater than the lateral force by a threshold value (for example, 50 N), or vice versa, the curves or values may be highlighted to draw attention to the amount of imbalance. The absolute amount of force may also be used to set the color code (for example, all forces >100 N are orange, >150 red, and so on). Alternatively, the reference lines 347 and the color coding scheme can be based on the predicted force that was predicted during the implant planning stage of the procedure.

The gap values may also be color coded as previously described. An insert height button 340 can be used to change and control the height of the ligament balancer such that the height of the ligament balancer matches the height of the tibial insert being evaluated. Thus by pressing the insert button 340 on the screen or via the remote control, the surgeon can simulate different tibial implant thicknesses (or insert heights) and immediately evaluate the change in forces acting on the ligament balancer due to the increasing or decreasing tension in the ligaments, and based on the force, gap, and alignment measurements presented on the user interface, can select the most appropriate tibial insert thickness to use for this specific patient. Thus the ligament balancer can replicate and entire range of insert thicknesses and sizes while not requiring the large number of different sizes or thicknesses of components that are normally required in manual surgery.

The ligament balancer may also be controlled in increments of height that are finer than the available inserts thicknesses, for example in 1 mm or 0.5 mm increments. Thus if the surgeon finds that an in-between thickness provides the best result, they may go back and further resect the tibia by the difference between the preferred intermediate thickness and the next available implant thickness to allow for the next size up of insert thickness to be used. For example, if tibial implants are available in 14 mm and 16 mm thicknesses, but the surgeon finds a 15 mm thickness provides the best result in terms of tension and stability, they can go back and recut the tibia by 1 mm, thus making room for the 16 mm insert yet obtain the force characteristics of the 15 mm insert.

In other words, the height of the ligament balancer is controllable in discrete increments of height, such as millimeters or increments thereof. The height of the ligament balancer can be set to a thickness that is in between the available tibial implant thicknesses of the implant system. The foregoing allows for the next thicker size of implant from the height set to be selected and fitted to the patient by recutting the tibia by the difference between the next thicker size and the in between set height.

The surgeon can also use the ligament balancer and user interface to assess the post-resection stability of the joint, during for example a varus/valgus stress test. With the ligament balancer being controlled in height mode, the surgeon may apply a varus stress and a valgus stress to the tibia or ankle to evaluate the amount of opening in the gaps 326 and 327 and change in the overall alignment 320 under the applied stress. The real time force values 322 and 323 can be used to control and standardize the amount of stress (varus or valgus force) being applied by the surgeon, as previously described, and this can be performed at different angles of flexion and with different insert thicknesses.

If the surgeon finds that force being measured on the medial or lateral side is overly high while taking the leg through a neutral range of flexion (i.e., while not applying a varus or valgus stress), the surgeon may use this information to perform releases on the ligaments or recuts of the bone and different angles or locations depending on the force information being displayed (value, location, range of flexion). Performing a tibial or femoral recut at a slightly different angle (for example 1 or 2 degrees) allows additional laxity to be introduced on either the medial or lateral side (for example if more bone is removed medially or laterally, respectively), or the tibia may be resected with more slope to increase the flexion gap, or less slope to increase the extension gap. Alternatively the distal femur may be recut to increase the extension gap and gain more extension of the leg when there is an extension deficit.

The ligament balancer may also be operated in a force control mode during the post-resection assessment step, by pressing a button on the screen that switches the ligament balancer from the constant height to the constant force mode. As shown in FIG. 10B, tension 322, 323 is actively applied to the medial and lateral side of the joint according to the targeted force entered using the onscreen buttons 306, or stored in the user's profile of preferred settings, and the medial and lateral gaps between the femur and tibia 307, 309, can be monitored in real time and plotted 350, 351 against flexion. If the gap (tibial bone cut to femoral implant gap, or tibial implant to femoral implant gap) is too small relative to the desired gap, ligament releases can be performed to open up and achieve the desired gap. Soft tissues may be released progressively in preferred sequences, while monitoring the change in gap (force mode) or change in force (height mode) in real time, thereby helping to reduce the risk of over-releasing a structure. Needles, small scalpel blades, and the like can be used to more precisely control the release process.

The system is also has the ability of estimating or determining the location of the contact force acting between the bearing surfaces of the implant, based on the location of the femoral component relative to the tibial component as measured by the 3D tracking system. Collision or contact detection software or similar algorithms can be used to detect where the femoral implant model is in contact with the tibial implant model. The implant model files are typically 3D geometrical mesh models with vertices and edges arranged as facets to form a solid or surface model.

One method of determining the contact point is to search for a point or area of intersection between the two models. The algorithm can also search for zones of overlap between the femoral and tibial implant models and defer based on the degree or shape of the area or volume of overlap the location of a contact point or contact area between the tibial and femoral implants. The shortest distance between points on the surface of the tibial model to points on the surface of the femoral model (i.e., a closest point algorithm) may also be used. Knowing the material properties of the implants (such as Young's modulus), the measured forces, and contact locations or areas, the amount of stress acting on the tibial insert may also be calculated and estimated.

A finite element model may also be used to calculate the stresses acting on the tibial insert based on the measured loads and contact areas or patterns. The user interface may include a top view of the tibial implant (i.e., view aligned with the proximal-distal direction) to better illustrate the location of the force or forces (or contact points) on the tibial implant plateaus or articulating contact surfaces, as well as the predicted stresses acting on the implant surface. Thus the surgeon may assess the contact pattern, contact forces, and/or contact stresses of the femur on the tibia as they are bringing the knee throughout a range of flexion.

Thus the CAOS system allows the user to visualize the contact patterns and they may look for specific contact or loading patterns that are indicative of a normal or favorable kinematic or dynamic outcome, such as a pattern depicting the femur rolling back on the tibia with flexion, where the femoral-tibial contact point translates posteriorly on the tibia as the knee is flexed, particularly on the lateral side or proportionally greater on the lateral side than the medial side.

Alternatively, they may visualize paradoxical motion such as anterior translation of the femur on the tibia with increasing knee flexion, and may decide to make a change to the position of the implants, or release certain soft tissues as a result. Changes may include adjusting the rotation and/or position of the tibia on the tibial cut, by repositioning the ligament balancer on the tibial cut, and re-evaluating. Thus the system may also be used to optimize or adjust implant positioning during the post-resection assessment (or virtual trialing) phase.

As previously mentioned, the CAOS system may be used to determine the optimal rotation and/or positon of the tibial component. For example, after the femoral component has been inserted and the surgeon is performing a post-resection assessment, the load imbalance between the medial and lateral side during a flexion motion may be evaluated and if an imbalance is detected the position (rotation, or AP or ML position) of the ligament balancer on the tibial resection can be changed and the assessment re-performed to see if the force imbalance improves.

Additionally, the location of the contact areas or points of the femur on the tibia can be used to determine if the tibial baseplate needs to be repositioned. For example, if the contact points do not remain near the bottom of the dishes of the tibial implant but ride up the dishes and to one side as the knee is brought in to extension, it may be due to a suboptimal rotational positon of the tibial insert with respect to the tibial cut and femoral implant (tibial-femoral mismatch). In another embodiment, the ligament balancer may be configured to facilitate rotation and/or sliding of the lower paddle on the tibial cut surface. The bottom surface 13 of the lower paddle 12 may be adapted to rotate and or slide on the tibial cut surface, by for example incorporating a low-friction surface, such as a polished surface.

Figure 12A:
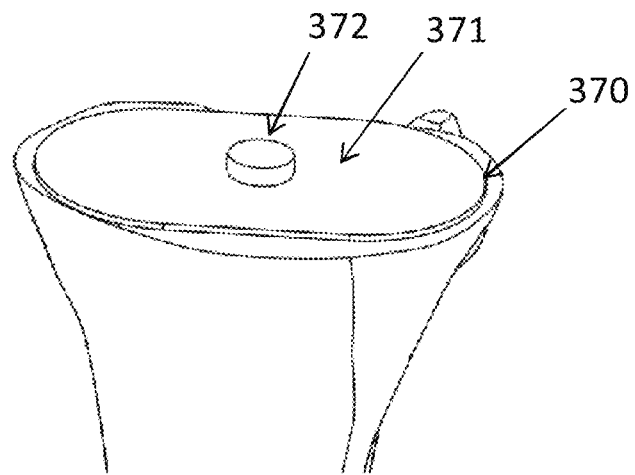
FIG. 12A-D are views showing the operation of the lower paddle being fixed to the tibia while allowing for rotation and/or translation of the lower paddle and ligament balancer relative to the tibia.

Alternatively, as shown in FIG. 12A, an intermediate part 370, that acts as a bushing, or a sliding surface for the lower paddle 12, may be placed on the cut surface 110. The intermediate part 370 has a low-friction surface 371 for the bottom surface 13 of the lower paddle 12 to more effortlessly rotate and/or slide on. The bearing surface may include a feature, such as a cylinder 372, that mates with a feature on the lower paddle, such as a central hole 373, to constrain the rotation of the lower paddle about an axis. The thickness of the bushing or intermediate part 370 may be compensated for by making the lower paddle thinner, or by adjusting the height between the upper and lower paddles of the ligament balancer automatically via the computer's software.

Figure 12B:
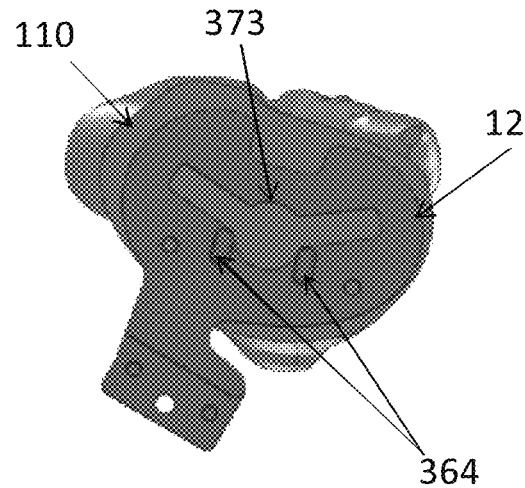
Figure 12C:
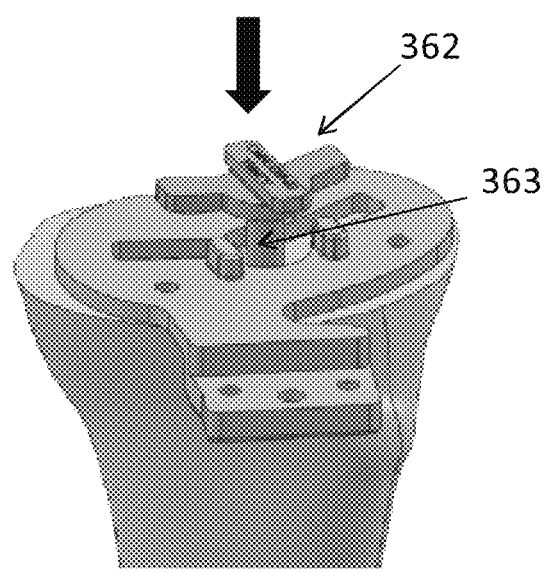
Figure 12D:
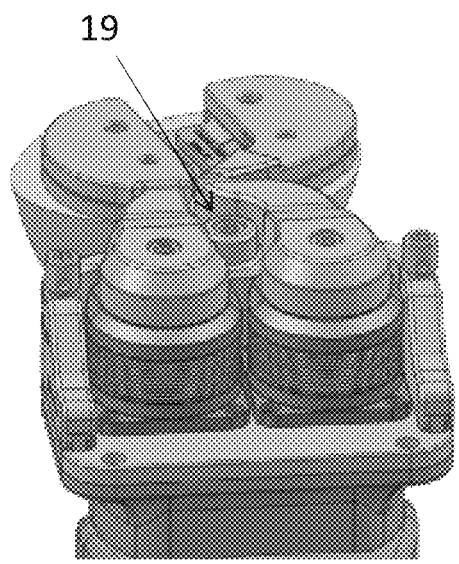

FIGS. 12B-D show another example of how the ligament balancer may be configured to rotate on the tibial cut surface. In FIG. 12B, the lower paddle 12 is initially positioned on tibial cut surface 110. A rotating bushing 362 that is intended to allow rotation of the lower paddle 12 relative to the tibia is coupled to the lower paddle 12. The rotating bushing 362 may have a distal portion 363 that is intended to be inserted into the bone, and permit rotation of the bushing and the lower paddle relative to the bone via a cylindrical surface. A drill or punch may be used to create a cavity in the bone for the bushing, and the cavity may coincide with the final cavity that will be created for the tibial stem or keel. A drill or punch guide may positioned on the lower paddle and be used to guide the drill so the cavity created coincides with the bushing.

As shown in FIG. 12D, once the rotating bushing is attached, the ligament balancer may be attached to the lower paddle 12 via the attachment screw 19. The ligament balancer can be operated in force control mode, where it is applying a force to the femur and during a knee flexion motion, the balancer rotates and/or slides under the anterior and posterior and/or sheer forces imposed by the femoral trial component or implant on the augments 42, 44 of the ligament balancer, causing the balancer to find a preferred position on the tibia as a result of the loads. The ligament balancer can be also operated in height control mode, and during a knee flexion motion, the balancer rotates and/or slides under the sheer forces imposed by the femoral trial component caused by the tension of the ligaments, causing the balancer to find a preferred position on the tibia. Alternatively, the balancer may stay in position on the tibial cut but may be manually moved or rotated on the cut based on the observed measurements and iteratively positioned and re-evaluated until the surgeon is satisfied with the displayed measurements. Once the preferred position on the tibia is found, the position of the lower paddle may be marked on the tibia, for example using a surgical ink marker. The lower paddle may be fixed, and the cavity for the tibial keel can be created to fix the final position of the implant. Alternatively, as previously mentioned, the position of the ligament balancer may be tracked by attaching a reference marker and tracking it's position during the range of motion, and it's final preferred position stored in the computer. The range of motion or rotation of ligament balancer with respect to the tibia and femur can be tracked and displayed, and the final preferred position may be determined from the tracked motion pattern, for example in the middle of the extreme ranges of internal and external tibial rotation during the range of motion.

Examples

Several scenarios of how the CAOS system can be used clinically are described below.

Figure 13A:
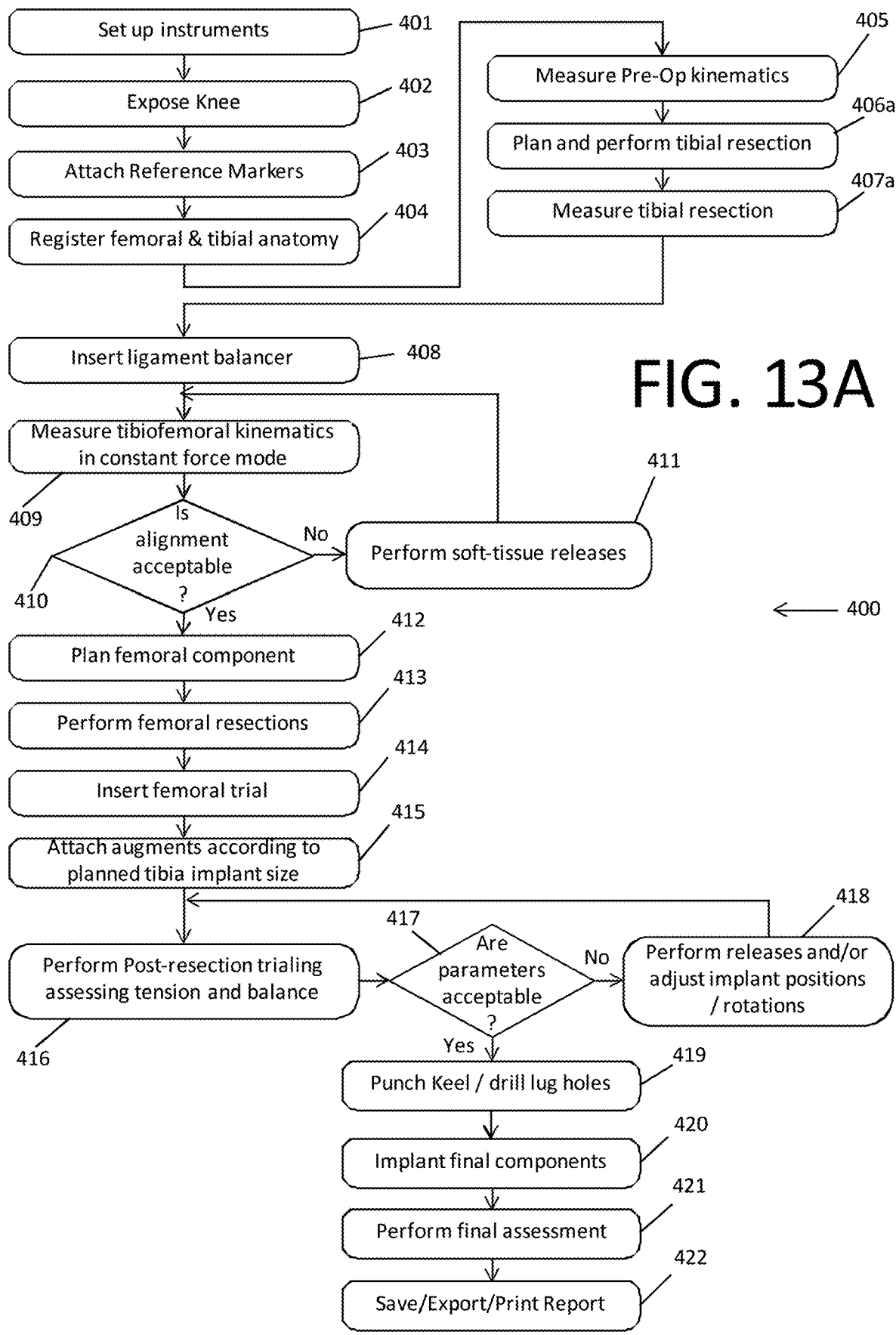
FIG. 13A shows a process flow chart overview of the computer aided orthopedic surgery system in accordance with an aspect, used in a tibial cut first ligament balancing technique.

A) FIG. 13 shows a process flow chart overview 400 of how the CAOS system may be used in a tibial cut first ligament balancing technique (dependent cuts, navigated).

401 Set-up instruments: Assemble and calibrate instruments, assemble ligament balancer 1 with appropriate size and side (left or right) of upper 21, 23 and lower 12 paddles, and home the ligament balancer (note the ligament balancer may also be assembled and/or homed later in the procedure as described below).

402 Expose knee joint, remove osteophytes.

403 Attach a reference markers 106, 107 to the femur 100 and to the tibia 105 to permit tracking of the femur and tibia with the 3D tracking system 2.

404 Register anatomy of proximal tibia 105 and distal femur 100 and of tibial mechanical axis and femoral mechanical axis, creating a model of the tibial bone and model of the femoral bone. As previously mentioned, the models are preferable created using image free means, such as by deforming one or more generic bone models to the points acquired on the bone surface. However any means for creating and registering a model may be used, including image-based means that use models derived from pre-operative images such as CT, MRI or X-rays.

405 Measure pre-operative kinematics of the leg by taking the knee through a range of motion and measuring by displaying in real time and storing the overall alignment of the mechanical axis (varus and valgus) as a function of the knee flexion angle (FIG. 9A). The pre-op kinematic measurements may also include the following measurements: the knee flexion angles including maximum extension and maximum flexion, maximum varus angle and maximum valgus angle and medial and lateral gap values between the tibia and the femur throughout the range of flexion or at specific flexion angles, while applying a varus stress and a valgus stress, throughout the range of flexion (average, minimum, and/or maximum), internal/external rotation of the femur with respect to the tibia. Preliminary releases may be conducted at this stage to address a significant deformity.

406a Plan tibial resection using tibial bone model and/or acquired points on the tibia. The tibial resection planning parameters include medial and lateral cut depths, cut slope angle, cut varus/valgus angle. Planning may also include internal/external rotation, medial/lateral and anterior-posterior positioning. Note this tibial planning step may be omitted and the user can proceed directly to using the displayed real-time navigation values of the position of the tibial cutting guide relative to the tibia.

406a Track position of the tibial cutting guide relative to the tibial bone to achieve targeted (planned) position, fix position of cutting guide relative to the tibial bone. Adjust (fine tune) position to more closely match target if using an adjustable cutting guide. Note a robotically positioned cutting guide may also be used.

406a Perform tibial resection using positioned cutting guide, remove resected proximal plateau of tibia, remove guide.

407a Measure the 3D location and angle (cutting depth, slope, varus/valgus) of the tibial cut with respect to tibia using the cut controller probe and store in computer.

Size tibia using array of lower paddles as templates. The cut surface of the tibia or the cut surface of the removed proximal plateau of the tibia can be used to determine the best size by overlaying one or more of the different sizes of lower paddles 12. The appropriate size can be attached to the ligament balancer 1 using the attachment interface 16. Alternatively, the size can be determined from the tibial bone computer model, which may be the same model that is used to plan the tibial resection, or the points acquired on the tibial bone surface. The femoral bone model can also be used to determine the most appropriate size of upper paddles to be used. This can be accomplished by automatically measuring on the model the medial-lateral size of the femur in the vicinity of the articulating surface of the femur and/or tibia, for example using the medial lateral distance or absolute distance between the most distal points on the medial and lateral femoral condyles, or between the most posterior points on the medial and lateral femoral condyles, or both. Similarly, the distance between the most prominent points on the medial and the lateral condyles (apexes of the condylar surfaces) from an extension position to a flexion position (for example between 0 and 90 degrees of flexion) can be calculated (i.e., the areas of the condyles that would contact the contact surfaces 22, 24, of the upper paddles 21, 23).

Alternately, the femur or tibia bone models may be initially sized with a femoral or tibial implant by the computer and the determined implant sizes can be used to determine which size of upper or lower paddles to attach to the ligament balancer. This allows the surgeon assistant who is assembling the ligament balancer on the back table to know precisely what size of attachments to use before passing the ligament balancer to the surgeon, thus not requiring a pre-operative image to determine the most appropriate sizes of the attachments. The ligament balancer may be homed at this stage if it has not already been homed.

408 Insert the ligament balancer, which is preferably in a retracted position and may be in a disabled or back-drivable state, in the knee such that the lower surface 13 of the lower paddle 12 rests on the resected surface 110 of the tibia 105, the rotation of the ligament balancer and the lower paddle can be set on the tibial resection such that the lower paddle provides a good anatomical fit to the tibia, i.e. the size and rotation of the lower paddle (the contour of the lower paddle matches the contour of the tibial implant baseplate) is set so that it closely matches the contour of the tibial resection. The rotation of the ligament balancer can also be established later in the procedure, (i.e., after planning and resecting the femur), and the positioning of the ligament balancer on the tibial resection at this stage can be done just in a preliminary manner such that it is in an approximate position and the upper paddles do not interfere with the patellar tendon and other soft tissues during the gap acquisitions throughout the range of flexion.

409 Gap acquisition under force control: With the leg in extension, start the ligament balancer in force control mode by pressing a button on the display or remote control (for example, by pressing a start button 108 directly on the ligament balancer, a go forward or engage button 330 on the display user interface (FIG. 9B), or holding down a button on the footswitch), to apply a constant force in the knee joint on the medial and lateral side. The amount of force initially set can be based on the settings programmed into the surgeon's user profile, and the values may be different for extension and flexion. The applied forces may also be adjusted in real time using the buttons 329 on the display or remote control (e.g., 50-200 N targeted per side, adjustable in increments of 5 or 10 N). Upon pressing start the upper paddles will move up and away from the lower paddle and begin to apply a force between the tibia and femur. Once the targeted force has been reached.

410 is the stage the surgeon can measure the initial limb alignment 320 and assess if the alignment and other parameters are acceptable. If they determine it is not acceptable, they may perform soft tissue and ligament releases 411 as required or desired by the surgeon to bring the limb into neutral mechanical axis alignment or with an acceptable range of parameters, for example, within +/−2 degrees of neutral overall alignment 320.

For instance, if the limb is in a varus alignment in extension of more than two or three degrees, the following structures can be progressively released until the HipKnee-Ankle (HKA) angle 320 is within 2 degrees: Step 1—release of pes anserinus, step 2—release of the deep later of the medial collateral ligament (MCL), step 3—release of superficial layer of MCL, step 4—release of semimembranous tendon. For a valgus deformity, the following soft tissue structures may be released: step 1—iliotibial band, step 2—lateral retinaculum, step 3—LCL from the inside out.

To facilitate a controlled release, a small scalpel blade (such as a no. 15 blade) or preferably a needle and a puncture technique can be used to puncture individual or small bundles of fibers at a time, while monitoring the alignment values in real-time on the display. The needle or scalpel can be inserted between the upper and lower plates to obtain access to the inner medial and lateral side of the knee, for example in the case of a varus or valgus knee, respectively. The distractor will continue to apply a constant force and as the soft-tissues are released the gap will increase, and the surgeon can monitor the increase in the gap as well as the change in overall mechanical alignment of the limb under the force being applied by the ligament balancer. Once an acceptable alignment is reached under the constant applied force, the relative position of femur and tibia in extension is measured by the 3D tracking system and stored in the computer.

409 The surgeon can now reacquire the relative position of the tibia and femur and calculate the gaps between the bones dynamically in extension and/or throughout a range of flexion in force control mode (FIG. 9B) after performing releases. Two gap curves can be generated, one for the medial 301 and one for the lateral 302 compartments.

412 Plan femoral component using the kinematic gap data measured by navigation system in constant force mode 409. The implant gap may be evaluated at several different flexion angles, and the femoral component could be positioned to have a constant gap throughout flexion, or at zero and 90 degrees. Note at this stage if the surgeon cannot find an acceptable compromise between alignment and balance/gaps they can decide to perform additional releases 411, or to recut the tibia, for example to increase or decrease the tibial slope to change the flexion and extension gaps, and the re-assess the tibiofemoral kinematics 409 until an acceptable trade-off is obtained.

413 Once the femoral plan is validated the femoral resections can be performed, using either a robotic cutting guide or manual cutting blocks. The femoral cut surfaces may also be measured with the cut controller, such as the distal cut, anterior cut, and/or all cuts, and their positions stored into the computer.

414 the femoral trial component is then inserted on the prepared femur.

415 the ligament balancer is then assembled with the appropriate augments that match the tibia insert and/or femur to be implanted. Note the augment may be selected to match and articulate with the femoral component, and the implant system may have several available tibial insert sizes that match a specific combination of femoral components and tibial baseplate components. For example, some tibial baseplates will accept one size (the corresponding size) of tibial insert, plus one size up and one size down to allow for matching of the femoral component when there is a mismatch of up to one size between the femur and tibia. Other tibial baseplates are designed to accept any size of tibial insert so that the tibia insert always matches the femur and any size of femur may be selected to fit the femoral anatomy of the patient (see for example the OMNI APEX Knee system by OMNIlife science, Inc. of East Taunton, MA). Other tibial baseplates are compatible with only one size of insert, that size of insert is designed to articulate with multiple sizes of femoral components. At this stage the appropriate lower paddle size can be determined and attached to the ligament balancer if not done so already.

416 The post resection stability assessment (FIGS. 10A and 10B) is then performed. After inserting the ligament balancer (if it was previously removed), the surgeon can evaluate a given tibial insert thickness and assess the tension (forces 345, 347, 322, 323) acting on the insert and the corresponding knee gaps 326, 327 throughout flexion. The ligament balancer is preferably in height control mode and its height is automatically set to match the insert thickness according to the plan. The ligament balancer may start from a low positon to facilitate insertion in the knee, such as the thinnest available insert thickness, or a lowest possible position. Different insert thicknesses may be simulated and evaluated by adjusting the insert height with the onscreen buttons 340. The surgeon can directly visualize the change in forces/tension acting on the insert for different insert heights, and they can apply varus and valgus stresses using the forces to control the applied force and assess the opening of the knee throughout flexion. The balance may also be assessed in force control mode (FIG. 10B), where the ligament balancer is applying a constant or programmed force profile throughout flexion and the surgeon evaluates the gaps 309, 352, 353 to achieve the desired gap opening throughout flexion.

The computer or controller, which includes a memory, can also be configured to include a predetermined force profile for having the distraction device apply varying displacement forces throughout a range of motion of the joint. That is the force applied by the distraction device can be configured to vary based on flection angle of the joint. Further, the memory can have stored thereon various predefined force profiles and user preferences for said force profiles.

Figure 11C:
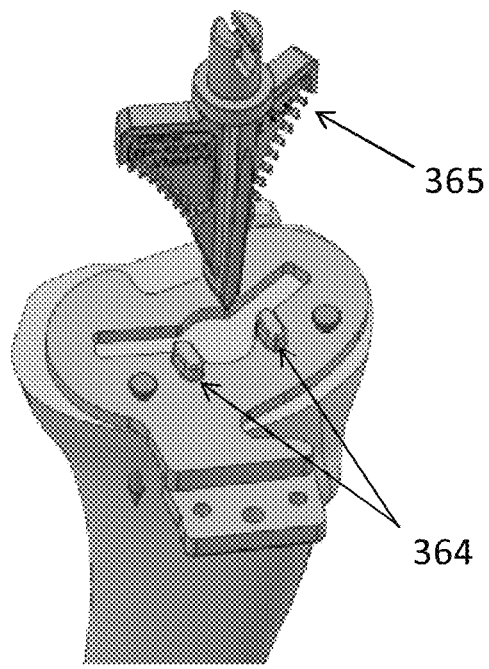
Figure 11D:
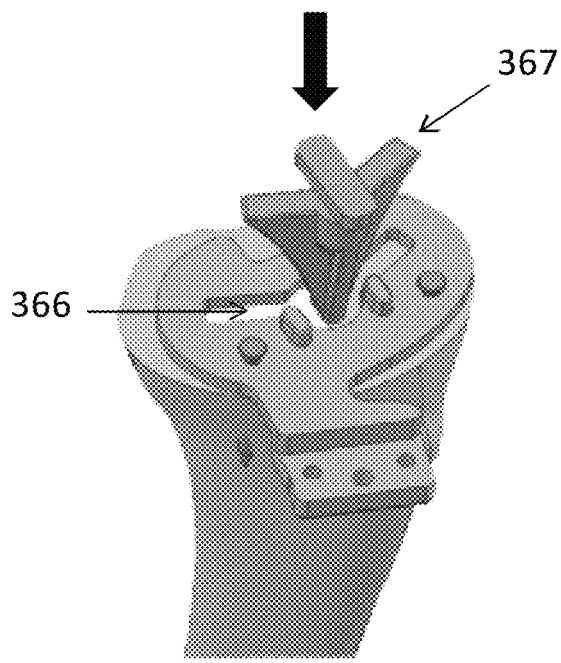
Figure 11E:
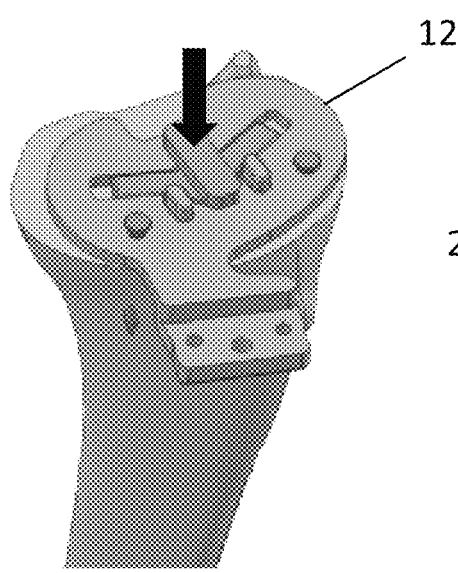
Figure 11F:
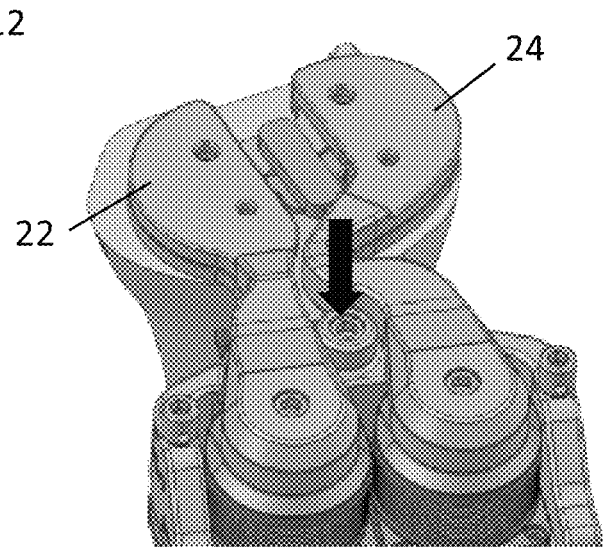

- 417 The surgeon may assess whether the kinematic and gap parameters (final alignment, forces, gaps, contact patterns) are acceptable and if not, they may choose to perform soft-tissue releases or adjust the bone resections 418. Ligaments may be further released depending on the area of tightness and residual deformity, and/or the implant positions and bone resections may be re-planned and re-performed to correct an imbalance. For instance if the forces measured in extension are too high or the knee cannot be brought to full extension, a distal femoral recut may be performed and the femoral implant may be elevated proximally. The femoral component may be downsized to accommodate a tight flexion gap, or the slope of the tibial component may be adjusted and recut. Ligament releases can be performed according to any sequence. The rotation of the tibial component can be assessed by observing the position of the lower paddle on the tibial bone cut and by monitoring the resulting forces, gaps and/or contact patterns during the assessment for any given rotation. The rotation of the ligament balancer with respect to the tibia can be adjusted (with or without the use of an intermediate part 370 or bushing 362) and the results reassessed.
- 419 Once the surgeon is satisfied with the measured parameters and results they can proceed to punch the tibia, creating a cavity for the keel of the tibial implant as previously described and as shown in FIG. 11C. If the femoral component requires additional preparation, such as drilling of lug holes via the trial, then this may also be performed.
- 420 The final implants can be inserted with or without cement, depending on the preferred technique. If cement is used, the ligament balancer may be inserted in the knee in place of the tibial insert and used to control the forces during cementation of the components.
- 421 A final post-op assessment may be performed with the final implants in place (this may also be performed in step 416) and stored in the computer. The final assessment 421 or the post-resection assessment 416 may be compared to the pre-op kinematics 405 or 409, via side by side charts or overlaid charts.
- 422 The final case report is saved and includes all measured parameters, and can be printed or exported to an external storage medium, such as a USB key, emailed to the surgeon, or sent to the hospital network and integrated in the electronic patient record or stored in cloud repository or registry.

Several variations to the above method can be envisioned, including:

Measuring pre-operative gaps and kinematics for a limited subset of flexion angles only, such as at 0 and 90 degrees of flexion.

Lock the height ligament balancer while applying a constant force in extension and/or flexion and assess the stability and feel of the knee at those flexion angles with the height set. Here the height of the ligament balancer can be increased or decreased (339, FIG. 9C) to assess joint stability according to a gap that is planned with a tighter (smaller) or larger (looser) gap accordingly.

A force-elongation acquisition can be performed before, after, or during the ligament balancing phase, and the curves can be used to plan a specific patient tension 275 and that tension can be used to plan the position of the components to achieve the optimal tension. The planning screen could include predicted force or tension curves based off the force elongation measurements and the surgeon can see the effect of component position on the predicted forces/tensions and the gaps. The applied force during the ligament balancing step may be a constant force or a programmed profile where the applied force varies according to the flexion angle.

In sum, the predicted force as a function of the planned gap can be displayed, i.e., measure force elongation (gap) relationship, prep and size using resection information (depth of cut, tangency to bone, etc.), display predicted force (or ligament tension/forces or soft tissue tension/forces) as a function of the planned gap and measured force-elongation relationship. For example, the planning screen can include a display (FIGS. 9B and 9D) of a predicted force on the implant or implant model (e.g., a femoral or tibial implant) as a function of gap spacing, i.e., the spacing between the bones of the joint or flexion angle of the joint, based on the measure force elongation profiles of the joint.

Figure 13B:
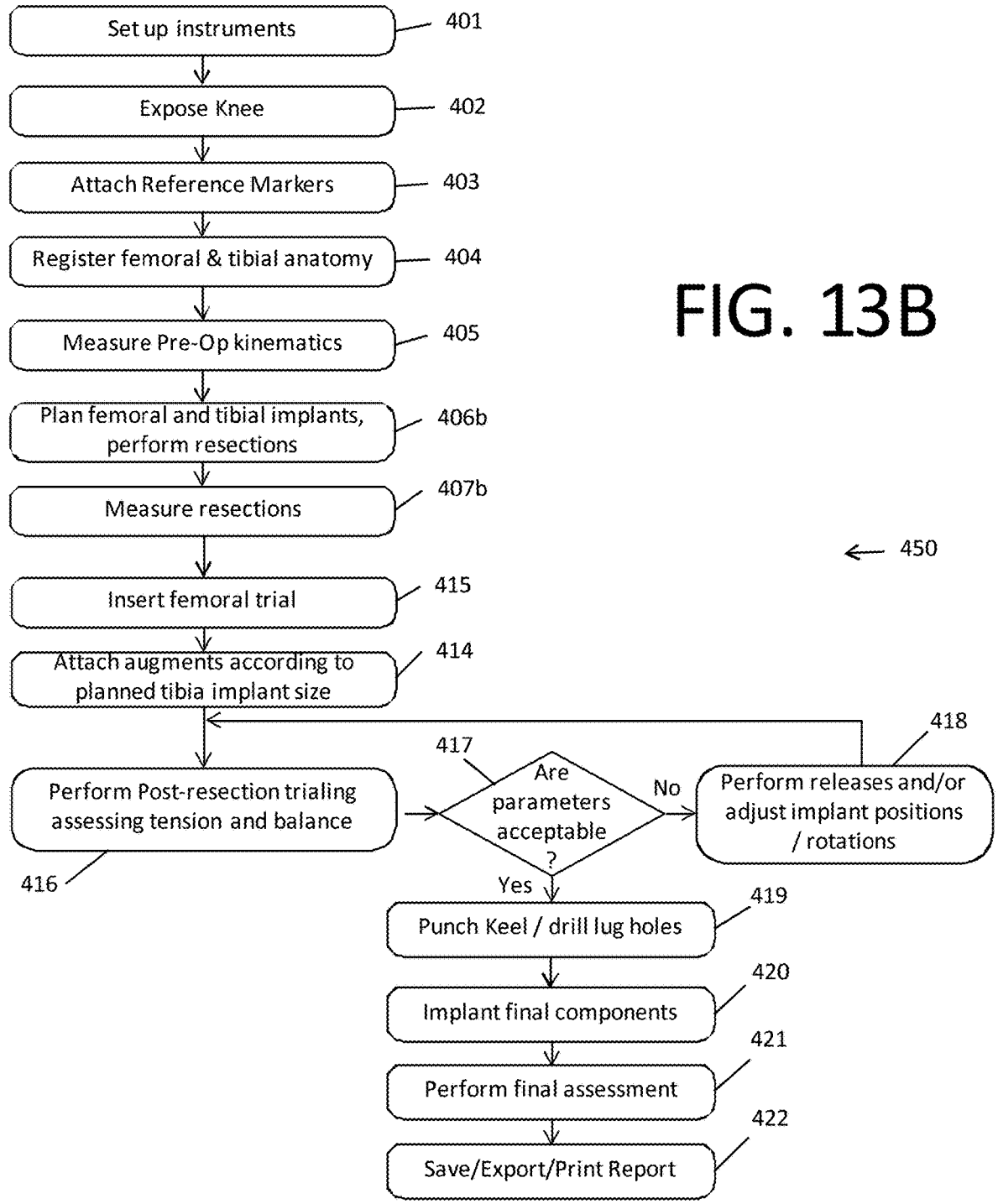
FIG. 13B shows a process flow chart overview of the computer aided orthopedic surgery system in accordance with an aspect; used in a femur cut first technique.

As illustrated in FIG. 13B, another variation of the above method is illustrated. The method 450 includes performing the femoral implant planning and bone resection steps first 406b, followed by the tibial planning and resections 406b, and then to use the ligament balancer for assessing tension and balancing after the resections have been made. In this case, femoral and tibial implant planning may be performed in sequence (i.e., one after another), or simultaneously before proceeding to their respective bone resections, so that the total amount of bone being removed from the tibia and femur may be planned and evaluated. The implant planning may be based on bone anatomy data (measured resections or cut depths and angles with respect to bone anatomical data), as well as pre-op kinematic data (included predicted gaps) acquired before resections are performed 405.

Femur First Ligament Balancing

In accordance with another aspect of the present invention, the orthopedic distraction device 1 is configured to allow the user to plan the position of the implants using both joint gap and bone resection data before making any resections on the bones. In this case, the ligament balancer 1 is configured to distract apart the joint under a controllable load and measure the relative displacement of the joint before any resections are made in the joint.

Figure 14A:
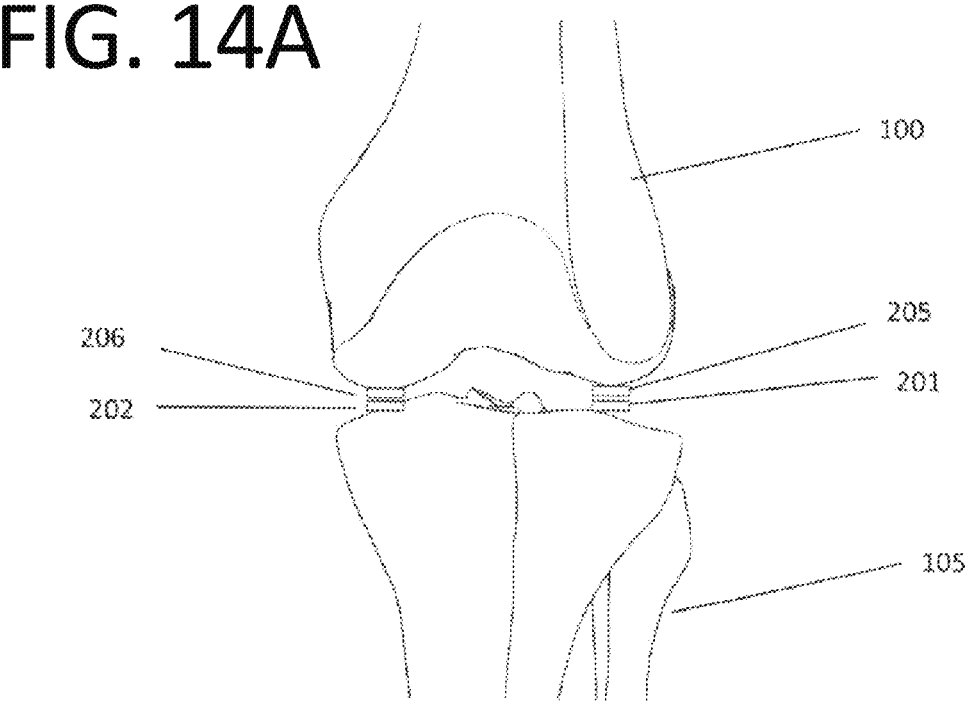
FIG. 14A is a partial view of an orthopedic distraction device in accordance with another preferred embodiment of the present invention inserted within a knee joint.

In another exemplary embodiment, the distractor has upper and lower arms or paddles that are configured to be inserted into the joint prior to making any resections. Referring to FIG. 14A, a frontal view of a femur 100 and tibia 105 in extension is shown, with an upper lateral paddle 205 and lower lateral paddle 201 and upper medial paddle 206 and lower medial paddle 202 inserted in between the uncut tibia and uncut femur. The upper and lower paddles are thin enough such that the minimum combined height of the upper and lower paddles (i.e., when the upper paddle is in the lowest position) is small or thin enough (on the order of 1-4 mm) to allow the device to be inserted into the joint before resections.

Figure 14B:
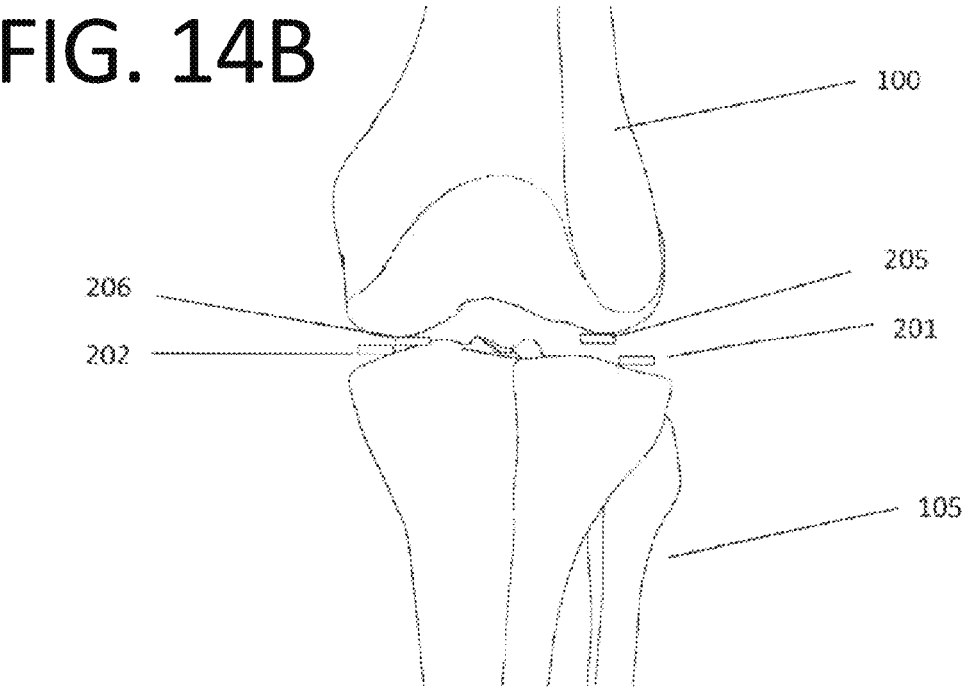
FIG. 14B is a partial view of the orthopedic distraction device of FIG. 14A in accordance with another aspect of the embodiment.
Figure 14C:
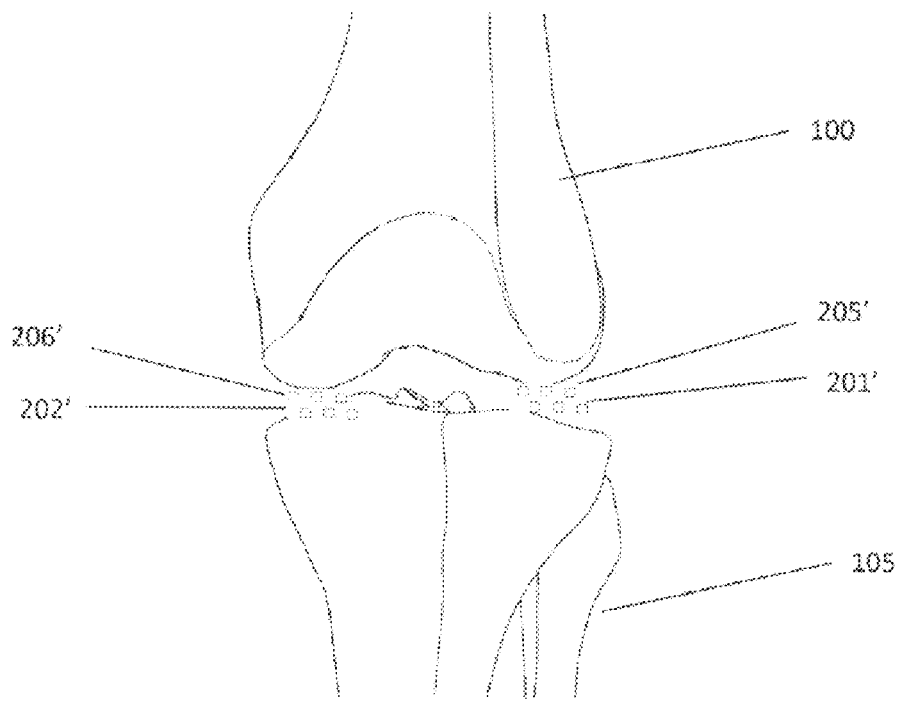
FIG. 14C is a partial view of the orthopedic distraction device of FIG. 14A in accordance with yet another aspect of the embodiment having paddles with a plurality of struts.

FIG. 14B illustrates a different possible arrangement of the paddles in which the upper medial paddle is positioned adjacent to the lower medial paddle in the medial-lateral direction. A similar paddle arrangement is shown on the lateral side. This allows the minimum overall height of the upper and lower paddles to be smaller than that shown in FIG. 14A since there is additional clearance for the upper paddle to be brought down to a lower position (i.e., without interfering with the lower paddle). Additionally, as shown in FIG. 14C, the upper 205', 206' and lower 201', 202' paddles can have several individual 'struts' or tines (like tines of a fork) i.e., a plurality of struts that inter-lie adjacent to one another to maximize the overall surface area where the femur and tibia contact the upper and lower paddles respectively. The arms/paddles may also have a slender and curved profile to allow the distraction with the patella of the knee reduced in the grove of the femur. Although FIGS. 14A and 14B show the knee in extension, the same arrange can be used to measure the gap on the medial and lateral side at any flexion angle, including at 90 degrees of flexion, and through a dynamic range of motion.

Figure 15:
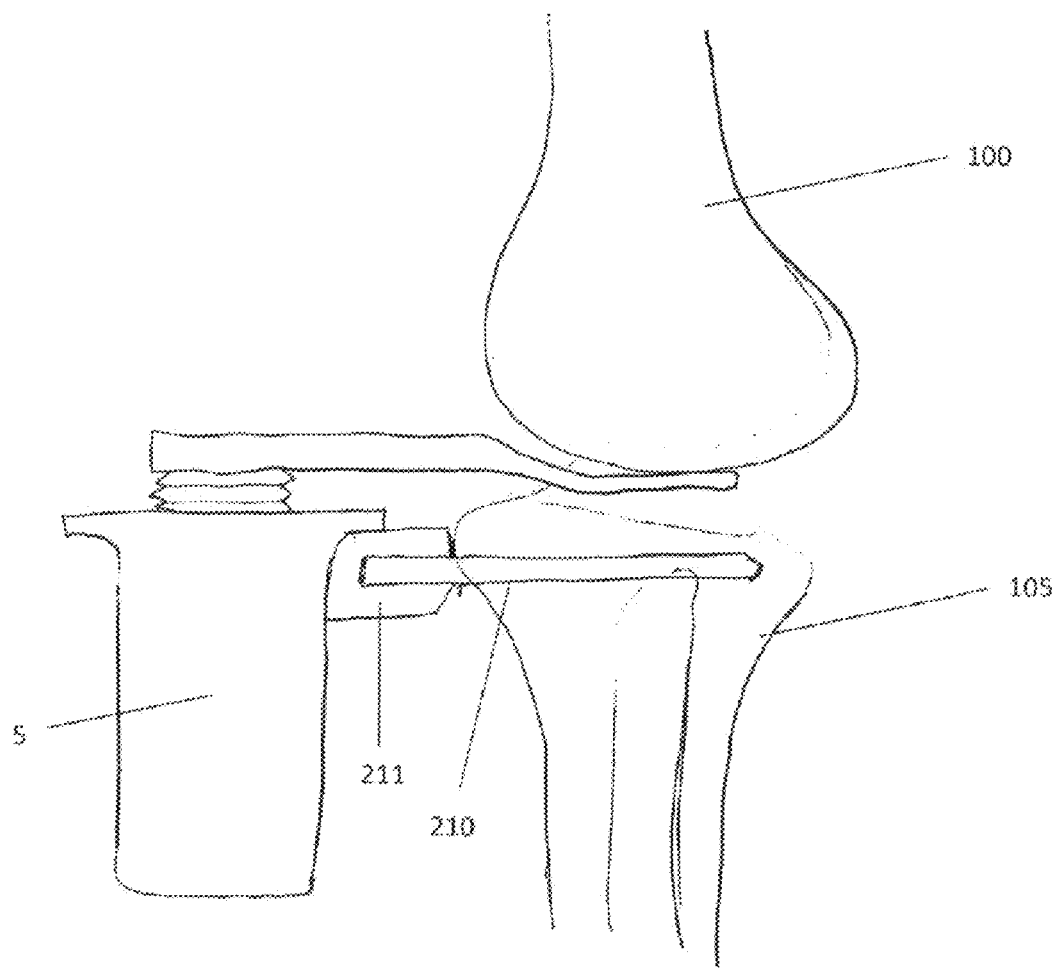
FIG. 15 is a side view of an orthopedic distraction device in accordance with yet another preferred embodiment of the present invention inserted within a knee joint.

FIG. 15 shows another embodiment of the orthopedic distraction device that allows distraction of at least two bones of a joint before making a resection on either side of the joint. Here, the distractor device is fixed to a bone on one side of the joint, for example the tibia 105 of a knee joint, with extra-articular fixation means, such as one or more pins or screws 210. The fixations means may also include a coupling part 211 that allows the displacement mechanism 5 of the distractor to attach to the pins or screws. The coupling part 211 may include a quick coupling mechanism that allows the distractor to attach to the pins quickly and preferably without requiring tools such as a screw driver. The coupling part may be attached to the pins and may have holes for guiding the insertion of the pins. The pins may also be used to support cutting guides for making resections on the bone, for example after the planning of the cuts using the gap data obtained with the distractor. In particular, an adjustable cutting guide wherein the guiding portion of the cutting guide is adjustable relative to a base that is attached to the bone with pins or screws 210 (such as the Nanoblock product marketed by OMNI), can be used. Here, the adjustable cutting guide is attached to the coupling part 211 and used to make the tibial resection.

The graphical user interface 230 shown in FIG. 8 may also be used to simultaneously plan the position of the femoral and tibial components based off predicted gap data. The interface includes representations of the femur 231 and tibia 232, and buttons 241 that allow adjustment of the position of the implant in any direction. Separate buttons can be included adjusting the femur and tibia positions and sizes. Alternatively, a femur/tibia button 243 can be used to toggle between the femur and tibia, allowing the same buttons to be used for both the femur and tibia (i.e. when one of 'femur' or 'tibia' is selected using button 243, pressing the appropriate buttons will change the planned virtual position of the femoral component on the femur or tibial component on the tibia, respectively). When both the femur and tibia are planned on the same interface, the user can directly see the total amount of bone being resected on either side of the joint, thereby evaluating the total amount of bone that will be removed from any compartment of the joint.

As previously described, the predicted gap 250 is the amount of gap or space between the virtual femoral and virtual tibial implants when the implants are planned at their current locations, given the relative positions of the femur and tibial bones as measured during the static or dynamic gap acquisition measurement. Since the static or dynamic acquisitions can be acquired prior to resection of the tibia, the system has the ability to display a predicted medial and lateral gap value as a function of the flexion angle of the knee joint (250, 251, 255) and as a function of the user's planned femoral and tibial implant positions before any resections are made. Thus when changing the position of the femur or tibia on the bone, the user can directly see the effect that these changes have on the predicted medial and lateral gaps. This has the advantage of allowing a user to carry out the femoral resections prior to the tibial resection, while still basing the plan off of the knee gap data.

As an example, the pre-resection gap acquisition and implant planning process may carried out as follows:

Attach reference markers to tibia and femur.

Acquire patient boney anatomy using navigation system (mechanical leg axis, bone morphing/mapping of the exposed anatomical areas of the joint).

Establish a force with which to distract the bones apart and enter into the computer via the control interface.

Insert ligament balancer and acquire the kinematics of the femur relative to the tibia at various degrees of flexion while the distractor is simultaneously distracting the medial and lateral compartments under a preset load (equal or unequal).

Calculate by the computer predicted gap data based on an initial placement of the femoral and tibial implants and display predicted gap data on user interface, this initial placement may be based at least in part from user preference data for implant positioning, and/or from gap data (for example equal implant gaps in extension and flexion, and symmetric gaps from medial to lateral).

Adjust the position of the femur and/or tibial implants on the bones and recalculate the change in the predicted gaps based on the adjusted position Make resections according to the final plan, insert femoral components and tibial baseplate.

Assemble ligament balancer with the corresponding tibial baseplate and augments that match the tibial insert to be inserted in the knee that will articulate with the femoral components to be implanted, reinsert in the knee joint (fixing to tibia as required).

Set ligament balancer to height of corresponding tibial insert to be implanted (for example 10 mm) and assess final balance and soft-tissue tension using force readings and kinematic knee data at various flexion angles using ligament balancer as virtual trial.

In the above described mode, the distractor may be tilted to accommodate varying degrees of joint line tilt due to the tibial and femoral anatomy when it is inserted prior to any resections being performed. Alternatively, the distractor could have a degree of adjustability in the height between the medial and lateral lower paddles to accommodate the different heights of the tibial plateaus.

Several variations to the present invention can be envisioned. The upper arms may have surfaces adapted for articulating with the femoral component directly so that augments do not need to be attached. The medial and lateral gaps can be the heights reported by the ligament balancer instead of the heights measured the 3D position tracking system. The system can be configured to operate in a stand-alone mode that doesn't require a 3D tracking system. Accelerometers and/or gyroscopes can be built directly into the ligament balancer to measure its position. The controllers can be wirelessly connected to a display or tablet computer with touchscreen that displays the user interface. The ligament balancer could have only one upper paddle and one motor/gear/slider assembly instead of two. In the case of total knee, uni-knee, and other arthroplasty procedures, the ligament balancer may be mechanically coupled to cutting or drilling guides, to optimally position a cutting guide at the appropriate resection level to have balanced ligament tension. For instance, a cutting guide (or drill guide for drilling holes in the bone for receiving pins for securing a cutting guide) can be attached to the upper paddles, the lower paddle or the body of the ligament balancer (which is in a fixed position relative to the lower paddle). When the ligament balancer is inserted in the knee after a tibial cut is made, and the uncut femur is positioned with respect to the tibia under the desired tension created by the ligament balancer in force or height control mode, the holes can be directly drilled in the femur using the guide attached to the lower paddles or body. This marks the location of the cutting guide such that the appropriate amount of bone is resected to replicate the desired tension. This can be performed for a distal femoral and/or a posterior femoral resection, for example, in total or uni-compartmental knee arthroplasty.

Figure 17A:
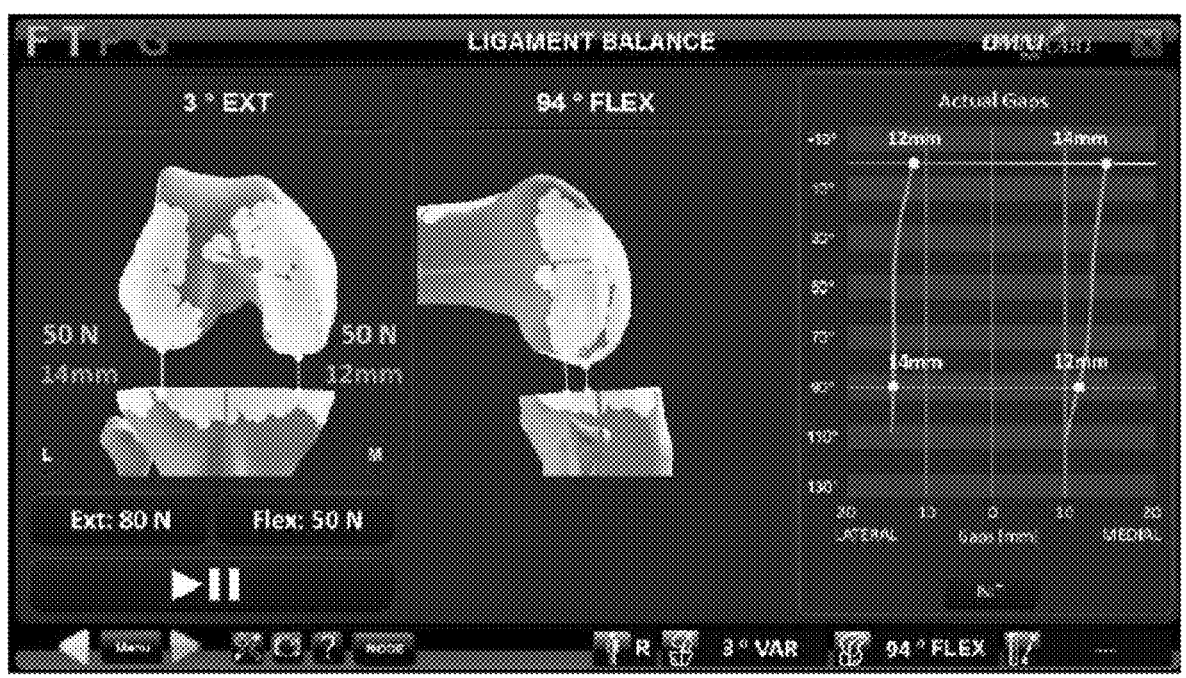
FIG. 17A is a screen shot view of a ligament balancing user interface in accordance with an aspect of the computer aided orthopedic surgery system of the present invention.
Figure 17B:
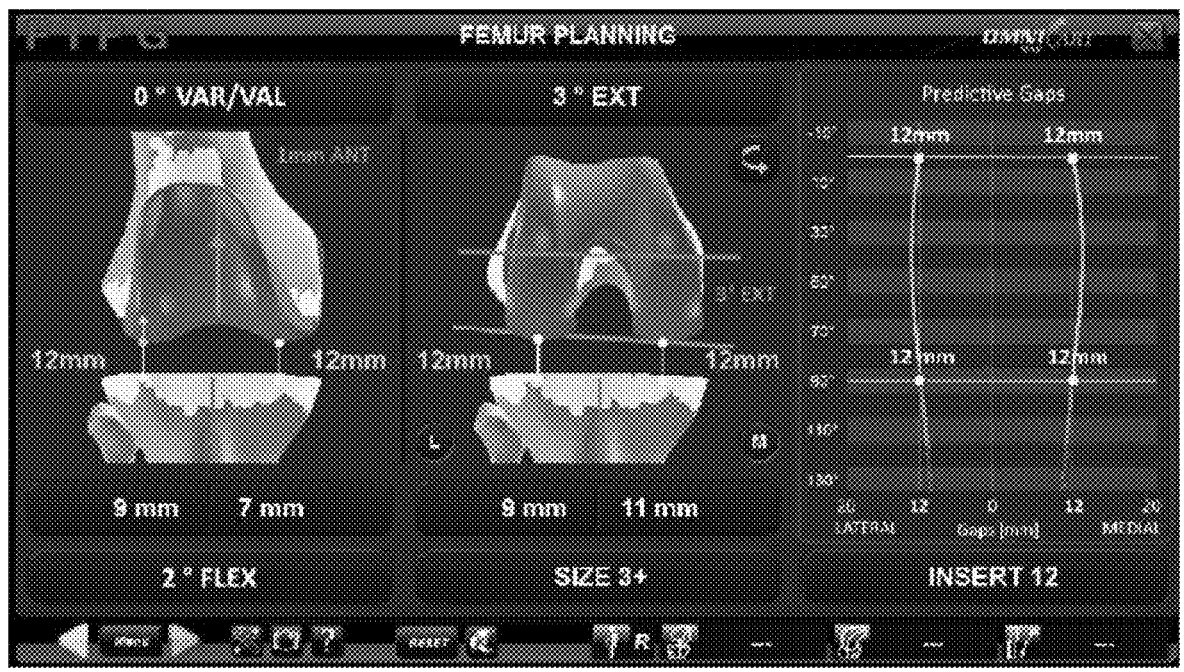
FIG. 17B is a screen shot view of an implant planning user interface in accordance with another aspect of the computer aided orthopedic surgery system.
Figure 17C:
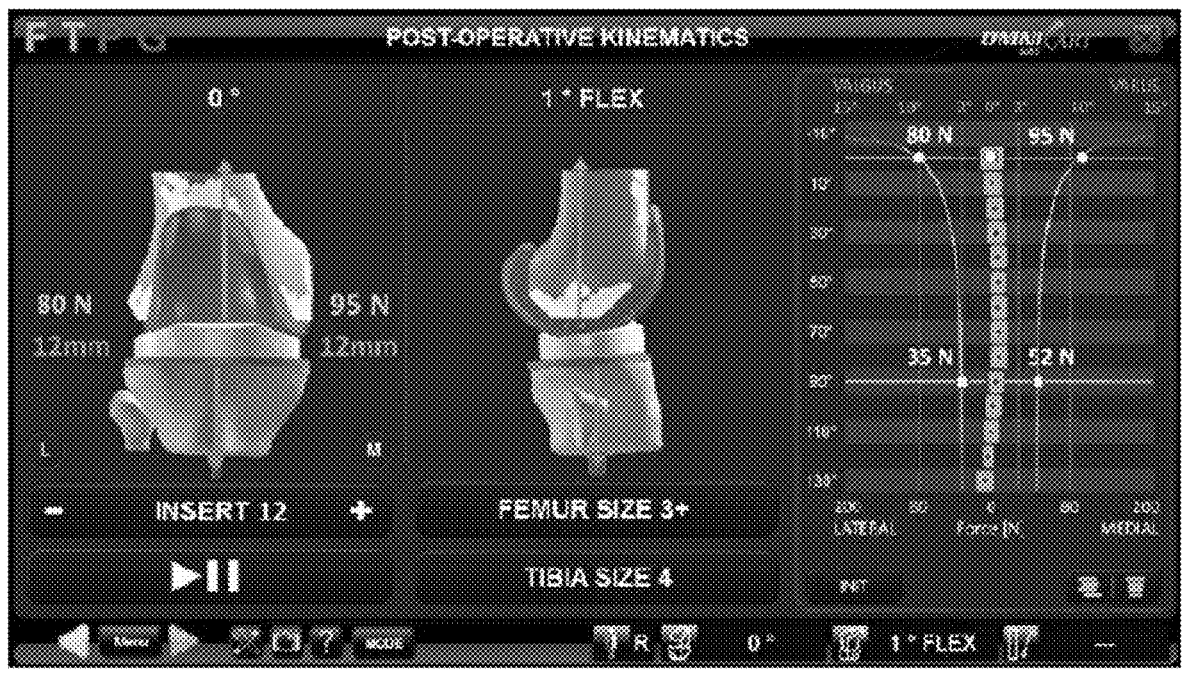
FIG. 17C is a screen shot view of a post-operative kinematics user interface in accordance with an aspect of the computer aided orthopedic surgery system.

In accordance with an aspect, the computer aided orthopedic surgery system of the present invention includes a ligament balancing user interface, as shown e.g., in FIG. 17A, an implant planning user interface, as shown e.g., in FIG. 17B, and a post-operative kinematics user interface, as shown e.g., in FIG. 17C.

In accordance with another preferred embodiment, the present invention provides a kit 600, as shown in FIGS. 21 and 16. The kit 600 includes a plurality of femoral trail implants 602 of incrementally different sizes and an orthopedic distraction device, such as ligament balancer 1. The orthopedic distraction device 1 can as described in any of the above embodiments and includes a first upper paddle 21, a plurality of lower paddles 12', and a displacement mechanism 9 having a drive assembly operable to move the upper paddle relative to the lower paddle. Each lower paddle 12 is independently connectable to the displacement mechanism. The orthopedic distraction device further includes a plurality of augments 43 each releasably connectable to the first upper paddle. Each of the plurality of augments 43 has an articulating surface that corresponds in size to a size of each of the plurality of femoral trial implants 602.

The kit 600 further includes a plurality of tibial implants 604. Each of the plurality of lower paddles 12' has an overall profile sized and shaped to correspond to a size and shape of an overall profile of the plurality of tibial implants. A plurality of tibial insert implants 606 can optionally be included in the kit 600.

The present invention as described in the above embodiments advantageously reduce the number of instruments (manual trials) in the OR. Typically, a range of tibial trial (or provisional) baseplates, tibial trial inserts and femoral trails are made available in the operating room to allow a surgeon to provisionally insert into the joint and trial the size of prosthesis to be implanted in the joint. Trialing allows the surgeon to be sure that the selected implant size is the correct fit and provides the patient with the correct soft-tissue tension and balance, before opening and inserting the final implant components into the joint. Typically, the range of sizes offered for the tibial baseplate and femoral component can be anywhere from 6 to 12 per implant (tibia and femur). Moreover, each size of tibial insert implant can be offered in several different thicknesses, for example 7 different thicknesses may be offered: 10 mm, 11 mm, 12 mm, 14 mm, 16 mm, 18 mm and 20 mm. When combining this with the number of different sizes of tibial baseplates and femoral components, this can lead to a large number of tibial insert sizes that need to be included in the instrument set (for instance 6×7, or 42 different tibial insert sizes and thicknesses). Moreover, if different styles of tibial inserts are offered (for example, cruciate retaining (CR), ultra-congruent (UC), or posterior stabilized (PS)), one per type may also need to be provided. However, providing every size of implant as a trial component in the operating room can lead to increased costs and complexity due to the large number of components that need to be manufactured by the implant company, and when used on a reusable basis, cleaned and re-sterilized by the hospital after every case. Moreover, having a large amount of instruments in the OR makes the procedure more complex with more parts to deal with and more space taken up with instrumentation on the back table of the OR. An object of the present invention is to provide a system that reduces the number of instruments that are required for trialing in the operating room. Additionally, conventional trial implants do not provide information as to the forces acting on the joint during the procedure, which can affect the outcome of the surgery. Thus the present invention provide an improved trialing process that provides feedback to surgeon as to the forces acting on and being applied to the joint.

It will be appreciated rotational by those skilled in the art that changes could be made to the preferred embodiments described above without departing from the broad inventive concept thereof. It is to be understood, therefore, that this invention is not limited to the particular embodiments disclosed, but it is intended to cover modifications within the spirit and scope of the present invention as defined by the claims.

We claim:

1. A method of planning an arthroplasty procedure of a joint comprising:
attaching an orthopedic distraction device to a first bone of a joint before any bone resections of the first bone and a second bone of the joint, the orthopedic distraction device including:
an upper paddle for engaging the second bone, and
a displacement mechanism having a mechanical drive assembly connected to the upper paddle and operable to displace the upper paddle relative to the first bone;
using the orthopedic distraction device, applying a displacement force to displace the upper paddle from the first bone, and measuring a gap spacing between the first and second bones of the joint upon applying the displacement force; and
planning a bone resection of one of the first and second bones of the joint based on the measured gap spacing between the first and second bones of the joint.

2. The method of claim 1, further comprising resecting one of the first and second bones after the step of planning the bone resection.

3. The method of claim 1, wherein the step of applying a displacement force comprises applying varying displacement forces at various degrees of flexion of the joint.

4. The method of claim 3, wherein the step of applying varying displacement forces comprises adjusting the displacement force at various degrees of flexion of the joint.

5. The method of claim 1, wherein the step of planning comprises planning a bone resection of the first bone and the second bone of the joint based on the measured gap spacing between the first and second bones of the joint.

6. The method of claim 1, further comprising planning an implant position for one of the first and second bones of the joint based on the measured gap spacing.

7. The method of claim 1, wherein the step of planning comprises adjusting an implant position for one of the first and second bones based on the measured gap spacing and a bone resection of one of the first and second bones of the joint.

8. A method of performing an arthroplasty procedure of a joint using a computer aided orthopedic surgery system that includes an orthopedic distraction device, a three-dimensional position tracking system, and a computer operatively in communication with the orthopedic distraction device and the three-dimensional position tracking system, comprising:
attaching the orthopedic distraction device to a first bone of a joint before any bone resections of the first bone and a second bone of the joint, the orthopedic distraction device including:
an upper paddle for engaging the second bone, and
a displacement mechanism operable to displace the upper paddle relative to the first bone;
using the orthopedic distraction device, applying a displacement force to displace the upper paddle from the first bone;
using the three-dimensional position tracking system, determining a relative position of the first bone and the second bone upon application of the displacement force; and
using the computer, determining a predicted gap between the first and second bones of the joint based on the relative position of the first bone and the second bone and the displacement force.

9. The method of claim 8, further comprising planning a bone resection of one of the first and second bones of the joint based on the predicted gap.

10. The method of claim 8, further comprising planning a bone resection of the first bone and the second bone of the joint based on the predicted gap.

11. The method of claim 8, further comprising planning a position of an implant on one of the first and second bones of the joint based on the predicted gap.

12. The method of claim 8, further comprising resecting one of the first and second bones after the step of determining a predicted gap.

13. The method of claim 8, wherein the step of applying a displacement force comprises applying varying displacement forces at various degrees of flexion of the joint.

14. The method of claim 13, wherein the step of determining a relative position comprises measuring a gap spacing between the first bone and the second bone upon application of the varying displacement forces.

15. The method of claim 13, wherein the step of applying varying displacement forces comprises adjusting the displacement force at various degrees of flexion of the joint.

16. The method of claim 8, wherein the step of determining a relative position comprises determining a relative position between the first and second bones of the joint through a range of motion of the joint.

17. The method of claim 8, further comprising, using the computer, determining an implant alignment for an implant to be implanted on one of the first and second bones of the joint based on the determined predicted gap.

18. The method of claim 17, further comprising:
planning an implant position for one of the first and second bones of the joint based on the predicted gap;
planning a bone resection of one of the first and second bones of the joint based on the predicted gap, and
adjusting the planned implant position based on the predicted gap, the bone resection, and the implant alignment.

19. The method of claim 8, further comprising, using the computer, displaying the predicted gap on a display.

20. The method of claim 8, further comprising using the three-dimensional position tracking system, tracking a position of the first bone and the second bone, and wherein determining a relative position of the first bone and the second bone upon application of the displacement force is based on the tracked positions of the first bone and the second bone.

* * * * *